(12) United States Patent
Kang et al.

(10) Patent No.: US 11,754,486 B2
(45) Date of Patent: Sep. 12, 2023

(54) SYSTEMS AND METHODS FOR MEASURING PROPERTIES OF PARTICLES

(71) Applicant: Massachusetts Institute of Technology, Cambridge, MA (US)

(72) Inventors: Joon Ho Kang, Cambridge, MA (US); Selim Olcum, Cambridge, MA (US); Scott R. Manalis, Portland, OR (US)

(73) Assignee: Massachusetts Institute of Technology, Cambridge, MA (US)

( * ) Notice: Subject to any disclaimer, the term of this patent is extended or adjusted under 35 U.S.C. 154(b) by 744 days.

(21) Appl. No.: 16/624,000

(22) PCT Filed: Jun. 18, 2018

(86) PCT No.: PCT/US2018/037995
§ 371 (c)(1),
(2) Date: Dec. 18, 2019

(87) PCT Pub. No.: WO2018/236708
PCT Pub. Date: Dec. 27, 2018

(65) Prior Publication Data
US 2021/0148806 A1    May 20, 2021

Related U.S. Application Data

(60) Provisional application No. 62/521,894, filed on Jun. 19, 2017.

(51) Int. Cl.
*G01N 15/10* (2006.01)
*B01L 3/00* (2006.01)
*G01N 33/50* (2006.01)

(52) U.S. Cl.
CPC .... *G01N 15/1056* (2013.01); *B01L 3/502761* (2013.01); *G01N 33/5011* (2013.01);
(Continued)

(58) Field of Classification Search
CPC .......... G01N 15/1056; G01N 33/5011; G01N 2015/1006; G01N 2015/1043;
(Continued)

(56) References Cited

U.S. PATENT DOCUMENTS 7,215,214 B1    5/2007   Taheri et al.
7,387,889 B2    6/2008   Manalis
(Continued)

FOREIGN PATENT DOCUMENTS

CN     104677808 A    6/2015
FR       2996219 A1   4/2014
(Continued)

OTHER PUBLICATIONS

Bryan et al.; "Measuring single cell, mass, volume and density with dual suspended microchannel resonators", Lab Chip, 2014; (Year: 2014).*

(Continued)

*Primary Examiner* — Joseph C Rodriguez
(74) *Attorney, Agent, or Firm* — Wolf, Greenfield & Sacks, P.C.

(57) ABSTRACT

Systems and methods for measuring the properties (e.g., mechanical properties) of particles such as biological entities, in a fluidic channel(s) are generally provided. In some embodiments, the systems and methods comprise measuring an acoustic scattering of single particles. For example, a single particle (e.g., a biological entity) may be flowed in a suspended fluidic channel (e.g., a suspended microfluidic channel) and the fluidic channel is oscillated at or near a (mechanical) resonant frequency (e.g., at a second or higher bending mode) of the suspended fluidic channel. In some cases, an acoustic scattering signal (e.g., the change in resonant frequency of the fluidic channel as the particle flows along a longitudinal axis of the channel) may corre-
(Continued)

spond to a property (e.g., a mechanical property, a cross-linking density, a transport rate of small molecules into/out of the particle) of the particle. In certain embodiments, the systems and methods comprise determining a node deviation due to a single particle (or node deviations for a plurality of particles).

23 Claims, 69 Drawing Sheets

(52) U.S. Cl.
CPC ............... *B01L 2200/0652* (2013.01); *B01L 2400/0436* (2013.01); *G01N 2015/1006* (2013.01); *G01N 2015/1043* (2013.01)

(58) Field of Classification Search
CPC ....... B01L 3/502761; B01L 2200/0652; B01L 2400/04346
See application file for complete search history.

(56) References Cited

U.S. PATENT DOCUMENTS

| | | |
|---|---|---|
| 7,449,968 B1 | 11/2008 | Cioffi et al. |
| 7,812,680 B1 | 10/2010 | Brown et al. |
| 7,838,284 B2 | 11/2010 | Manalis |
| 8,087,284 B2 | 1/2012 | Babcock et al. |
| 8,291,750 B1 | 10/2012 | Goodbread et al. |
| 8,722,419 B2 | 5/2014 | Manalis et al. |
| 9,027,388 B2 | 5/2015 | Babcock et al. |
| 9,134,294 B2 | 9/2015 | Manalis et al. |
| 9,134,295 B1 * | 9/2015 | Delgado ............... G01N 9/002 |
| 9,344,805 B2 | 5/2016 | Felberer et al. |
| 9,347,815 B2 | 5/2016 | Roukes et al. |
| 9,383,282 B2 | 7/2016 | Besling et al. |
| 9,515,608 B2 | 12/2016 | Gourlat et al. |
| 9,709,400 B2 | 7/2017 | Kapusta |
| 9,757,727 B2 | 9/2017 | Manalis et al. |
| 11,143,548 B2 | 10/2021 | Cermak et al. |
| 11,162,886 B2 | 11/2021 | Kimmerling et al. |
| 2003/0027225 A1 | 2/2003 | Wada et al. |
| 2003/0033876 A1 | 2/2003 | Roukes et al. |
| 2003/0176174 A1 | 9/2003 | Seppinen et al. |
| 2005/0064581 A1 | 3/2005 | Manalis et al. |
| 2005/0164236 A1 | 7/2005 | Su et al. |
| 2007/0176705 A1 | 8/2007 | Sutardja |
| 2007/0178529 A1 | 8/2007 | Breidford et al. |
| 2009/0014360 A1 | 1/2009 | Toner et al. |
| 2009/0044608 A1 | 2/2009 | Babcock et al. |
| 2009/0053749 A1 | 2/2009 | Manalis et al. |
| 2009/0261241 A1 | 10/2009 | Roukes et al. |
| 2010/0154535 A1 | 6/2010 | Manalis et al. |
| 2010/0219914 A1 | 9/2010 | Sadek et al. |
| 2010/0263445 A1 | 10/2010 | Hayner et al. |
| 2010/0315138 A1 | 12/2010 | Namba et al. |
| 2011/0113856 A1 | 5/2011 | Cobianu et al. |
| 2011/0271412 A1 | 11/2011 | Rychen |
| 2014/0013848 A1 | 1/2014 | Colinet et al. |
| 2014/0156224 A1 | 6/2014 | Roukes et al. |
| 2014/0246322 A1 | 9/2014 | Katsumoto et al. |
| 2014/0306623 A1 | 10/2014 | Caffee et al. |
| 2014/0312980 A1 | 10/2014 | Villard et al. |
| 2015/0268244 A1 | 9/2015 | Cho et al. |
| 2015/0285784 A1 | 10/2015 | Delgado et al. |
| 2015/0300999 A1 | 10/2015 | Andreucci et al. |
| 2015/0308990 A1 | 10/2015 | Andreucci et al. |
| 2015/0343444 A1 | 12/2015 | Manalis et al. |
| 2016/0091544 A1 | 3/2016 | Daneshmand et al. |
| 2016/0123858 A1 | 5/2016 | Kapur et al. |
| 2016/0181977 A1 | 6/2016 | Gourlat et al. |
| 2016/0296932 A1 | 10/2016 | Tan |
| 2017/0089819 A1 | 3/2017 | Bahl et al. |
| 2017/0117905 A1 * | 4/2017 | Cermak ................ H03L 7/00 |
| 2018/0207639 A1 | 7/2018 | Butler et al. |
| 2018/0245972 A1 | 8/2018 | Cermak et al. |
| 2018/0299362 A1 | 10/2018 | Kimmerling et al. |
| 2021/0046477 A1 | 2/2021 | Manalis et al. |
| 2021/0293693 A1 * | 9/2021 | Bharadwaj ......... G01N 15/1484 |
| 2022/0136949 A1 | 5/2022 | Kimmerling et al. |

FOREIGN PATENT DOCUMENTS

| | | | |
|---|---|---|---|
| JP | 2007-506977 A | 3/2007 | |
| JP | 2013-543127 A | 11/2013 | |
| JP | 2014-006211 A | 1/2014 | |
| JP | 2014-510921 A | 5/2014 | |
| WO | WO 03/89158 A1 | 10/2003 | |
| WO | WO-2007081902 A2 * | 7/2007 | ......... G01N 15/1056 |
| WO | WO 2012/059828 A2 | 5/2012 | |
| WO | WO 2015/155044 A1 | 10/2015 | |
| WO | WO-2016069634 A9 * | 6/2017 | ............. G01H 13/00 |

OTHER PUBLICATIONS

International Search Report and Written Opinion dated Jun. 8, 2018 for Application No. PCT/US2018/025040.
International Preliminary Report on Patentability dated Oct. 10, 2019 for Application No. PCT/US2018/025040.
Extended European Search Report dated Mar. 26, 2021 for EP Application No. 18774395.0.
International Search Report and Written Opinion dated Jan. 22, 2016 for Application No. PCT/US2015/057634.
International Preliminary Report on Patentability dated May 11, 2017 for Application No. PCT/US2015/057634.
International Search Report and Written Opinion dated Aug. 17, 2020 for Application No. PCT/US2020/037770.
Albrecht et al., Frequency modulation detection using high-Q cantilevers for enhanced force microscope sensitivity. J Appl Phys. Jan. 15, 1991;69(2):668-73.
Ananthakrishnan et al., Quantifying the contribution of actin networks to the elastic strength of fibroblasts. J Theor Biol. Sep. 21, 2006;242(2):502-16. Epub May 23, 2006.
Atia et al., A phase-locked shear-force microscope for distance regulation in near-field optical microscopy. Appl Phys Lett. Jan. 27, 1997;70(4):405-7.
Bagnall et al., Deformability-based cell selection with downstream immunofluorescence analysis. Integr Biol (Camb). May 16, 2016;8(5):654-64. doi: 10.1039/c5ib00284b. Epub Mar. 11, 2016.
Balland et al., Power laws in microrheology experiments on living cells: Comparative analysis and modeling. Phys Rev E Stat Nonlin Soft Matter Phys. Aug. 2006; 74(2 Pt 1):021911(1-17). Epub Aug. 9, 2006.
Bouloc et al., All digital control system for a novel high frequency force sensor in non contact atomic force microscopy, IEEE Sensors, Oct. 2012;2012:pp. 1-4. doi : 10.1109/ICSENS.2012.6411039.
Bouloc et al., FPGA-based programmable digital PLL with very high frequency resolution. 2011 18th IEEE Intl Conf on Electronics, Circuits, and Systems. Dec. 11-14, 2011;370-3.
Brangwynne et al., Force fluctuations and polymerization dynamics of intracellular microtubules. Proc Natl Acad Sci U S A. Oct. 9, 2007;104(41):16128-33. Epub Oct. 2, 2007.
Bremer et al., Modulation of chemical composition and other parameters of the cell at different exponential growth rates. EcoSal Plus. Sep. 2008;3(1):(1-49). doi: 10.1128/ecosal.5.2.3.
Bruus, Acoustofluidics 1 : Governing equations in microfluidics. Lab Chip. Nov. 21, 2011;11(22):3742-51. doi: 10.1039/c11c20658c. Epub Oct. 20, 2011.
Bryan et al., Measurement of mass, density, and volume during the cell cycle of yeast. Proc Natl Acad Sci U S A. Jan. 19, 2010;107(3):999-1004. doi: 10.1073/pnas.0901851107. Epub Dec. 23, 2009.
Burg et al., Nonmonotonic energy dissipation in microfluidic resonators. Phys Rev Lett. Jun. 5, 2009;102(22):228103(1-4). Epub Jun. 4, 2009.
Burg et al., Weighing of biomolecules, single cells and single nanoparticles in fluid. Nature. Apr. 26, 2007;446(7139):1066-9.

(56) References Cited

OTHER PUBLICATIONS

Butzin et al., Analysis of the effects of a gerP mutation on the germination of spores of Bacillus subtilis. J Bacteriol. Nov. 2012; 194(21):5749-58. doi: 10.1128/JB.01276-12. Epub Aug. 17, 2012.
Byun et al., Characterizing cellular biophysical responses to stress by relating density, deformability, and size. Biophys J. Oct. 20, 2015;109(8):1565-73. doi: 10.1016/j.bpj.2015.08.038.
Byun et al., Characterizing deformability and surface friction of cancer cells. Proc Natl Acad Sci U S A. May 7, 2013;110(19):7580-5. doi: 10.1073/pnas.1218806110. Epub Apr. 22, 2013.
Caldwell et al., Measurement of the size and density of colloidal particles by combining sedimentation field-flow fractionation and quasi-elastic light scattering. Colloids and Surfaces. May 1986; 18(1):123-31.
Cartagena-Rivera et al., Actomyosin cortical mechanical properties in nonadherent cells determined by atomic force microscopy. Biophys J. Jun. 7, 2016;110(11):2528-2539. doi: 10.1016/j.bpj.2016.04.034.
Cermak et al., Direct single-cell biomass estimates for marine bacteria via Archimedes' principle. ISME J. Mar. 2017;11(3):825-828. doi: 10.1038/ismej.2016.161. Epub Dec. 6, 2016.
Cermak et al., High-throughput measurement of single-cell growth rates using serial microfluidic mass sensor arrays. Nat Biotechnol. Oct. 2016;34(10):1052-1059. doi: 10.1038/nbt.3666. Epub Sep. 5, 2016.
Cetin et al., Determining therapeutic susceptibility in multiple myeloma by single-cell mass accumulation. Nat Commun. Nov. 20, 2017;8(1):1613(1-12). doi: 10.1038/s41467-017-01593-2.
Chaste et al., A nanomechanical mass sensor with yoctogram resolution. Nat Nanotechnol. May 2012;7(5):301-4. doi: 10/1038/nnano.2012.42. Epub Apr. 1, 2012.
Chugh et al., Actin cortex architecture regulates cell surface tension. Nat Cell Biol. Jun. 2017; 19(6):689-697. Suppl Info 19 pages. doi: 10.1038/ncb3525. Epub May 22, 2017.
Clark et al., Monitoring actin cortex thickness in live cells. Biophys J. Aug. 6, 2013;105(3):570-80. doi: 10.1016/j.bpj.2013.05.057.
Cooper et al., Multiple phases of chondrocyte enlargement underlie differences in skeletal proportions. Nature. 2013;495:375-8. Epub Mar. 13, 2013. Author manuscript provided. 13 pages.
Delgado et al., Intracellular water exchange for measuring the dry mass, water mass and changes in chemical composition of living cells. PLoS One. Jul. 2013;8(7):e67590(1-11).
Dendukuri et al., Continuous-flow lithography for high-throughput microparticle synthesis. Nat Mater. May 2006;5(5):365-9. Epub Apr. 9, 2006.
Dendukuri et al., Stop-flow lithography in a microfluidic device. Lab Chip. Jul. 2007; 7(7):818-28. Epub May 21, 2007.
Dextras et al., Integrated measurement of the mass and surface of discrete microparticles using a suspended microchannel resonator. Anal Chem. 2009;81:4517-23.
Di Carlo et al., Continuous inertial focusing, ordering, and separation of particles in microchannels. Proc Natl Acad Sci. Nov. 27, 2007;104(48):18892-7.
Dohn et al., Mass and position determination of attached particles on cantilever based mass sensors. Rev Sci Instrum. Oct. 2007;78(10):103303(1-3). Epub Oct. 31, 2010.
Dohn et al., Position and mass determination of multiple particles using cantilever based mass sensors. Appl Phys Lett. 2010;97(4):044103(1-3). Epub Jul. 29, 2010.
Ekinci et al., Ultimate limits to inertial mass sensing based upon nanoelectromechanical systems. J Appl Phys. Mar. 1, 2004;95(5):2682-9.
Fischer-Friedrich et al., Rheology of the active cell cortex in mitosis. Biophys J. Aug. 9, 2016;111(3):589-600. doi: 10.1016/j.bpj.2016.06.008.
Fraikin et al., A high-throughput label-free nanoparticle analyser. Nat Nanotechnol. May 2011;6(5):308-13. doi: 10.1038/nnano.2011.24. Epub Mar. 6, 2011.
Gardel et al., Mechanical integration of actin and adhesion dynamics in cell migration. Annu Rev Cell Dev Biol. 2010;26:315-33. doi: 10.1146/annurev.cellbio.011209.122036. Epub May 17, 2010.

Gavartin et al., Stabilization of a linear nanomechanical oscillator to its thermodynamic limit. Nat Commun. 2013;4:2860(1-8). doi: 10.1038/ncomms3860. Epub Dec. 11, 2013.
Georgatos et al., Nuclear envelope breakdown in mammalian cells involves stepwise lamina disassembly and microtubule-drive deformation of the nuclear membrane. J Cell Sci. Sep. 1997;110( Pt 17):2129-40.
Gerhardt et al., Permeability of bacterial spores. II. Molecular variables affecting solute permeation. J Bacteriol. Nov. 1961; 82:750-60.
Godin et al., Using buoyant mass to measure the growth of single cells. Nat Methods. May 2010;7(5):387-90. Suppl Info 2 pages. doi: 10.1038/nmeth.1452. Epub Apr. 11, 2010.
Goldstein, Newsletter—MIT Faculty Profile: Scott Manalis. Retrieved Oct. 25, 2015. Accessed from <https://web.archive.org.web/2015*/ https://be.mit.edu/news-events/newsletter/newsletter-spring-2014-faculty-profile-scott-manalis;hereinafter"Newsletter">.
Gossett et al., Hydrodynamic stretching of single cells for large population mechanical phenotyping. Proc Natl Acad Sci U S A. May 15, 2012;109(20):7630-5. doi: 10.1073/pnas.1200107109. Epub Apr. 30, 2012.
Grover et al., Measuring single-cell density. Proc Natl Acad Sci U S A. Jul. 5, 2011;108(27):10992-6. doi: 10.1073/pnas.1104651108. Epub Jun. 20, 2011. Early Edition, 5 pages.
Guillou et al., Dynamic monitoring of cell mechanical properties using profile microindentation. Sci Rep. Feb. 9, 2016;6:21529(1-13). doi: 10.1038/srep21529.
Guo et al., Cell volume change through water efflux impacts cell stiffness and stem cell fate. Proc Natl Acad Sci U S A. Oct. 10, 2017;114(41):E8618-E8627. doi: 10.1073/pnas.1705179114. Epub Sep. 25, 2017. Early Edition, 10 pages.
Gupta et al., Equilibrium and out-of-equilibrium mechanics of living mammalian cytoplasm. J Mechan Phys Solids. 2017;107:284-93. Epub Jul. 8, 2017.
Hanay et al., Single-protein nanomechanical mass spectrometry in real time. Nat Nanotechnol. Sep. 2012;7(9):602-8. doi: 10.1038/nnano.2012.119. Epub Aug. 26, 2012.
Hartono et al., On-chip measurements of cell compressibility via acoustic radiation. Lab Chip. Dec. 7, 2011;11(23):4072-80. Epub Oct. 21, 2011.
Henderson et al., Actin filament dynamics in living glial cells imaged by atomic force microscopy. Science. Sep. 25, 1992;257(5078):1944-6.
Hiramoto et al., Mechanical properties of the surface of the sea urchin egg at fertilization and during cleavage. Exp Cell Res. Dec. 1974;89(2):320-6.
Hogenauer, An economical class of digital filters for decimation and interpolation. IEEE Trans on Acoustics, Speech, and Signal Processing. Apr. 1981;29(2):155-62.
Ivanova et al., Bactericidal activity of black silicon. Nat Commun. 2013;4:2838(1-7). doi: 10.1038/ncomms3838. Epub Nov. 26, 2013.
Jin et al., A microfluidic device enabling high-efficiency single cell trapping. Biomicrofluidics. Jan. 7, 2015;9:014101(1-16).
Khalili et al., A microfluidic device for hydrodynamic trapping and manipulation platform of a single biological cell. Appl Sci. Feb. 1, 2016;6(40):1-17.
Khodabandehloo et al., Particle sizing methods for the detection of protein aggregates in biopharmaceuticals. Bioanalysis. 2017;9(3):313-26. Epub Jan. 18, 2017.
Kimmerling et al., A microfluidic platform enabling single-cell RNA-seq of multigenerational lineages. Nat Commun. Jan. 6, 2016;7:10220(1-7). doi: 10.1038/ncomms10220. Epub Jan. 6, 2016.
Kimmerling, A toolset for linking phenotype and gene expression at the single-cell level. Doctoral Thesis—Massachusetts Institute of Technology. Feb. 2017. 142 pages.
Knudsen et al., Water and small-molecule permeation of dormant Bacillus subtilis spores. J Bacteriol. Jan. 2016; 198(1): 168-77. doi: 10.1128/JB.00435-15. Epub Oct. 19, 2015.
Kobayashi et al., Frequency noise in frequency modulation atomic force microscopy. Rev Sci Instrum. Apr. 2009;80(4):043708(1-8). doi: 10.1063/1.3120913. Epub Apr. 27, 2009.

(56) References Cited

OTHER PUBLICATIONS

Kouh et al., Room-temperature operation of a nanoelectromechanical resonator embedded in a phase-locked loop. Appl Phys Lett. 2005;87(11):113112(1-3). Epub Sep. 9, 2005.
Kundu et al., Measuring elastic properties of cells by evaluation of scanning acoustic microscopy V(Z) values using simplex algorithm. Biophys J. May 1991; 59(6):1194-207.
Lee et al., Suspended microchannel resonators with piezoresistive sensors. Lab Chip. Feb. 21, 2011;11(4):645-51. doi: 10.1039/c0lc00447b. Epub Dec. 22, 2010.
Lee et al., Toward attogram mass measurements in solution with suspended nanochannel resonators. Nano Lett. Jul. 14, 2010;10(7):2537-42. doi: 10.1021/nl101107u. Epub Jun. 8, 2010.
Lim et al., Mechanical models for living cells—a review. J Biomech. 2006;39(2):195-216.
Lincoln et al., High-throughput rheological measurements with an optical stretcher. Methods Cell Biol. 2007;83:397-423.
Matzke et al., Direct, high-resolution measurement of furrow stiffening during division of adherent cells. Nat Cell Biol. Jun. 2001;3(6):607-10.
Narayanamurthy et al., Microfluidic hydrodynamic trapping for single cell analysis: mechanisms, methods and applications. Anal Methods. May 12, 2017;9:3751-72. doi: 10.1039/c7ay00656j.
Olcum et al., High-speed multiple-mode mass-sensing resolves dynamic nanoscale mass distributions. Nat Commun. 2015;6:7070(1-8). doi: 10/1038/ncomms8070. Epub May 12, 2015.
Olcum et al., Weighing nanoparticles in solution at the attogram scale. Proc Natl Acad Sci U S A. Jan. 28, 2014;111(4):1310-5. doi: 10.1073/pnas.1318602111. Epub Jan. 13, 2014.
Otto et al., Real-time deformability cytometry: on-the-fly cell mechanical phenotyping. Nat Methods. Mar. 2015;12(3):199-202, 4 p following 202. doi: 10.1038/nmeth.3281. Epub Feb. 2, 2015.
Ou-Yang et al., Complex fluids: Probing mechanical properties of biological systems with optical tweezers. Annu Rev Phys Chem. 2010;61:421-40. doi: 10.1146/annurev.physchem.012809.103454. Epub Jan. 4, 2010.
Paluch et al., Biology and physics of cell shape changes in development. Curr Biol. Sep. 15, 2009;19(17):R790-9. doi: 10.1016/j.cub.2009.07.029.
Plomp et al., Architecture and assembly of the Bacillus subtilis spore coat. PLoS One. Sep. 26, 2014;9(9):e108560(1-16). doi: 10.1371/journal.pone.0108560. eCollection 2014.
Pritchard et al., The role of F-actin in hypo-osmotically induced cell volume change and calcium signaling in anulus fibrosus cells. Ann Biomed Eng. Jan. 2004;32(1):103-11.
Radmacher, Studying the mechanics of cellular processes by atomic force microscopy. Methods Cell Biol. 2007;83:347-72.
Ramanathan et al., Cdk1-dependent mitotic enrichment of cortical myosin II promotes cell rounding against confinement. Nat Cell Biol. Feb. 2015; 17(2):148-59. Suppl Info 10 pages. doi: 10.1038/ncb3098. Epub Jan. 26, 2015.
Riedl, et al., Lifeact: a versatile marker to visualize F-actin. Nat Methods. Jul. 2008;5(7):605-7. doi: 10.1038/nmeth.1220. Epub Jun. 8, 2008.
Rinke et al., Obtaining genomes from uncultivated environmental microorganisms using FACS-based single-cell genomics. Nat Protoc. May 2014;9(5):1038-48. doi: 10.1038/nprot.2014.067. Epub Apr. 10, 2014.
Riordon et al., Using active microfluidic flow focusing to sort particles and cells based on high-resolution volume measurements. Microelectronic Engineering. Apr. 25, 2014;118:35-40. Epub Feb. 13, 2014.
Rodrigues et al., Kinetochore-localized PP1-Sds22 couples chromosome segregation to polar relaxation. Nature. Aug. 27, 2015;524(7566):489-92. Suppl Info 18 pages. doi: 10.1038/nature14496. Epub Jul. 13, 2015.
Sader et al., Energy dissipation in microfluidic beam resonators: Effect of Poisson's ratio. Phys Rev E Stat Nonlin Soft Matter Phys. Aug. 2011:84(2 Pt 2):026304(1-15). Epub Aug. 5, 2011.
Sader et al., Energy dissipation in microfluidic beam resonators: Dependence on mode number. J Appl Phys. Dec. 1, 2010;108(11):114507(1-14). Epub Dec. 9, 2010.
Sauzade et al., Deterministic trapping, encapsulation and retrieval of single-cells. Lab Chip. Jun. 27, 2017;17(13):2186-92.
Scherrer et al., Density, porosity, and structure of dried cell walls isolated from Bacillus megaterium and *Saccharomyces cerevisiae*. J Bacteriol. Feb. 1977;129(2):1162-4.
Scherrer et al., Macromolecular sieving by the dormant spore of Bacillus cereus. J Bacteriol. Nov. 1971; 108(2):868-73.
Scherrer et al., Porosity of the yeast cell wall and membrane. J Bacteriol. May 1974; 118(2):534-40.
Schuler et al., A Machine Learning Approach for Non-blind Image Deconvolution. CVPR '13: Proceedings of the 2013 IEEE Conference on Computer Vision and Pattern Recognition. Jun. 2013:1067-74.
Sell et al., A digital PLL circuit for resonator sensors. Sensors and Actuators A. Feb. 26, 2011;172(1):69-74.
Sharma et al., Micro-Flow Imaging: Flow Microscopy Applied to Sub-visible Particulate Analysis in Protein Formulations. The AAPS Journal. 2010;12:455-64. Epub Jun. 2, 2010.
Son et al., Direct observation of mammalian cell growth and size regulation. Nat Methods. Sep. 2012;9(9):910-2. doi: Suppl Info 1 page. 10.1038/nmeth.2133. Epub Aug. 5, 2012.
Son et al., Resonant microchannel volume and mass measurements show that suspended cells swell during mitosis. J Cell Biol. Nov. 23, 2015;211(4):757-63. doi: 10.1083/jcb.201505058.
Steltenkamp et al., Membrane stiffness of animal cells challenged by osmotic stress. Small. Aug. 2006;2(8-9):1016-20.
Stevens et al., Drug sensitivity of single cancer cells is predicted by changes in mass accumulation rate. Nat Biotechnol. Nov. 2016;34(11):1161-1167. Suppl Info 2 pages. doi: 10.1038/nbt.3697. Epub Oct. 10, 2016.
Stewart et al., Hydrostatic pressure and the actomyosin cortex drive mitotic cell rounding. Nature. Jan. 13, 2011;469(7329):226-30. Suppl Info 1 page. doi: 10.1038/nature09642. Epub Jan. 2, 2011.
Stockslager et al., Rapid and high-precision sizing of single particles using parallel suspended microchannel resonator arrays and deconvolution. Rev Sci Instrum. Aug. 2019; 90(8): 085004. Epub Aug. 30, 2019. 10 pages.
Swaminathan et al., Mechanical stiffness grades metastatic potential in patient tumor cells and in cancer cell lines. Cancer Res. Aug. 1, 2011;71(15):5075-80. Author Manuscript 18 pages. doi: 10.1158/0008-5472.CAN-11-0247. Epub Jun. 3, 2011.
Tseng et al., Micromechanical mapping of live cells by multiple-particle-tracking microrheology. Biophys J. Dec. 2002;83(6):3162-76.
Vaclavek et al., Resistive pulse sensing as particle counting and sizing method in microfluidic systems: Designs and applications review. Journal of Separation Science. Jan. 2019;42(1):445-57. Epub Dec. 3, 2018.
Wang et al., Acoustophoretic force-based compressibility measurement of cancer cells having different metastatic potential. Proc Mtgs Acoust. Jun. 2013;19:045019(1-5).
Wang et al., Fast stiffness mapping of cells using high-bandwidth atomic force microscopy. ACS Nano. Jan. 26, 2016;10(1):257-64. doi: 10.1021/acsnano.5b03959. Epub Nov. 11, 2015.
Wang et al., Mechanotransduction across the cell surface and through the cytoskeleton. Science. May 21, 1993;260(5111):1124-7.
Yang et al., A comprehensive strategy for the analysis of acoustic compressibility and optical deformability on single cells. Sci Rep. Apr. 4, 2016;6:23946(1-11). doi: 10.1038/srep23946.
Yeung et al., Cortical shell-liquid core model for passive flow of liquid-like spherical cells into micropipets. Biophys J. Jul. 1989; 56(1):139-49.
Zlotek-Zlotkiewicz et al., Optical volume and mass measurements show that mammalian cells swell during mitosis. J Cell Biol. Nov. 23, 2015;211(4):765-74. doi: 10.1083/jcb.201505056.
International Preliminary Report on Patentability dated Feb. 24, 2022 for Application No. PCT/US2020/037770.
International Search Report and Written Opinion dated Aug. 27, 2018 for Application No. PCT/US2018/037995.

(56) References Cited

OTHER PUBLICATIONS

International Preliminary Report on Patentability dated Jan. 2, 2020 for Application No. PCT/US2018/037995.
Bryan et al., Measuring single cell mass, volume, and density with dual suspended microchannel resonators. Lab Chip. Feb. 7, 2014; 14(3): 569-576.
Lee et al., High precision particle mass sensing using microchannel resonators in the second vibration mode. Rev Sci Instrum. Feb. 2011; 82(2): 023704, 4 pages.
U.S. Appl. No. 17/496,096, filed Oct. 7, 2021, Kimmerling et al.
U.S. Appl. No. 17/463,639, filed Sep. 1, 2021, Cermak et al.
U.S. Appl. No. 16/901,924, filed Jun. 15, 2020, Manalis et al.
PCT/US2018/025040, Jun. 8, 2018, International Search Report and Written Opinion.
PCT/US2018/025040, Oct. 10, 2019, International Preliminary Report on Patentability.
EP 18774395.0, Mar. 26, 2021, Extended European Search Report.
PCT/US2015/057634, Jan. 22, 2016, International Search Report and Written Opinion.
PCT/US2015/057634, May 11, 2017, International Preliminary Report on Patentability.
PCT/US2020/037770, Aug. 17, 2020, International Search Report and Written Opinion.

\* cited by examiner

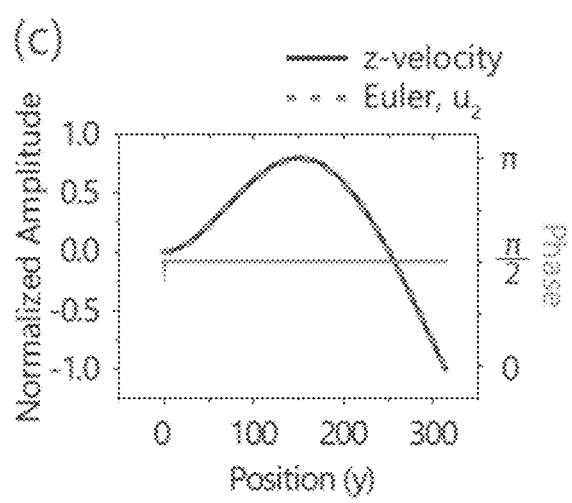
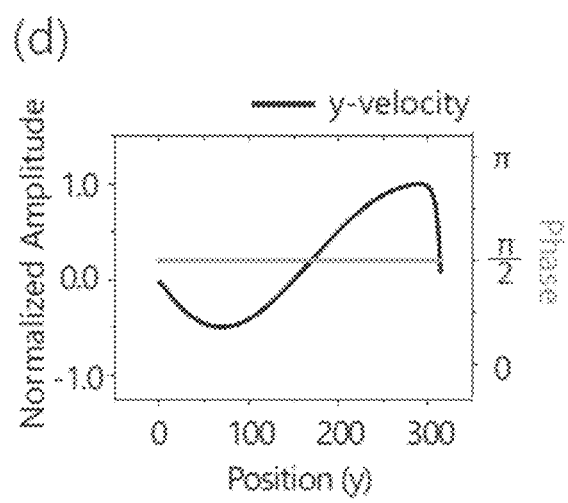
FIG. 4C
FIG. 4D

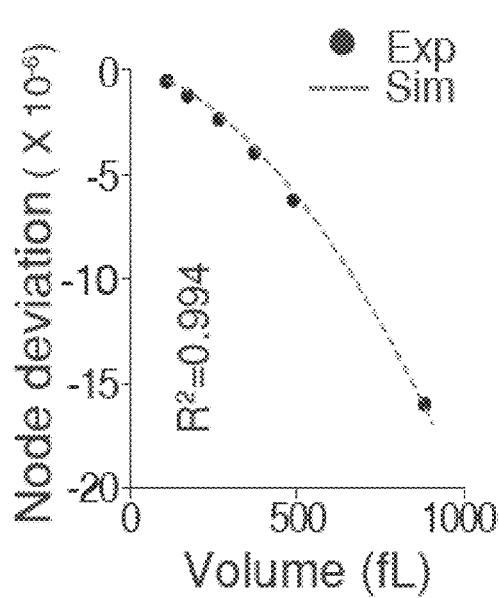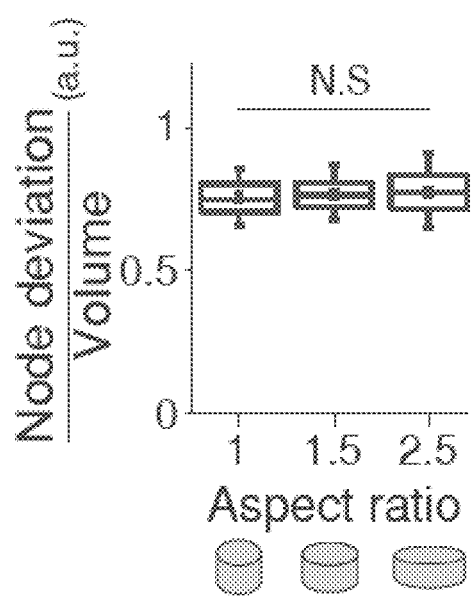
FIG. 13F
FIG. 13G

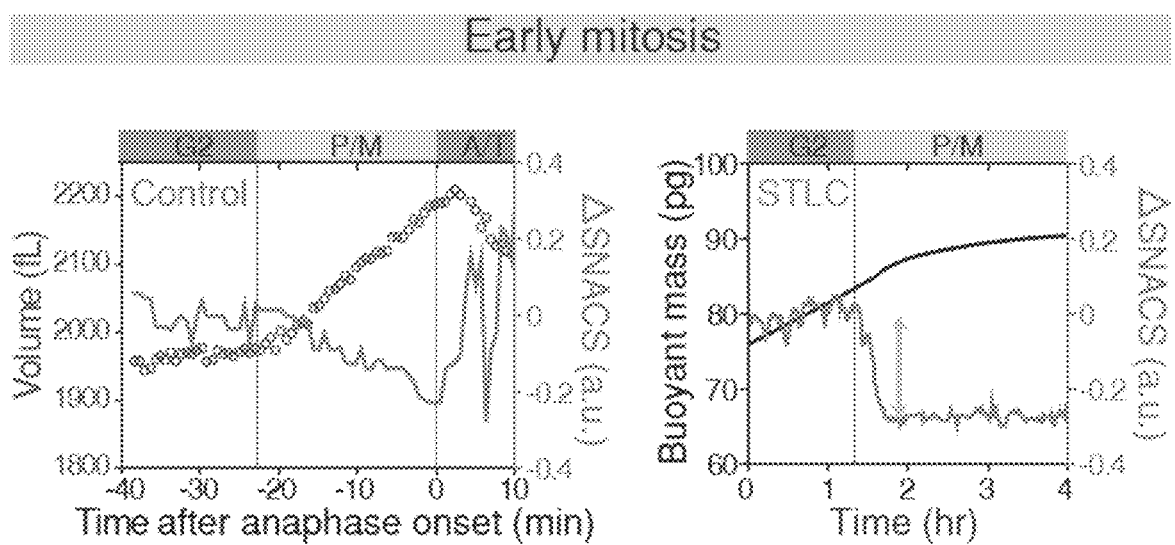
FIG. 16A  FIG. 16B
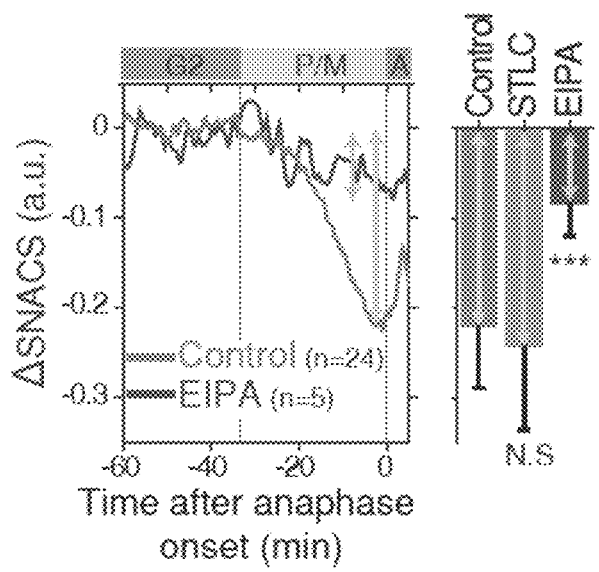 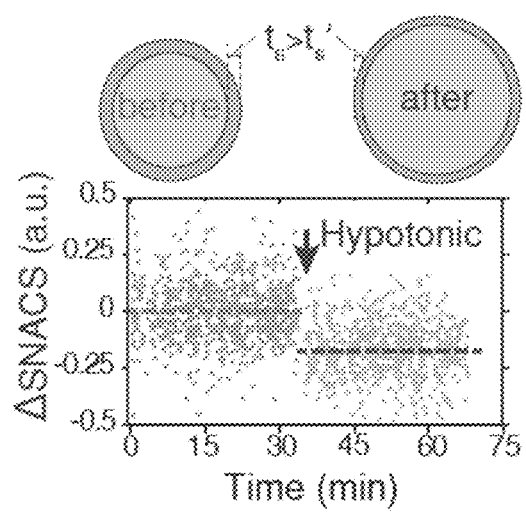
FIG. 16C  FIG. 16D

| Model | Model illustration | Simulation result |
|---|---|---|
| Viscous drop | 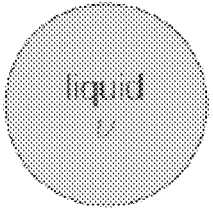 liquid | cannot reproduce positive node deviation |
| Acoustic Impedance Mismatch | 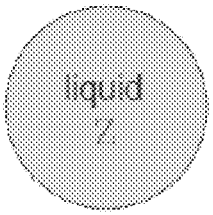 liquid | cannot reproduce positive node deviation |
| Bulk Elastic | 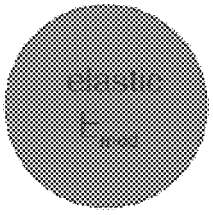 | can reproduce positive node deviation, but results in positive slope of isoelasticity line |
FIG. 21A

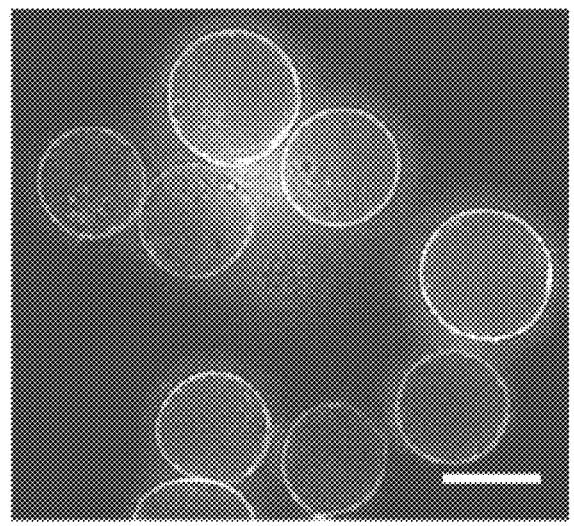
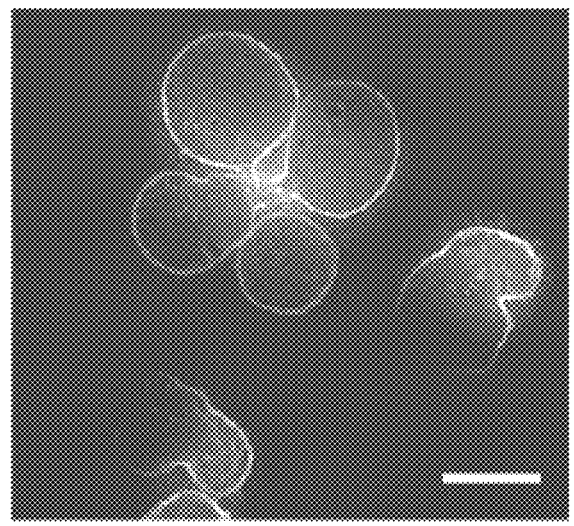
FIG. 23B

| Geometry | $\lambda(x)$ | integration interval | Description (used) |
|---|---|---|---|
| | $\pi r^2$ | $\left[-\frac{L}{2}, \frac{L}{2}\right]$ | cylinder parallel (hydrogels) |
| | $2L\sqrt{r^2 - x^2}$ | $[-r, r]$ | cylinder perpendicular (hydrogels) |
| | $\pi(r_s^2 - x^2)$ | $[-r_s, r_s]$ | sphere (singlet cells) |
| | $\begin{cases} \pi\left(r_f^2 - (x+d/2)^2\right), & x < 0 \\ \pi\left(r_f^2 - (x-d/2)^2\right), & x > 0 \end{cases}$ | $\left[-\frac{L}{2}, \frac{L}{2}\right]$ | overlapping spheres (during anaphase transition) |
| | $\begin{cases} \pi\left(r_d^2 - (x+r_d)^2\right), \text{if } x < 0 \\ \pi\left(r_d^2 - (x-r_d)^2\right), \text{if } x > 0 \end{cases}$ | $[-2r_d, 2r_d]$ | doublet parallel (after anaphase transition) |
| | $2\pi\left(r_d^2 - x^2\right)$ | $[-r_d, r_d]$ | doublet perpendicular (after anaphase transition) |
| | $\begin{cases} \pi r_1^2, \text{if } x < -q \\ \pi r_2^2, \text{if } x > q \\ A(r_1, r_2, d/2\sin\theta), \text{else} \end{cases}$ | $\left[-\frac{L}{2}\cos\theta, \frac{L}{2}\cos\theta\right]$ | doublet perpendicular (after anaphase transition) |

Note: $r_1 = \sqrt{r_f^2 - (x+q)^2}, r_2 = \sqrt{r_f^2 - (x-q)^2}, q = d/2\cos\theta$
$A(r_1, r_2, d)$ refers to the area of overlapping circles of radius $r_1$ and $r_2$, with their center separated by a distance of $d$

SYSTEMS AND METHODS FOR MEASURING PROPERTIES OF PARTICLES

RELATED APPLICATIONS

This application is a national stage filing under 35 U.S.C. § 371 of International PCT Application, PCT/US2018/037995, filed Jun. 18, 2018, and entitled "Systems and Methods for Measuring Properties of Particles", which claims priority under 35 U.S.C. § 119(e) to U.S. Provisional Patent Application No. 62/521,894, filed Jun. 19, 2017, and entitled "Systems and Methods for Measuring Properties of Particles", each of which is incorporated herein by reference in its entirety for all purposes.

FEDERALLY SPONSORED RESEARCH

This invention was made with government support under CA143874 awarded by the National Institutes of Health. The government has certain rights in the invention.

TECHNICAL FIELD

The present invention generally relates to systems and methods for measuring the properties (e.g., mechanical properties) of particles such as biological entities, in a fluidic channel.

SUMMARY

The present invention generally relates to systems and methods for measuring the properties of particles such as biological entities, in a fluidic channel.

In one aspect, methods for determining a property of a particle are provided. In some embodiments, the method comprises oscillating a suspended microchannel at a frequency within 10% of a resonant frequency of the suspended microchannel, flowing the particle in the suspended microchannel, and determining an acoustic scattering signal of the suspended microchannel while the particle flows through the suspended microchannel.

In some embodiments, the method comprises oscillating a suspended microchannel at a frequency within 10% of a resonant frequency of the suspended microchannel, flowing the plurality of particles through the suspended microchannel; and determining an acoustic scattering signal of the suspended microchannel for the plurality of particles flowing through the suspended microchannel.

In another aspect, systems are provided. In some embodiments, the system comprises a suspended microchannel, a detector configured to measure a determinable acoustic scattering signal when the particle is flowed in the suspended microchannel; and a controller configured to oscillate the suspended microchannel at a frequency of a mechanical resonant mode of the suspended microchannel, wherein the mechanical resonant mode comprises a node such that the acoustic scattering signal changes when the particle is present at the node.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 4C is COMSOL simulation of normalized z-velocity and vibration amplitude versus position of a particle for a suspended microchannel, according to one set of embodiments;

FIG. 4D is COMSOL simulation of normalized y-velocity amplitude versus position of a particle for a suspended microchannel, according to one set of embodiments;

FIG. 13F is a plot of node deviation versus particle volume from experiments and simulations with polystyrene beads, according to one set of embodiments;

FIG. 13G is a plot of node deviation versus aspect ratio from experiments with synthetic hydrogels of different shapes but same volume, according to one set of embodiments;

FIG. 16A is a plot of L1210 cell volume and SNAGS in mitosis, according to one set of embodiments;

FIG. 16B is a plot of buoyant mass and SNACS of a representative L1210 cell arrested in metaphase by treating with 5 μM S-trityl-cysteine (STLC) and the quantification of SNACS change with 5 μM STLC and 10 μM EIPA treatments, according to one set of embodiments;

FIG. 16C is the mean SNACS change of control and 10 μM ethylisopropylamiloride (EIPA, blue) treated L1210 cells in early mitosis, according to one set of embodiments;

FIG. 16D is an illustration of hypothetical cortical thinning scenario by shell expansion during swelling and a plot of SNACS of L1210 cells versus time before and after exposure to hypotonic stress, according to one set of embodiments;

FIG. 21A is a description of three other cell models used in simulation, according to one set of embodiments;

FIG. 23B shows representative images of actin cortex from live L1210 cells expressing LifeAct-RFP F-actin probe before (top) and after (bottom) Noc 1 μg/ml treatment, according to some embodiments;

FIG. 33 shows, in some embodiments, the mass distribution function ($\lambda(x)$) for selected geometries and orientations.

DETAILED DESCRIPTION

Systems and methods for measuring the properties (e.g., mechanical properties) of particles such as biological entities, in a fluidic channel(s) are generally provided. In some embodiments, the systems and methods comprise measuring an acoustic scattering of single particles. For example, a single particle (e.g., a biological entity) may be flowed in a suspended fluidic channel (e.g., a suspended microfluidic channel) and the fluidic channel is oscillated at or near a (mechanical) resonant frequency (e.g., at a second or higher bending mode) of the suspended fluidic channel. In some cases, an acoustic scattering signal (e.g., the change in resonant frequency of the fluidic channel as the particle flows along a longitudinal axis of the channel) may correspond to a property (e.g., a mechanical property, a cross-linking density, a transport rate of small molecules into/out of the particle) of the particle. In certain embodiments, the systems and methods comprise determining a node deviation due to a single particle (or node deviations for a plurality of particles). Without wishing to be bound by theory, in some cases, node deviation may be correlated with one or more properties (e.g., a mechanical property) of the particle. Nodes and node deviation are described in more detail below.

Such systems and methods may be particularly useful for measuring physical properties (e.g., mechanical properties such as stiffness and/or Young's elastic modulus, a cross-linking density, a transport rate of small molecules into/out of the particle) of single particles such as individual cells (e.g., bacteria, yeast, liquid tumor cells, solid tumor cells suspended in fluid, immune cells). Such systems and methods may also be useful for measuring physical properties of a pluralitys of cells.

In some embodiments, the particle is non-biological comprising a material such as a metal, polymer, ceramic, and/or glass. In certain embodiments, the particle is a polymer. Non-limiting examples of polymer particles that may be measured include polystyrene.

In some embodiments, the particle is a biological entity. Non-limiting examples of biological entities include virions, bacteria, protein complexes, exosomes, cells (e.g. cancer cells), or fungi (e.g., yeast). In some embodiments, the biological entity is obtained from a subject. A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. In an exemplary embodiment, the biological entity is a human cell. In some embodiments, the systems and methods described herein are useful for measuring the acoustic scattering of biological entities obtained from a subject for, for example, determining one or more physical properties of the biological entity, sorting, and/or diagnostic purposes.

Figure 1:
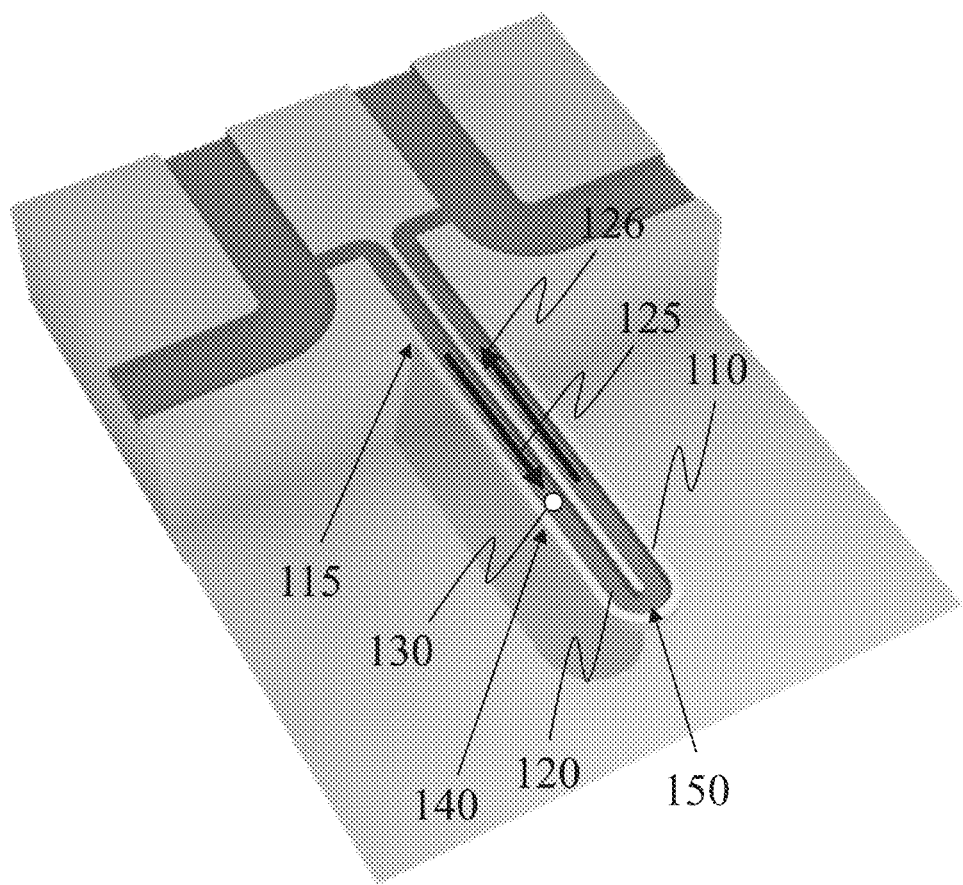
FIG. 1 is a schematic illustration of a system for determining a property of a particle, according to one set of embodiments.

For example, as illustrated in FIG. 1, system 100 comprises a suspended cantilever 110 (e.g., comprising fixed end 115) comprising a suspended fluidic channel 120. In some embodiments, suspended cantilever 110 may be oscillated (e.g., by transversely displacing fixed end 115) at a (mechanical) resonant frequency of suspended cantilever 110. In some cases, a particle 130 (e.g., a biological entity) may be flowed into fluidic channel 120. In some embodiments, an acoustic scattering signal may be measured as particle 130 flows in (micro)fluidic channel 120 (e.g., in the direction of arrow 125). In certain embodiments, the change in resonant frequency of suspended cantilever 110 may be determined as particle 130 flows along fluidic channel 120.

Figure 2A:
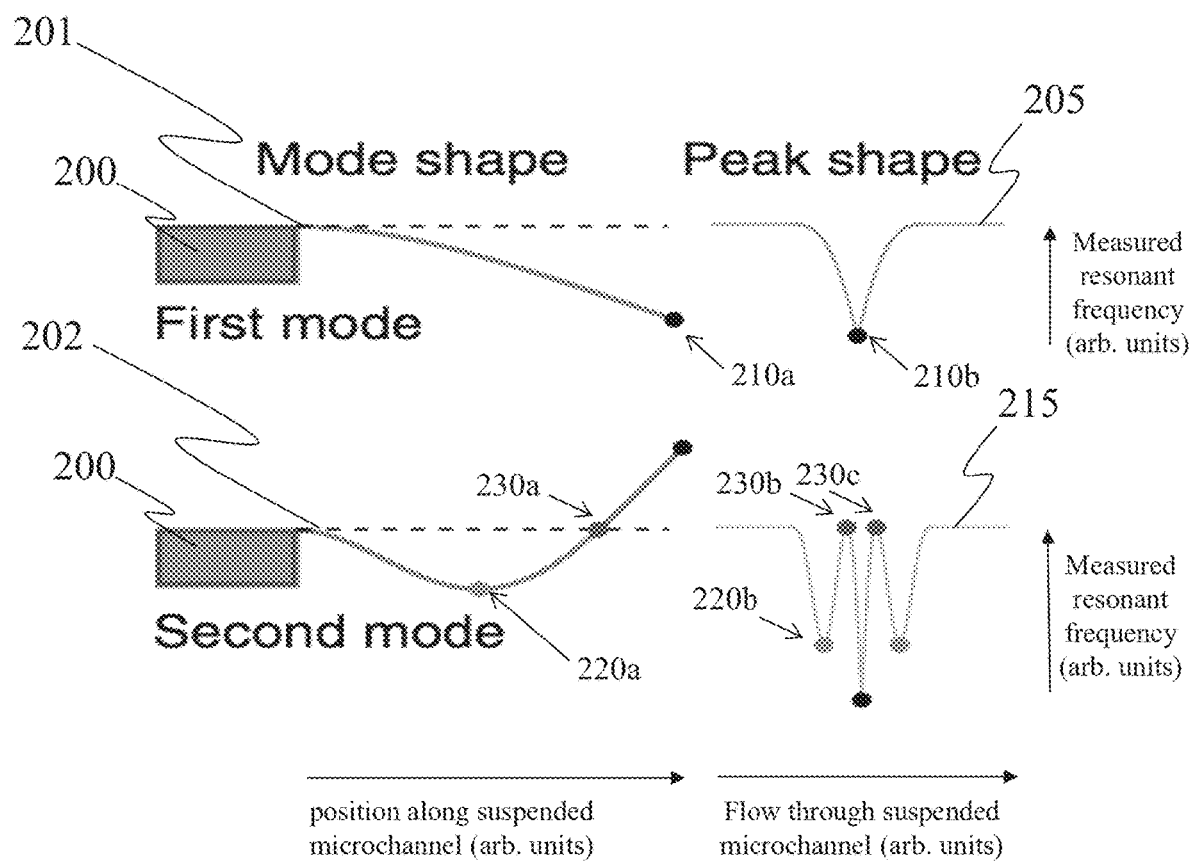
FIG. 2A is a schematic illustration of a first and second mode of oscillation and associated resonant peaks for a suspended microchannel having a particle flow through the microchannel, according to one set of embodiments.

In some embodiments, a node deviation of a single particle may be determined. The term node deviation, as used herein, refers to the difference between the resonant frequency of the suspended microchannel when a particle is present at a node of the suspended microchannel and the resonant frequency of the suspended microchannel when the particle is not present in the suspended microchannel. The term node, as used herein, is given its ordinary meaning in the art and generally refers to a position along the suspended microchannel in which no transverse or out-of-plane movement of the suspended microchannel is observed when the suspended microchannel is oscillated at a mechanical (bending) mode of the cantilever (or channel). For example, as illustrated schematically in FIG. 2A, suspended microchannel 200 may be oscillated, for example, such that the vibrational profile of the suspended microchannel 200 undergoes a first bending mode 201 (e.g., oscillated at a mechanical resonant mode with a first lowest frequency) such that a free end 210a of suspended microchannel 200 may oscillate. In certain embodiments, a particle (not shown) may be flowed along suspended microchannel 200 and the resonant frequency of the suspended microchannel may be measured as the particle travels along the suspended microchannel. In some cases, when the particle is traveling along the suspended microchannel 200, the resonant frequency of the first mode may changes creating a peak shape 205. In some cases when the particle is located at or passing through the free end 210a (under a first mode of oscillation), the suspended microchannel may have a resonant frequency 210b.

Figure 2B:
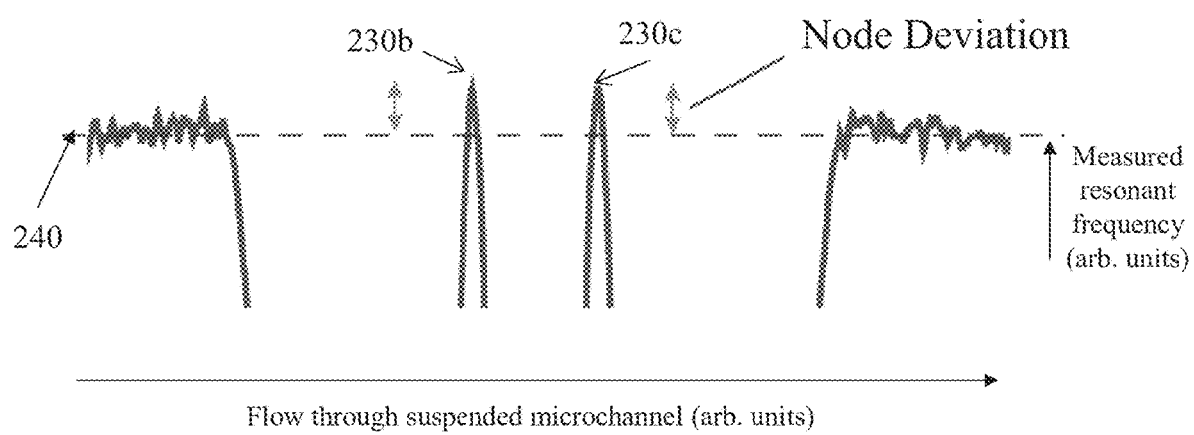
FIG. 2B is an exemplary plot of resonant frequency for a particle flowing through a suspended microchannel, according to one set of embodiments.

In some cases, suspended microchannel 200 may be oscillated at a second bending mode (e.g., oscillated at a mechanical out-of-plane resonant mode with a second lowest frequency) such that suspended microchannel 200 undergoes a second bending mode 202. In some such embodiments, oscillated suspended microchannel 200 may have a node position 230a, at which no transverse movement of the suspended microchannel occurs. In some cases, when a particle is traveling along the suspended microchannel 200, the resonant frequency of the second mode changes, creating a peak shape 215. In some embodiments as the particle travels through the suspended microchannel 200, it passes through the node 230a at least once (e.g., twice as particle 130 flows along direction 125 to tip 150 and as it flows along direction 126 away from tip 150 in FIG. 1). In some embodiments, a particle at position 230a may cause the suspended microchannel to have a resonant frequency 230b (and 230c, in some cases, if the particle travels back along the suspended microchannel). For example, as illustrated in FIG. 2B, resonant frequency 230b and/or 230c in the presence of the particle at the node (e.g., at position 230a in FIG. 2A) may be greater than the resonant frequency 240 of the suspended microchannel in the absence of the particle in the channel 120. In certain embodiments, the resonant frequency in the presence of the particle at the node 230b and 230c may be less than the resonant frequency 240 of the suspended microchannel in the absence of the particle in the channel 120.

Referring again to FIG. 1, in some cases, suspended microchannel 120 may be oscillated at a torsional mode, such that there is a node at the tip 150 and the particle flowing through the tip creates a deviation in the resonant frequency (e.g., a node deviation as shown in FIG. 2B).

The inventors unexpectedly discovered that the difference in the resonant frequency of the node of a suspended microchannel in the presence of the particle versus the absence of the particle (e.g., the node deviation) may be correlated with one or more properties (e.g., a mechanical property, a cross-linking density, a transport rate of small molecules into/out of the particle) of the particle, when the suspended microchannel is oscillated at a (bending or torsional) mode with at least one node location at its bending profile. The inventors also unexpectedly discovered that a node deviation may exist even when the density of the particle and the density of a fluid in which the particle is suspended are substantially equal (e.g., as compared to traditional theory which, without wishing to be bound by such theory, may suggest that no node deviation should exist because, for example, the net change in mass of the system at the node and throughout the channel is substantially zero).

Advantageously, the systems and methods described herein may permit the non-destructive determination of certain properties of a single particle(s) at relatively high throughput (e.g., greater than or equal to 1000 particles/hour). For example, in some embodiments, a suspended fluidic channel is oscillated (e.g., a fixed end of the suspended microchannel is driven at a frequency corresponding to a resonant frequency of the suspended microchannel with at least one node location in its bending profile). A particle may be flowed in the oscillating suspended microchannel and an acoustic scattering signal (e.g., a change in resonant frequency) at one or more nodes of the suspended microchannel may be determined. In some embodiments, the change in resonant frequency may correspond to one or more properties of the particle.

In some embodiments, a property of single particles in a plurality of particles may be determined at a rate of greater than or equal to 500 particles per hour, greater than or equal to 750 particles per hour, greater than or equal to 1000 particles per hour, greater than or equal to 1500 particles per hour, greater than or equal to 2000 particles per hour, greater than or equal to 2500 particles per hour, greater than or equal to 3000 particles per hour, greater than or equal to 4000 particles per hour, greater than or equal to 5000 particles per hour, or greater than or equal to 7500 particles per hour.

Figure 2C:
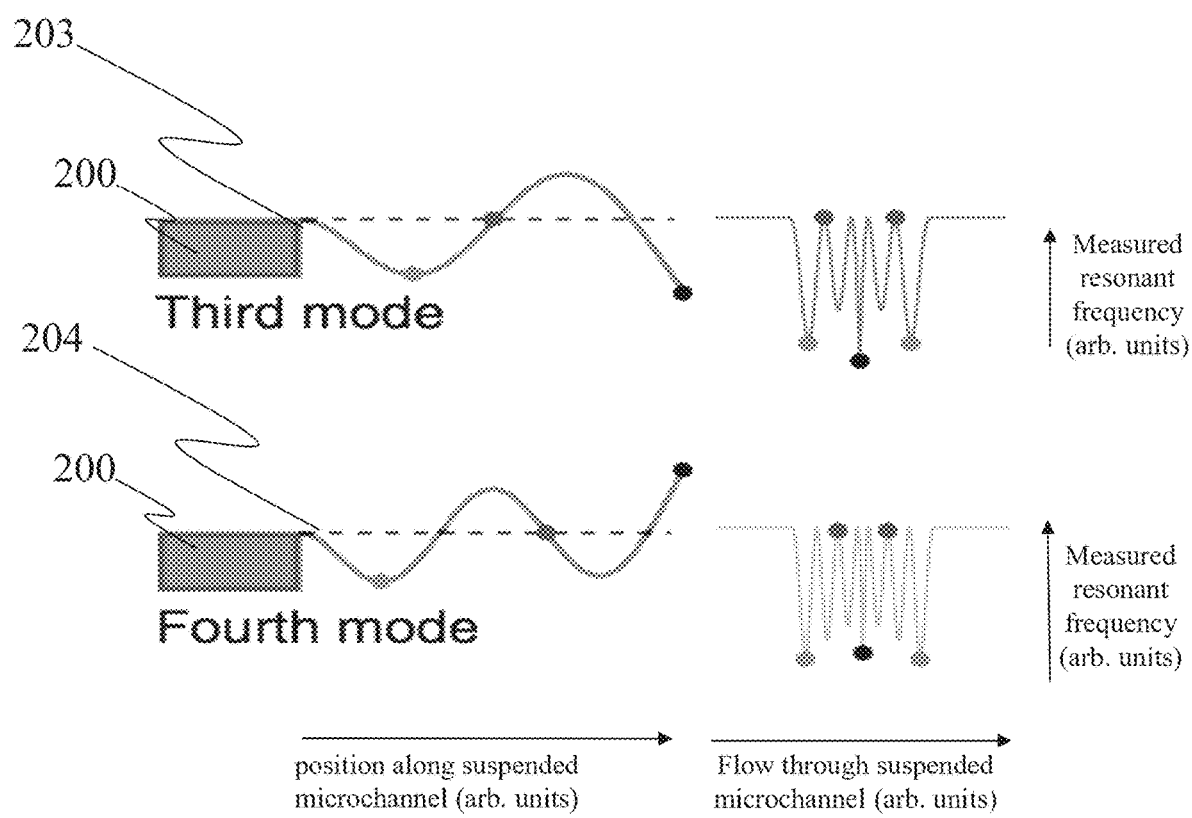
FIG. 2C is a schematic illustration of a third and fourth mode of oscillation and associated resonant peaks for a suspended microchannel having a particle flow through the microchannel, according to one set of embodiments.

In some embodiments, the suspended microchannel may be oscillated at second or higher order (bending) modes. For example, as illustrated in FIG. 2C, suspended microchannel 200 may be oscillated at a third (bending) mode 203, a forth (bending) mode 204, or greater. In some such embodiments, a node deviation may be determined for a single particle at one or more nodes of the oscillated suspended microchannel.

In some embodiments, the suspended microchannel may be oscillated at second or higher order (bending) modes simultaneously. In some such embodiments, a node deviation may be determined for a single particle at one or more nodes of one or more bending modes of the oscillated suspended microchannel.

In some embodiments, the acoustic scattering signal (e.g., comprising a node deviation) of a single particle may be determined by oscillating a suspended microchannel at a frequency within 10%, (e.g., within 5%, within 2%, within 1%, within 0.5%, within 0.1%, within 0.05%, within 0.01 wt %, within 0.005%, within 0.001%) of a resonant frequency (e.g., a first resonant frequency, a second resonant frequency mode, a third resonant frequency mode, a fourth resonant frequency mode) of the suspended microchannel and determining the acoustic scattering signal while flowing the particle in the suspended microchannel. In some cases, oscillating the suspended microchannel comprises oscillating at a frequency of a mechanical resonant mode comprising a node, as described above. In some embodiments, the node is located at a position on the suspended microchannel with substantially zero transverse motion (e.g., zero out-of-plane vibration) while the suspended microchannel is oscillated. In an exemplary embodiments, the acoustic scattering signal (e.g., comprising a node deviation) of a single particle is determined by oscillating a suspended microchannel at a frequency within 1% of a resonant frequency of the suspended microchannel and determining the acoustic scattering signal while flowing a particle (or plurality of particles) in the suspended microchannel.

In certain embodiments, determining the acoustic scattering signal comprises determining the resonant frequency (or change in resonant frequency) of the suspended microchannel when the particle is passing through and/or located at a node position. In certain embodiments, determining the acoustic scattering signal comprises determining the resonant frequency (or change in resonant frequency) of the suspended microchannel when the particle is kept at a node position. In some cases, determining the acoustic scattering signal comprises determining the node deviation caused by the particle. In some embodiments, the node deviation may be normalized (e.g., dividing the node deviation by the volume of the particle). The volume of the particle may be determined, for example, by weighing the particle in the suspended microchannel using two fluids with different densities. In some embodiments, the node deviation is normalized by a median volume (e.g., a median volume of a plurality of particles of the same type). Suitable methods for determining the volume of a single particle (or plurality of particles) is generally described in commonly-owned U.S. Pat. No. 8,087,284, entitled "Method And Apparatus For Measuring Particle Characteristics Through Mass Detection", issued Jan. 3, 2012, which is incorporated herein by reference in its entirety for all purposes.

In some embodiments, the system may comprise one or more components for oscillating the suspended microchannel and/or measuring the oscillation (and/or resonant frequency) of the suspended microchannel. For example, in some embodiments, the system comprises an actuator configured to vibrate (e.g., oscillate) the suspended microchannel (e.g., at a particular frequency and/or bending mode).

In certain embodiments, the system comprises a detector. The detector may be, in some embodiments, configured to determine the motion of the suspended microchannel.

In certain embodiments, the system may comprise a controller and/or microprocessor. In certain embodiments, the controller is configured (e.g., programmed) to receive and transmit data commands to/from one or more components of the system (e.g., the actuator, the detector, the suspended microchannel). In some embodiments, the data includes one or more signals from one or more detector. In some embodiments the controller and/or microprocessor is configured to determine the resonant frequency of the suspended microchannel. In some embodiments, the controller may be configured to adjust various parameters based on external metrics. For example, in certain embodiments, the controller is configured to adjust the oscillation frequency of the suspended microchannel in response to a signal from a user and/or a detector in electrical low frequency (e.g., of less than 1 particle per 10 seconds). In some cases, more than one particle may be flowed in the system such that only one particle occupies the suspended microchannel at any given time.

In some embodiments, a plurality of particles (e.g., a plurality of biological entities) are provided (e.g., suspended) in a fluid. As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. In a particular set of embodiments, the fluid is a liquid. In some embodiments, the fluid comprises water, blood, plasma, a reagent, a solvent, a buffer, a cell-growth medium, or combinations thereof. In certain embodiments, the particles are relatively soluble in the fluid.

In some embodiments, at least one pressure source may be associated with and/or in fluidic communication with the suspended microchannel (e.g., for flowing the particle(s) within the suspended microchannel. The pressure source may comprise any suitable means for providing pressure to a fluid disposed within microchannel. For example, in some embodiments, the pressure source may be a pump such as a syringe pump, a suction pump, a vacuum pump, a gas source, or any other suitable pressure source, (e.g., which may act like a source or a sink). In some embodiments, the pressure source may not be in direct fluidic communication with the suspended microchannel. That is to say, in certain embodiments, one or more intervening fluidic channel(s) or fluidic region(s) of the system may be present between the pressure source and the suspended microchannel.

In certain embodiments, the suspended microchannel may comprise one or more fluidic channels having a particular average cross-sectional dimension. The "cross-sectional dimension" (e.g., a width, a height, a radius) of the channel is measured perpendicular to the direction of fluid flow. In some embodiments, the average cross-sectional dimension of one or more fluidic channels is less than or equal to 2 mm, less than or equal to 1 mm, less than or equal to 800 microns, less than or equal to 600 microns, less than or equal to 500 microns, less than or equal to 400 microns, less than or equal to 300 microns, less than or equal to 200 microns, less than or equal to 100 microns, less than or equal to 50 microns, less than or equal to 25 microns, less than or equal to 20 microns, less than or equal to 15 microns, less than or equal to 10 microns, less than or equal to 5 microns, less than or equal to 2 microns, less than or equal to 1 micron, or less than or equal to 0.7 microns. In certain embodiments, the average cross-sectional dimension of the fluidic channel(s) is greater than or equal to 0.5 microns, greater than or equal to 0.7 microns, greater than or equal to 1 micron, greater than or equal to 5 microns, greater than or equal to 10 microns, greater than or equal to 15 microns, greater than or equal to 20 microns, greater than or equal to 25 microns, greater than or equal to 50 microns, greater than or equal to 100 microns, greater than or equal to 200 microns, greater than or equal to 300 microns, greater than or equal to 400 microns, greater than or equal to 500 microns, greater than or equal to 600 microns, greater than or equal to 800 microns, or greater than or equal to 1 mm. Combinations of the above-referenced ranges are also possible (e.g., greater than or equal to 1 micron and less than or equal to 2 mm, greater than or equal to 50 microns and less than or equal to 2 mm, greater than or equal to 50 microns and less than or equal to 100 microns, greater than or equal to 0.5 microns and less than or equal to 2 microns). Other ranges are also possible. In some embodiments, one or more channels may be a microfluidic channel. "Microfluidic channels" generally refer to channels having an average cross-sectional dimension of less than 1 mm.

In some embodiments, a single particle may flow in the microchannel at a particular average velocity (e.g., along a longitudinal axis of the microchannel). In certain embodiments, the average velocity of the particle(s) along the longitudinal axis of the microchannel is greater than or equal to 0.05 mm/second, greater than or equal to 0.1 mm/second, greater than or equal to 0.25 mm/second, greater than or equal to 0.5 mm/second, greater than or equal to 0.75 mm/second, greater than or equal to 1 mm/second, greater than or equal to 2 mm/second, greater than or equal to 3 mm/second, greater than or equal to 4 mm/second, greater than or equal to 5 mm/second, greater than or equal to 6 mm/second, greater than or equal to 7 mm/second, greater than or equal to 8 mm/second, or greater than or equal to 9 mm/second. In some embodiments, the average velocity of the particles along the longitudinal axis of the microchannel is less than or equal to 10 mm/second, less than or equal to 9 mm/second, less than or equal to 8 mm/second, less than or equal to 7 mm/second, less than or equal to 6 mm/second, less than or equal to 5 mm/second, less than or equal to 4 mm/second, less than or equal to 3 mm/second, less than or equal to 2 mm/second, less than or equal to 1 mm/second, less than or equal to 0.75 mm/second, less than or equal to 0.5 mm/second, or less than or equal to 0.25 mm/second. Combinations of the above-referenced ranges are also possible (e.g., greater than or equal to 0.05 mm/second and less than or equal to 10 mm/second). Other ranges are also possible.

In embodiments in which the system comprises one or more suspended microchannel resonators (e.g., comprising a suspended microchannel), the suspended microchannel resonator may have one or more characteristics described in commonly-owned U.S. Pat. No. 7,387,889, entitled "Measurement of concentrations and binding energetics", issued Jun. 17, 2008; commonly-owned U.S. Pat. No. 7,838,284, entitled "Measurement of concentrations and binding energetics", issued Nov. 23, 2010; commonly-owned U.S. Pat. No. 9,134,294, entitled "Method And Apparatus For High Throughput Diagnosis Of Diseased Cells With Microchannel Devices", issued Sep. 15, 2015; commonly-owned U.S. Pat. No. 9,134,295, entitled "Serial Arrays of Suspended Microchannel Resonators", issued Sep. 15, 2015; commonly-owned U.S. Pat. No. 8,087,284, entitled "Method And Apparatus For Measuring Particle Characteristics Through Mass Detection", issued Jan. 3, 2012; commonly-owned U.S. Pat. No. 8,722,419, entitled "Flow cytometry Methods And Immunodiagnostics With Mass Sensitive Readout", issued May 13, 2014; commonly-owned U.S. patent application Ser. No. 14/924,531, entitled "Simultaneous oscillation and frequency tracking of multiple resonances via digitally implemented phase-locked loop array", filed Oct. 27, 2015; each of which is incorporated herein by reference in its entirety for all purposes.

In some cases, a reference particle is not flowed in the suspended microchannel in order to determine the property of the single particle. For example, in a particular set of embodiments, a property of a single particle may be determined by comparing the acoustic scattering signal in the presence of a single particle to an acoustic scattering signal of a reference particle (e.g., with a known value of the property). However, in some embodiments, the property of the single particle may be determined without the use (e.g., flowing in the suspended microchannel) of such a reference particle. For example, the property of the single particle may be determined, in some cases, by determining the node deviation by said particle.

Fluids can be introduced (e.g., transport, flowed, displaced) into the system (or a fluidic channel therein (e.g., the microchannel)) using any suitable component, for example, a pump, syringe, pressurized vessel, or any other source of pressure. Alternatively, fluids can be pulled into the fluidic channel by application of vacuum or reduced pressure on a downstream side of the channel or device. Vacuum may be provided by any source capable of providing a lower pressure condition than exists upstream of the channel or device. Such sources may include vacuum pumps, venturis, syringes and evacuated containers. It should be understood, however, that in certain embodiments, methods described herein can be performed with a changing pressure drop across a fluidic channel by using capillary flow, the use of valves, or other external controls that vary pressure and/or flow rate.

Microchannel of the system (e.g., the microchannel) may have any suitable cross-sectional shape (e.g., circular, oval, triangular, irregular, trapezoidal, square or rectangular, serpentine, u-shaped, or the like). A fluidic channel may also have an aspect ratio (length to average cross sectional dimension) of at least 2:1, more typically at least 3:1, 5:1, or 10:1 or more. A fluid within the fluidic channel may partially or completely fill the fluidic channel.

In some embodiments, the microchannel may have a particular configuration. In certain embodiments, at least a portion of the microchannel may be substantially linear in the direction of fluid flow. In some embodiments, at least a portion of the microchannel may be curved, bent, serpentine, staggered, zig-zag, spiral, or combinations thereof. Advantageously, the use of a non-linear fluidic channels may permit the incorporation of two or more suspended microchannel resonators into the system (e.g., such that a plurality of particles may be measured in parallel, such that a change in a property of a single particle may be determined e.g., in series).

The system or portions thereof (e.g., a suspended microchannel) described herein can be fabricated of any suitable material. Non-limiting examples of materials include polymers (e.g., polypropylene, polyethylene, polystyrene, poly(acrylonitrile, butadiene, styrene), poly(styrene-co-acrylate), poly(methyl methacrylate), polycarbonate, polyester, poly(dimethylsiloxane), PVC, PTFE, PET, or blends of two or more such polymers), adhesives, and/or metals including nickel, copper, stainless steel, bulk metallic glass, or other metals or alloys, or ceramics including glass, quartz, silica, alumina, zirconia, tungsten carbide, silicon carbide, or non-metallic materials such as graphite, silicon, or others.

In some embodiments, the fluid or system is maintained under physiological conditions (e.g., for measuring cell growth). For example, in some embodiments, the fluid and/or the system is maintained at 37° C. and, optionally, pressurized with a 5% carbon dioxide gas mixture (e.g., to maintain pH stability of the growth media).

In some embodiments, an acoustic scattering signal and/or a property of a biological entity such as a living cell (e.g., mammalian cell, a bacteria) may be determined. In some embodiments, the particle (e.g., a biological entity) may be stimulated (e.g., treated with a chemical and/or biological reagent such as a drug) and the change in acoustic scattering signal may be determined by measuring the difference in the acoustic scattering signal before and after the stimulation (e.g., the difference in node deviation before and after stimulation). In an exemplary embodiment, the property (e.g., the property correlated with the acoustic scattering signal) is a thickness of a cell wall of the biological entity, a change in cell cycle of the biological entity, a mechanical property such as stiffness or Young's elastic modulus, of the biological entity, or combinations thereof.

As used herein, the term "drug" refers to an agent that is administered to a subject to treat a disease, disorder, or other clinically recognized condition, or for prophylactic purposes, and has a clinically significant effect on the body of the subject to treat and/or prevent the disease, disorder, or condition. A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Drugs include, without limitation, agents listed in the United States Pharmacopeia (USP), Goodman and Gilman's The Pharmacological Basis of Therapeutics, 10th edition, McGraw Hill, 2001; Katzung, B. (editor), Basic and Clinical Pharmacology, McGraw-Hill/Appleton & Lange, 8th edition (Sep. 21, 2000); Physician's Desk Reference (Thomson Publishing); and/or The Merck Manual of Diagnosis and Therapy, 17th edition (1999), or the 18th edition (2006) following its publication, Mark H. Beers and Robert Berkow (editors), Merck Publishing Group, or, in the case of animals, The Merck Veterinary Manual, 9th edition, Kahn, C. A. (ed.), Merck Publishing Group, 2005. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In an exemplary embodiment, the drug is an antibiotic. In another exemplary embodiment, the drug is an actin-modifying drug (e.g., latrunculin B (LatB)). In yet another exemplary embodiment, the drug is a cancer drug (e.g., for the treatment of cancer).

EXAMPLES

The following examples are intended to illustrate certain embodiments described herein, including certain aspects of the present invention, but do not exemplify the full scope of the invention.

Example 1—Theory

The following example describes theory, simulation, correcting mass distribution, orientation dependent noise, swelling driven cortical expansion, and further discussion.

Figure 3A:
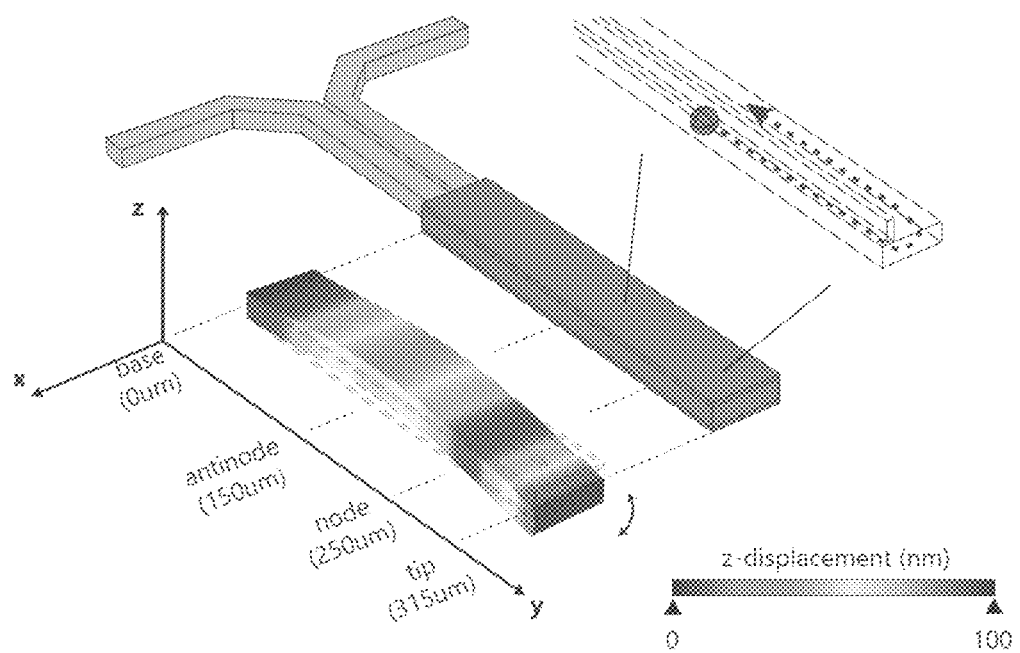
FIG. 3A is a plot of the z-displacement for an oscillating suspended microchannel, according to one set of embodiments.
Figure 3B:
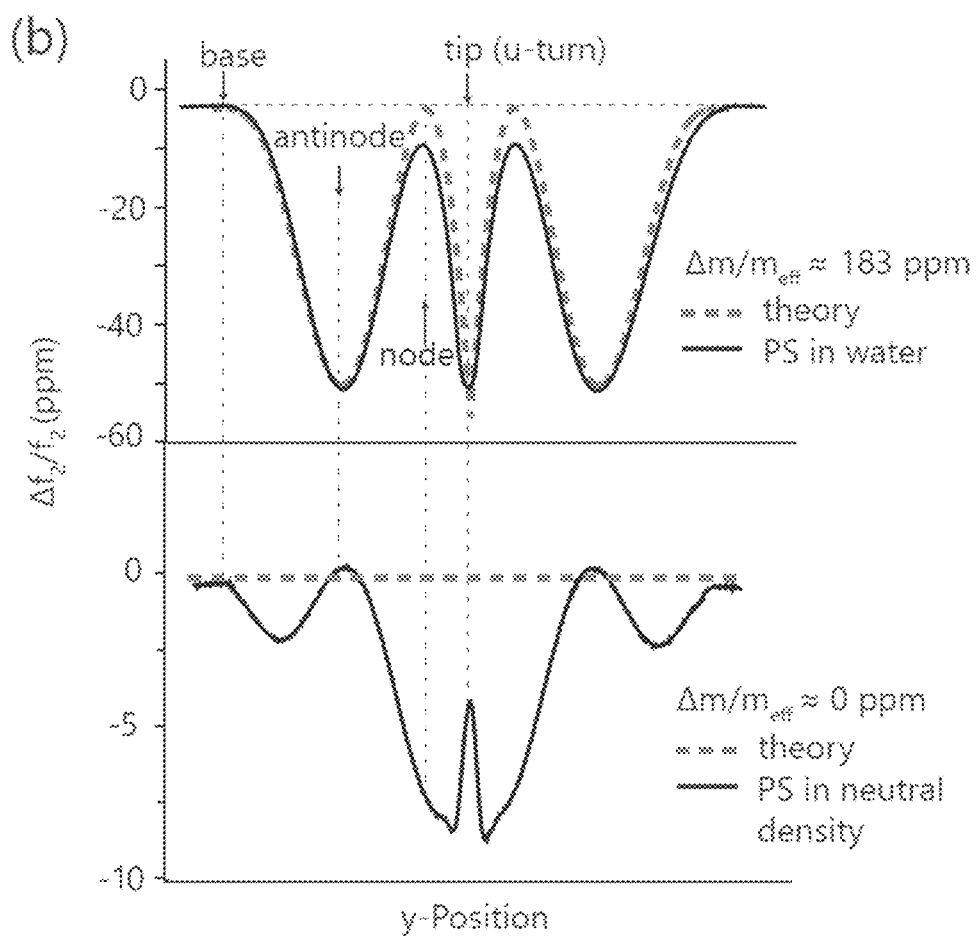
FIG. 3B is a plot of the change in resonant frequency versus y-position of a particle for a suspend microchannel, according to one set of embodiments.

Using the Rayleigh Ritz Theorem, which equates time average kinetic energy and time averaged potential energy, resonant frequency of the suspended microchannel resonator (SMR) containing a particle immersed in the fluidic channel can be obtained. Generally, and without wishing to be bound by theory, when a particle flows through the embedded fluidic channel of a vibrating cantilever, resonant frequency may shifts as a function of particle position and may be described by the equation:

$$\left(\frac{\Delta f_n}{f_n}\right) = -1 + \left[1 + u_n(y)^2 \frac{\Delta m}{m_{\text{eff}}}\right]^{-1/2} \approx \frac{1}{2} u_n(y)^2 \frac{\Delta m}{m_{\text{eff}}} \quad (1)$$

where $f_n$ is the resonant frequency, $u_n(y)$ is the normalized transverse displacement of an Euler beam vibrating at nth flexural bending mode, and $\Delta m$ is the change in mass of the system (e.g., for second bending mode, see FIGS. 3A-3B).

However, above equation does not explain the change in resonant frequency upon loading a particle of neutral density ($\Delta m=0$); For example, flowing a polystyrene bead (pp 1.05 g/cm3) through the suspended microchannel resonator (SMR) filled with fluid of the same density ($\rho f \approx 1.05$ g/cm3) produces distinct, non-zero shift in resonant frequency (FIG. 3B, bottom). Moreover, the theory predicts the frequency shift to be precisely zero when particle is at a node (e.g., y, where $u_2(y)=0$) regardless of fluid density and $\Delta m$.

From the Euler-Bernoili beam equation, time dependent displacement of a cantilever (e.g., a suspended microchannel) vibrating in 2nd at angular frequency ω is generally given by:

$$z(y,t) = A u_2(y) \cos(\omega t) \quad (2)$$

where $u_2$ is the normalized 2nd eigenmode solution to Euler-Bernouili beam equation and A is the tip oscillation amplitude. Taking only first-order perturbations into account, total energy of the cantilever can be written as, $$E = C(y,\omega)\cos^2(\omega t) + D(y,\omega)\sin^2(\omega t) + \text{Constants} \quad (3)$$

where the coefficient C and D is a function of the particle position. Higher order perturbations can be generally neglected because energy terms affecting resonant frequency may have square amplitude dependence, and thus the effect of amplitude effectively cancels out. The equation can be re-written as:

$$E = \{C_0 + \Delta C(y)\}\cos^2(\omega t) + \{\alpha\omega^2 + \Delta D(y)\}\sin^2(\omega t) + \text{Constants}$$

Using principle of Energy Conservation, two terms $C(y, \omega) = D(y, \omega)$ can be equated and then solve for ω. Explicitly writing out, $$\frac{\Delta\omega}{\omega} = -1 + \left[1 + \frac{\Delta D(y) - \Delta C(y)}{2C_0}\right]^{1/2} \approx \frac{(\Delta D(y) - \Delta C(y))}{C_0} \quad (4)$$

where last approximation holds generally true when $\Delta D$ and $\Delta C$ is small compared to $C_0$. In the case of ideal cantilever loaded with point mass follows, $$C(y) = U_{max} = A^2 \int_0^l \frac{1}{2} EI \left(\frac{\partial u}{\partial y}\right)^2 dy \equiv C_0$$

$$D(y,\omega) = T_{max} = A^2 \left[\int_{Si} \frac{1}{2}\rho_{Si}\omega^2 u_2^2 dV + \int_F \frac{1}{2}\rho_p \omega^2 u_2^2 dV + \frac{1}{2} m_p \omega^2 u_2(y)^2\right]$$

$$= \alpha\omega^2 + \frac{1}{2}A^2 \Delta m \omega^2 u_2(y)^2$$

(5)

Kinetic energy terms listed are silicon kinetic energy, fluid kinetic energy, and particle kinetic energy, respectively. Plugging in $C_0 = \alpha\omega^2$ and defining $$\alpha = \tfrac{1}{2} m_{eff} A^2 u_2(y)^2, \quad (6)$$

equation (1) may be obtained. However, in ideal cantilever case discussed above, the following was assumed: First, vibrating fluid particle is completely incompressible and thus possess no potential energy. Second, any fluid-particle interaction was neglected and assumed the motion to follow the vibration of cantilever (e.g., silicon layers). Third, only transverse (z-direction) motion was considered, neglecting y-direction or x-directional motion and thus their contribution to the total kinetic energy.

Then, applying Rayleigh-Ritz Theorem to equate $\tfrac{1}{2}U_{max}$ and $\tfrac{1}{2}T_{max}$ at non-zero and using Eq. (5), $$\tfrac{1}{2}A^2\omega_0^2 = \tfrac{1}{2}A^2(\omega_0+\Delta\omega)^2(m_{eff}+\Delta m u^2(y)) \quad (7)$$

where $\Delta m = m_p - m_f$ and $\omega = \omega_0 + \Delta\omega$. This then simplifies to Eq. (1), $$\left(1 + \frac{\Delta\omega}{\omega_0}\right)^{-2} = 1 + u^2(y)\frac{\Delta m}{m_{eff}} \quad (8)$$

Figure 13A:
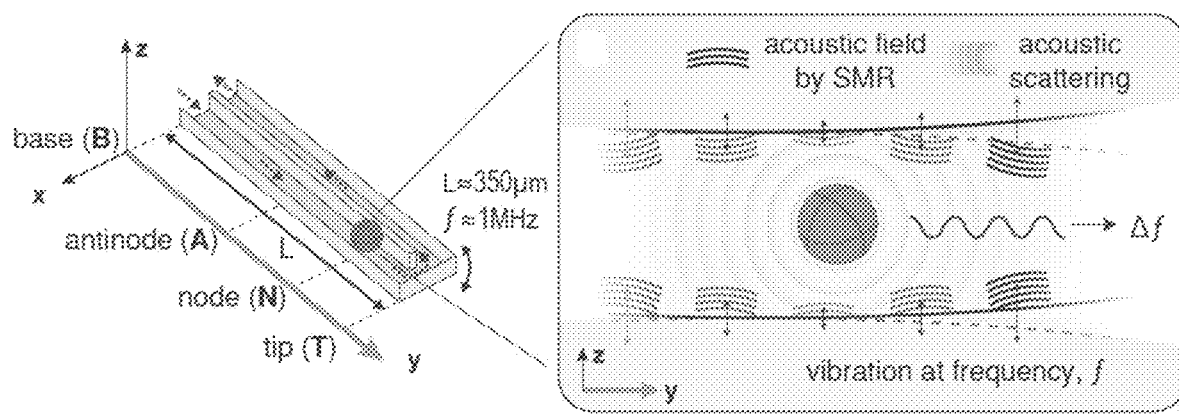
FIG. 13A is a schematic of SMR with a particle flowing through the embedded microfluidic channel, according to one set of embodiments.
Figure 13B:
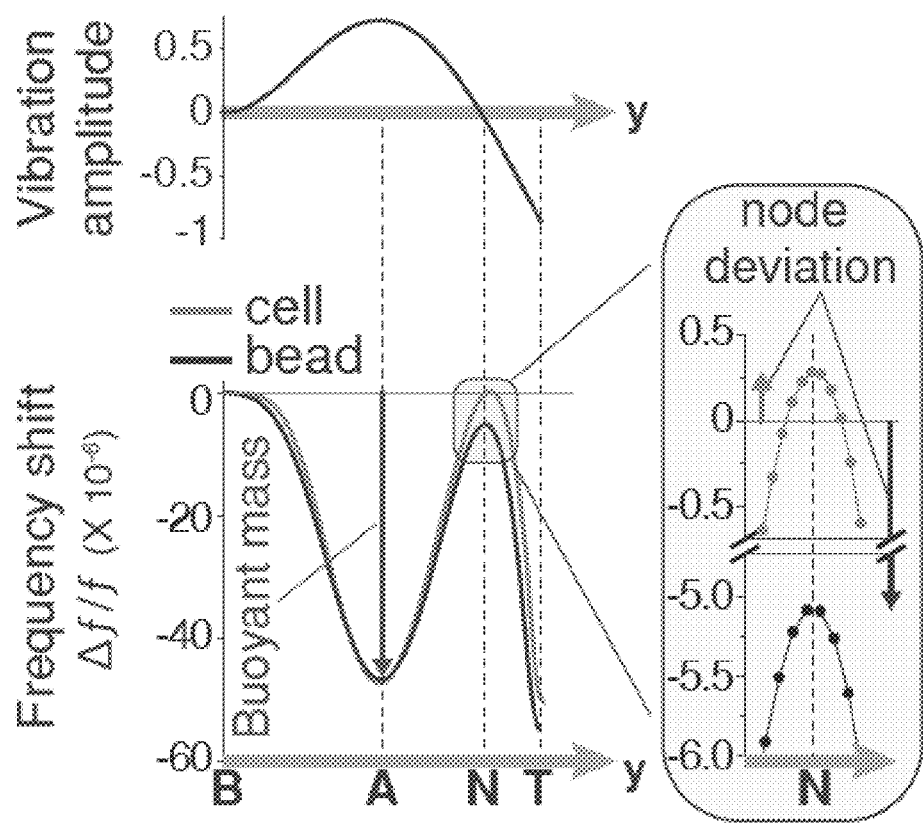
FIG. 13B is a conceptual illustration of frequency shift due to acoustic scattering, according to one set of embodiments.
Figure 13C:
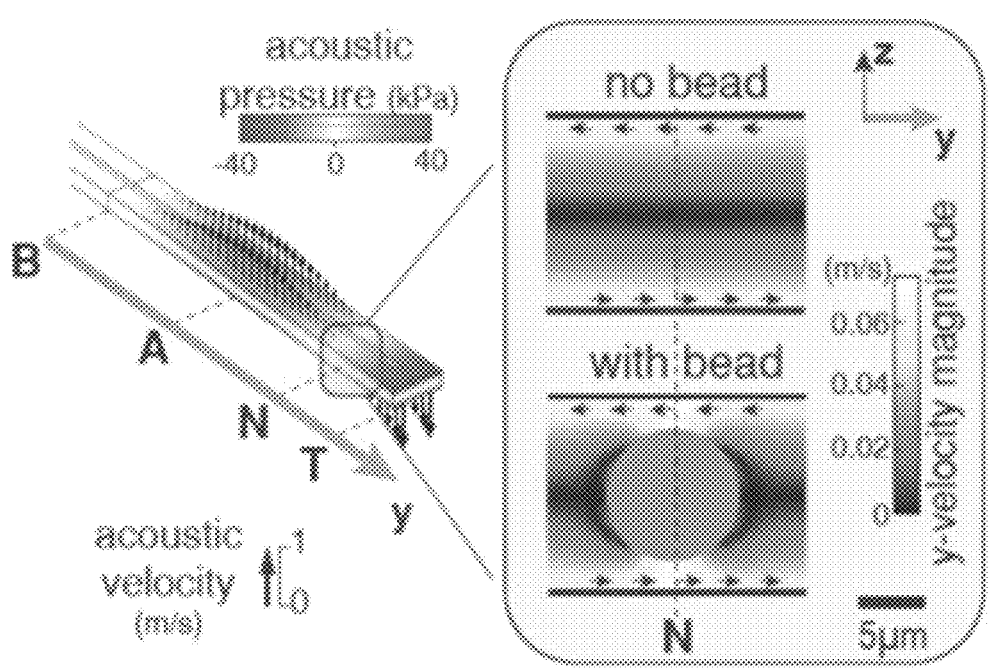
FIG. 13C is a schematic of acoustic pressure and acoustic velocities (arrows) within SMR from Finite Element Method simulations, according to one set of embodiments.
Figure 13D:
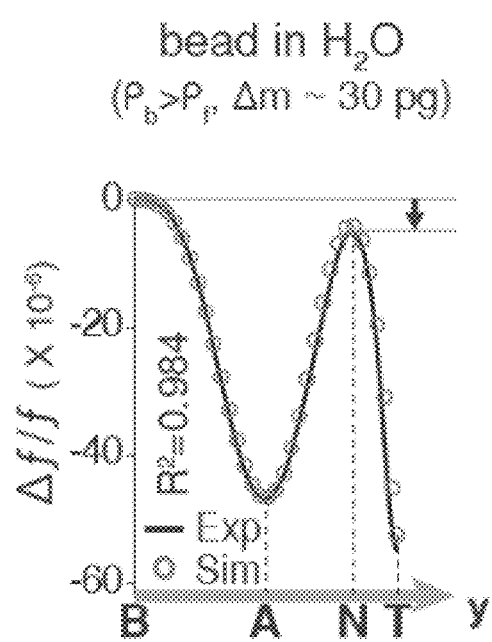
FIG. 13D is a plot of $\Delta f/f$ from simulations and experiments with polystyrene beads flowing through SMR filled with $H_2O$, according to one set of embodiments.

So far, it has been described how energy balance between kinetic and potential energy of the system collectively changes the resonant frequency of SMR. However, acoustic features in the SMR were ignored and several energy terms associated with acoustic fields in the SMR were neglected. First, it was assumed that the only term contributing to the potential energy is from the silicon layer. However, the potential energy stored in acoustic standing waves (FIG. 4B) in the embedded microfluidic channel, as well as the energy stored in the elastic materials (particle and shell of the cell model) should also be included. Second, only considered velocities in the z-direction were considered (i.e., normal to the surface of the cantilever, FIG. 4C). It was determined that the velocities along the cantilever (y-direction) could be as large as 10% that of the z-direction at some locations (FIG. 4D). Third, and most importantly, interaction between the particle and fluid environment were neglected by assuming the particle and nearby fluid have the same kinetics. However, as the particle scatters the acoustic field, it alters the kinetics of the neighboring fluid medium as well (FIG. 13C). By incorporating these three considerations into the FEM model, the simulation results match the experimental results (FIG. 13D, FIG. 13E and FIG. 5B, FIG. 5C, and FIG. 6A).

To develop a more general theory that includes the effect of the acoustic field, the governing equations for the fluids and their acoustic energies were evaluated. Kinetics of a fluid is determined by its density, ρ, pressure p, and individual fluid particle velocity v. These parameters are governed by the continuity equation for the mass and the Navier-Stokes equation. Acoustic fields that result from a perturbation to these parameters can be written in terms of the zeroth, first, second, and third and higher-order terms as:

$$\rho = \rho_0 + \rho_1 + \rho_2 + \ldots$$

$$p = p_0 + p_1 + p_2 + \ldots$$

$$\vec{v} = \vec{v}_0 + \vec{v}_1 + \vec{v}_2 + \ldots \quad (9)$$

where the subscripts denotes the order of perturbation. Zeroeth order represents the quiescent state, and for simplicity, $v_0 = 0$.

Taking only the first order perturbations into account and neglecting $2^{nd}$ and higher order terms, the governing equations for fluids can be simplified into a wave equation $$\nabla^2 p_1 = \frac{1}{c_0^2}\frac{\partial^2 p_1}{\partial t^2} \quad (10)$$

where $c_0$ is the speed of sound in the fluid, and $p_1 = c_0^2 \rho_1$. Assuming time-harmonic fields, $$\rho_1(\vec{r}\cdot t) = R\{\tilde{\rho}_1(\vec{r})e^{-i\omega t}\}$$

$$p_1(\vec{r}\cdot t) = R\{\tilde{p}_1(\vec{r})e^{-i\omega t}\}$$

$$\vec{v}_1(\vec{r}\cdot t) = R\{\vec{\tilde{v}}_1(\vec{r})e^{-i\omega t}\}$$

Eq. (10) reduces to a Helmholtz equation, given by $$\nabla^2 p_1 - \frac{\omega^2}{c_0^2} p_1 = 0 \tag{12}$$

Figure 17:
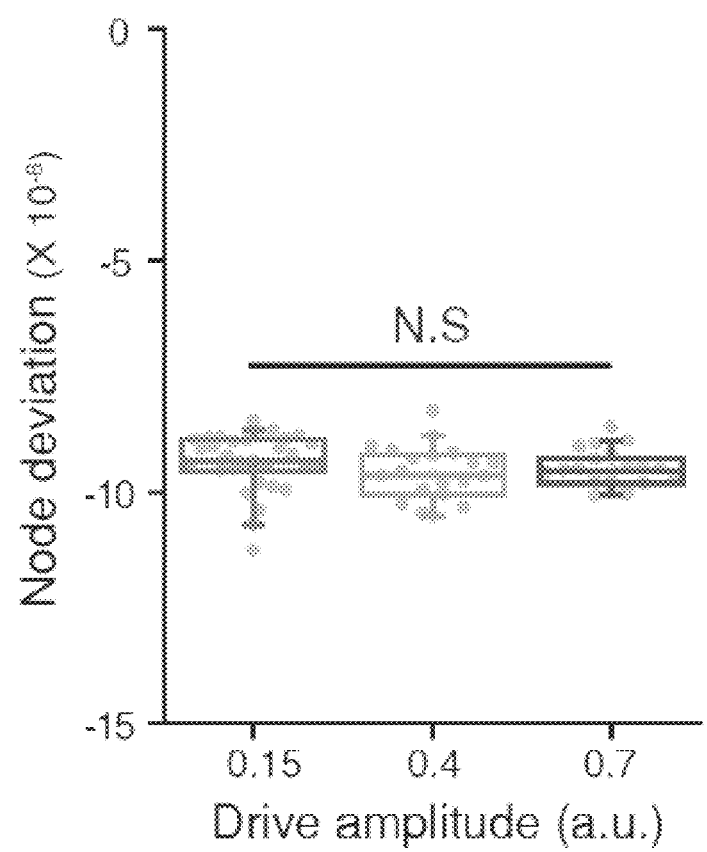
FIG. 17 is node deviation of 10 μm polystyrene beads measured by SMR vibrating in different amplitudes, according to one set of embodiments.
Figure 18:
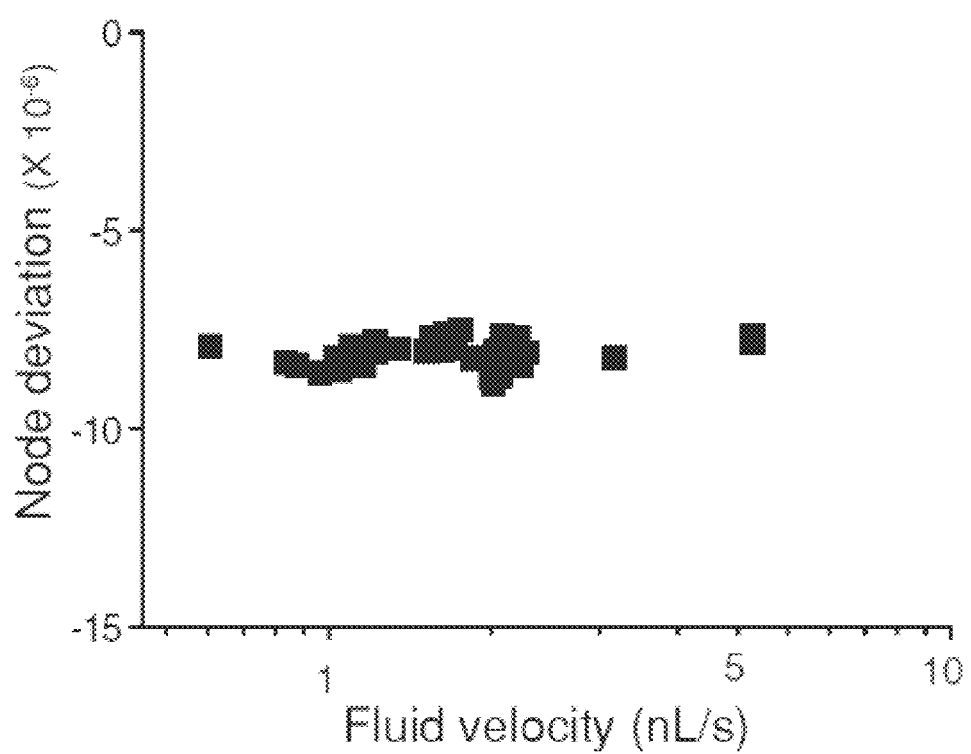
FIG. 18 is node deviation of 10 μm polystyrene beads measured by SMR with different fluid velocities, according to some embodiments.

It is worth noting that the harmonic vibration of the cantilever is the only necessary source for the acoustic perturbation. Since the equation governing the first order density $\rho_1$, pressure $p_1$ and fluid velocity field $v_1$ is linear, all first order parameters will be proportional to A. Therefore, the kinetic and potential energy terms from the first-order acoustic fields, $$w_v = \frac{1}{2}\rho_0 v_1^2 \tag{13}$$

$$w_p = \frac{1}{2}\frac{p_1^2}{\rho_0 c_0^2}$$

will have $\sin^2(\omega t)$ or $\cos^2(\omega t)$ dependence as well as $A^2$, similar to the energy terms shown in Table 2. Therefore, when equating the total kinetic energy and potential energy (Rayleigh Ritz Theorem) to obtain the resonant frequency of the system, terms with $A^2$ effectively cancels out. In fact, amplitude does not affect the node deviation signal experimentally (FIG. 17 and FIG. 18). It is clear that since $p_1$ is in-phase with the cantilever vibration ($\propto \cos(\omega t)$, FIG. 4B), $\omega_p \propto \cos^2(\omega t)$ and will therefore contribute to the potential energy of the system, as expected. On the other hand, $v_1$ is out-of-phase with the cantilever movement ($\propto \sin(\omega t)$, FIG. 4C and FIG. 4D), $\omega_v \propto \sin^2(\omega t)$ and will contribute to the total kinetic energy of the system.

TABLE 2

List of energy terms.

| Parameter | Equation | Description |
|---|---|---|
| $U_f$ | $\int_f \left[\frac{p_1^2}{2\rho c^2}\right] dV$ | acoustic potential energy |
| $T_f$ | $\int_f \left[\frac{1}{2}\rho v_1^2\right] dV$ | acoustic kinetic energy |
| $U_{p,s}$ | $\int_{p,s} \left[\frac{1}{2}\sigma_{ij}\epsilon_{ij}\right]$ | particle (shell) stored elastic \potiential energy |
| $T_{p,s}$ | $\int_{p,s} \left[\frac{1}{2}\rho x^2 \omega^2\right]$ | particle (shell) kinetic energy |
| $U_c$ | $\int_c \left[\frac{p_1^2}{2\rho c^2}\right] dV$ | liquid core acoustic potential energy (only applies to the cell model) |

TABLE 2-continued

List of energy terms.

| Parameter | Equation | Description |
|---|---|---|
| $T_c$ | $\int_c \left[\frac{1}{2}\rho v_1^2\right] dV$ | liquid core acoustic kinetic energy (only applies to the cell model) |

The fluid-particle interaction, where a particle scatters the acoustic field around it, causes nearby fluid velocity and pressure to be:

$$\vec{v}_1 = \vec{v}_{in} + \vec{v}_{sc}$$

$$p_1 + p_{in} + p_{sc} \tag{14}$$

where $\vec{v}_{in}$ and $p_{in}$ are incident acoustic terms and $\vec{v}_{sc}$ and $p_{sc}$ are scattered terms. This will cause not only the acoustic fields to be scattered but the particle in the acoustic field to experience a first order force:

$$\vec{F}_1 = -\int_{\partial\Omega} p_1 \dot{u} dS \tag{15}$$

which disturbs the motion of the particle and therefore its kinetic energy, $T_p$, as well as stored elastic potential energy, $U_p$ due to finite deformation caused by movement of the surrounding fluid.

All acoustic energy terms were incorporated, including those resulting from fluid-particle interactions in to Eq., (3) and Eq. (4), in order to derive the resonant frequency change of the SMR:

$$U_{total} = U_{sil} + U_f + U_p \tag{16}$$

$$T_{total} = T_{sil} + T_f + T_p$$

where $U_f$ and $U_p$ denotes acoustic potential energy and stored elastic energy of the particle, respectively. For sufficiently small changes in the frequency ($\Delta\omega \ll \omega_0$), $$U_{total} = U_0 + \Delta U(y) \tag{17}$$

$$T_{total} = \alpha(\omega_0 + \Delta\omega)^2 + \Delta T(y)$$

where $U_0$ and $T_0 = \alpha\omega_0^2$ are the time-averaged potential and kinetic energy of the system without the particle immersed in the SMR (i.e., y=0), respectively. $\Delta U(y)$ and $\Delta T(y)$ refer to change in potential and kinetic energy of fluids and particles, respectively, as a function of the particle position, y.

Applying the Rayleigh Ritz Theorem leads to:

$$\frac{\Delta\omega}{\omega_0} = -1 + \left[1 - \frac{\Delta T(y) - \Delta U(y)}{U_0}\right]^{1/2} \approx \frac{\Delta U(y) - \Delta T(y)}{2U_0} \tag{18}$$

Eq. (18) generalizes the resonant frequency change of the system upon particle loading to be dependent on the total potential and kinetic energy of the system, unlike in Eq. (1), where frequency only depends on the particle position and mass. It is clear from Eq. (18) that even when a particle is located at the node with zero net out-of-plane motion, the disruption of the acoustic field would still result in a non-zero frequency shift.

The simulation results shown in FIG. 4D and FIG. 4E and FIG. 5B, FIG. 5C, and FIG. 6A were computed using the Eq. (18). This was accomplished by first numerically solving the Helmholtz equation (Eq. (12)) to obtain three fluid parameters (i.e., ρ, v, p), while varying the position of the particle along the channel. Then, the kinetic energy and potential energy of the system were obtained for each position (Table 2), and the corresponding energy was subtracted without the particle to get the term, ΔU(y)−ΔT(y).

When the acoustic domain of interest has non-trivial geometry with complicated boundary conditions, solving the governing equations analytically is challenging. Therefore Finite Element Method (FEM) simulations were utilized to solve the relevant equations. For FEM analysis, the governing equation (i.e., Wave equation: Eq. (10) for the time domain; Helmholtz equation: Eq. (12) for frequency domain) is to numerically solve for each individual 'block' within a mesh.

Figure 4A:
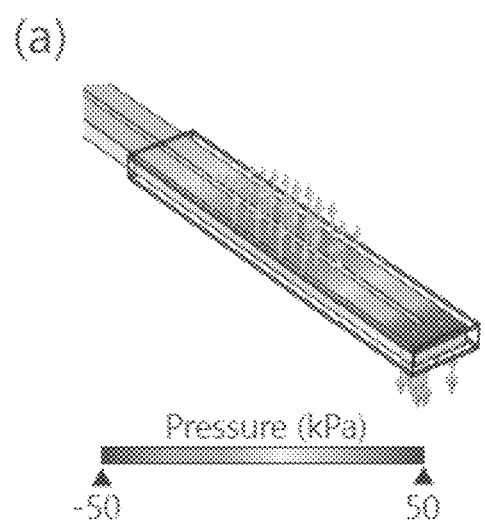
FIG. 4A is COMSOL simulation of fluid velocity and pressure of a suspended microchannel, according to one set of embodiments.

For FEM analysis, COMSOL Multiphysics software 4.3 was used. The exact geometry of the SMR used for experiments in this work was reproduced in the software implementing the CAD design of SMR (FIG. 4A and Table 1). A particle was embedded in the detection regime of the cantilever (i.e., buried channel which is covered with thin silicon layers) and parameterized the y-position of the particle. The particle was assumed to be perfectly spherical, except where the effect of particle shape was tested. All dimensions used in the simulations are listed in Table 1.

Figure 21B:
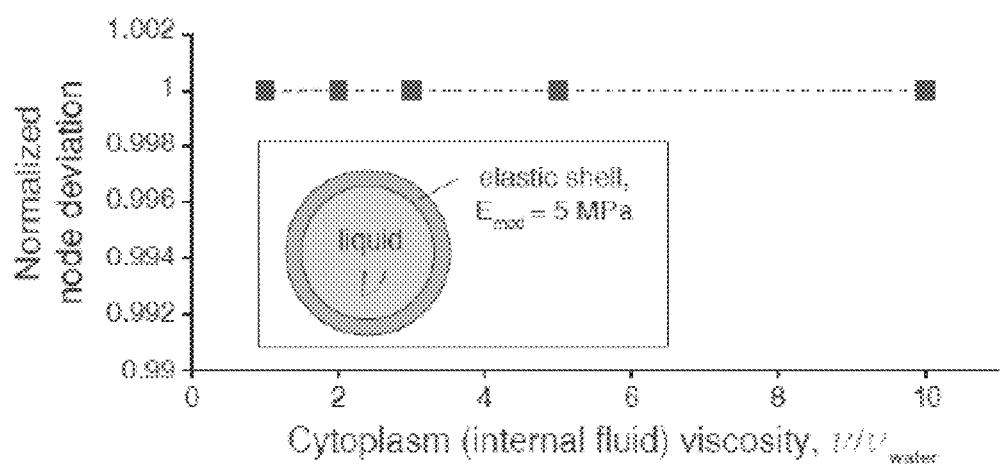
FIG. 21B is a simulation of results of liquid core-elastic shell model upon cytoplasm (internal fluid) viscosity, according to one set of embodiments.
Figure 21C:
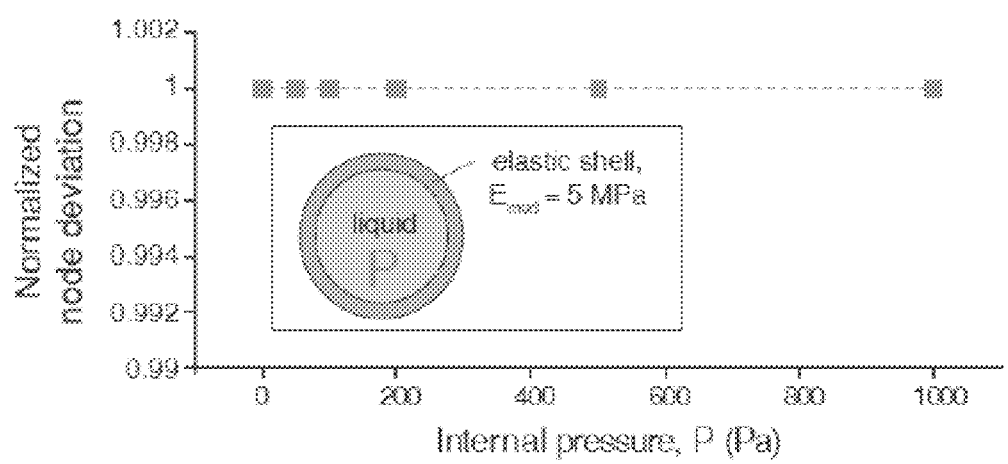
FIG. 21C is a simulation of results of liquid core-elastic shell model upon internal pressure, according to some embodiments.
Figure 22A:
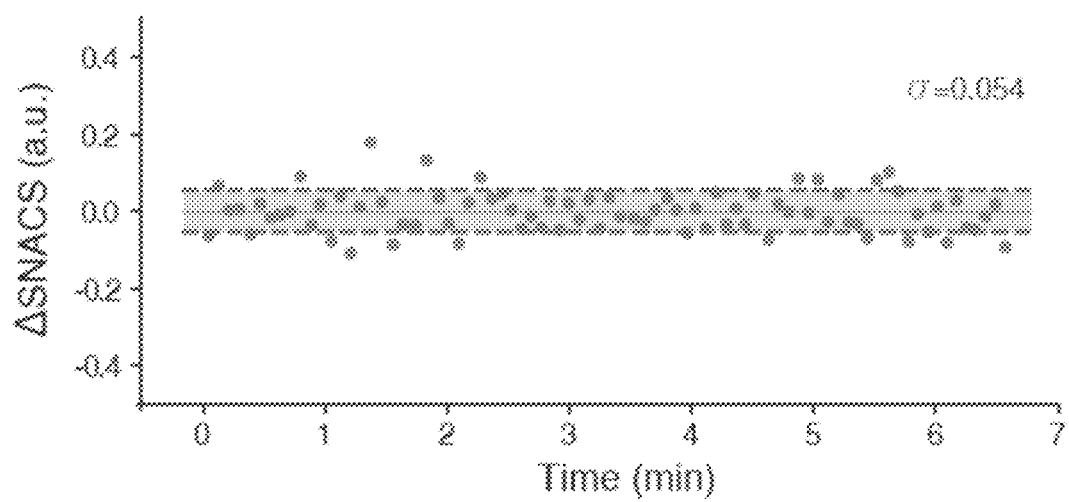
FIG. 22A is a continuous SNACS measurements (n=79) of a single 12 μm polystyrene bead implementing the same fluidic control strategy for continuous monitoring of single-cell stiffness, according to some embodiments.
Figure 22B:
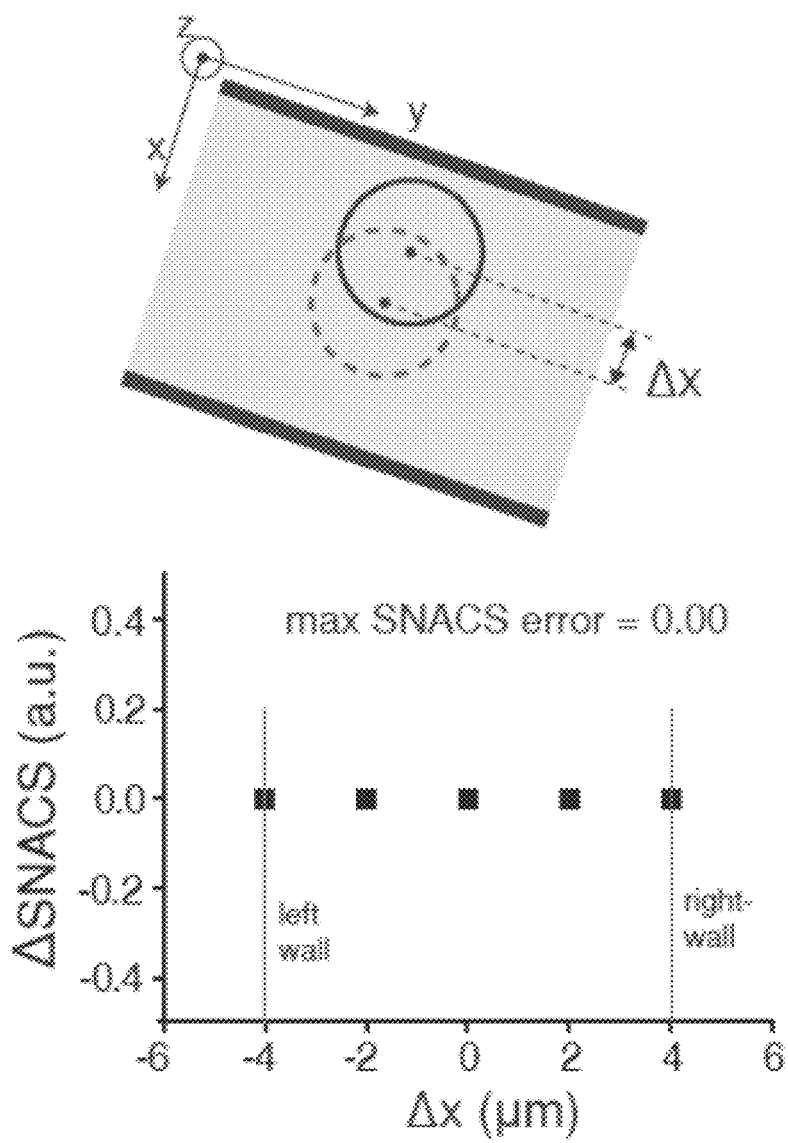
FIG. 22B is an illustration (top) and simulation results (bottom) of the cell model with total radius of 6 μm and shell elastic modulus of 5 MPa with x-positional variation within the channel. according to some embodiments.
Figure 22C:
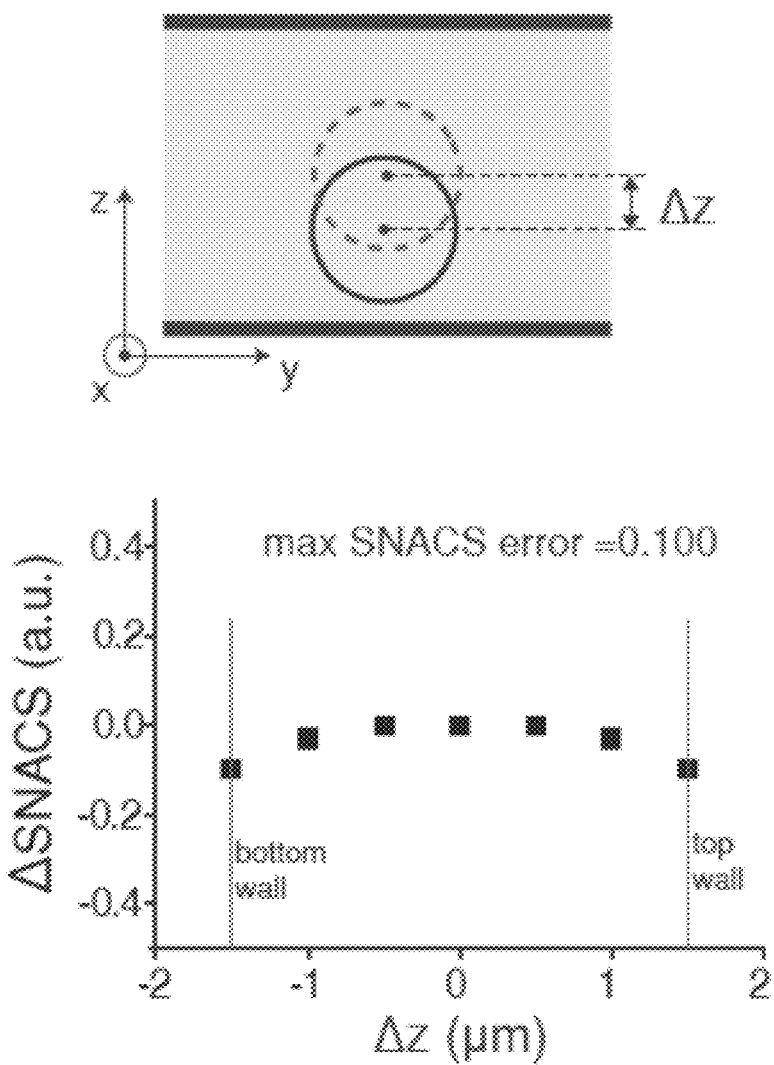
FIG. 22C is an illustration (top) and simulation results (bottom) of the cell model with total radius of 6 μm and shell elastic modulus of 5 MPa with z-positional variation within the channel. according to some embodiments.

The "Acoustic-Structure Interaction" module was used in the frequency domain provided by the software. There are multiple possible sources that generate acoustic standing waves, but most of them will be second or higher order terms in the acoustic parameters (e.g., centrifugal force acting towards the tip and node). The higher order acoustic sources were neglected, and the first order term was focused on, which is created by the out-of-plane motion of fluid channel in the cantilever, as given in Eq. (2).

$$a_t \equiv \ddot{z} = \omega^2 Au(y) a_b \equiv \ddot{z} = -\omega^2 Au(y) \quad (19)$$

where $a_t$ and $a_b$ are acceleration of the top and bottom surface, respectively. The 'hard-wall' boundary condition was used for the fluid-channel boundary because of the high stiffness ($>10^{11}$ Pa) and acoustic impedance of the silicon surrounding the fluidic channel. The same results were obtained by using a boundary condition that accounts for the silicon stiffness (data not shown). The entire particle was treated (and shell region for Liquid Core-Elastic Shell model) to be linearly elastic. COMSOL then solves for the elastic solid-acoustic interaction, which incorporates the re-radiation of the acoustic field by the vibration of the solid interface driven by the incident pressure field. For the cell model, the inner liquid core was treated as a fluid with density ρ=1.05 g/cm³ and sound velocity similar to salt water of the same density. Other cell models were tested, such as an elastic bulk, sphere of higher acoustic impedance as well as a viscous sphere (FIG. 21A-21C). The default tetrahedral meshing was used for the entire geometries (Table S2), except for the thin shell when performing simulation of the cell models, where the outer surface was meshed with triangles and a sweep function was used towards the inner surface (average distribution of 10). The particle or cell position in y-direction was parameterized and the center of mass was positioned in the center of the channel, except acquiring the positional error (FIG. 22A-22C).

Once COMSOL finished solving for the acoustic parameters as well as particle kinetics and elastic deformation, parameters (e.g. velocity, deformation) were integrated over specific geometries to obtain each energy term (Eq. (16)) as a function of the particle position (Table 2). Once all energy terms were calculated as a function of the particle position, the data was exported to MATLAB. To obtain ΔT(y) and ΔU(y), all energy terms were subtracted when the particle is at position y=0, from the energy terms when the particles is at position y;

$$\Delta U(y) = (U_f(y) + U_{p,s}(y) + U_c(y)) - (U_f(0) + U_p(0) + U_c(0)) \quad (20)$$

$$\Delta T(y) = (T_f(y) + T_{p,s}(y) + T_c(y)) - (T_f(0) + T_p(0) + T_c(0))$$

where $U_{p,s}$ and $T_{p,s}$ denote the potential and kinetic energy, respectively, of the whole particle or the shell region of the cell model. The average deformation of the cell or particle was calculated assuming isometric expansion (i.e., $U_{p,s}=EA\Delta x^2/2x$, where E is the young's modulus, A is the surface area of the cell or particle and x is the length before deformation, Δx). $U_c$ and $T_c$ only apply to the cell model, where encapsulated inner core was treated as a fluid.

Lastly, to directly compare simulations with experiments, the energy difference (in units of Joules, Eq. (20)) was converted to a frequency shift (in units of Hz, Eq. (18)). To do this, 10 μm polystyrene beads were run in both simulations and experiments the energy difference (ΔU(y)−ΔT(y)) was calibrated when the bead is at the antinode (y=$y_{an}$) with the resonant frequency shift measured experimentally at the antinode (Δf/f($y_{an}$)).

The resonant frequency shift of the SMR at any point in time due to a particle present in the integrated channel is a superposition of the frequency change due to the added particles mass and acoustic scattering created by the particle (FIG. 5B, FIG. 5C, and FIG. 6A), $$\Delta f_{measured} = \Delta f_{mass} + \Delta f_{acoustic} \quad (21)$$

It is assumed that $\Delta f_{mass}$ is the frequency shift caused by a point-mass particle as shown in Eq. (1), which is proportional to the squared amplitude dependence of the mode shape, $u^2(y)$. However, a particle with a mass distribution along the cantilever would cause a frequency shift deviating from the squared mode shape. Therefore, the shape-insensitive acoustic term, $\Delta f_{acoustic}$, was corrected for the mass distribution, $\Delta f_{mass}$, affecting $\Delta f_{measured}$ The contribution of acoustic effects to the frequency shift can be ignored and only the contribution of the mass distribution to the resulting frequency shift evaluated. If a particle of length 2 L with a linear mass distribution, λ(x), is located at the position y along the cantilever, the shift in the resonant frequency is given by:

$$\Delta f_{mass}(y) = \Delta f_{measured}(y_{an}) \frac{\int_{-L}^{L} \lambda(x) u^2(y+x) dx}{\int_{-L}^{L} \lambda(x) u^2(y_{an}+x) dx} \quad (22)$$

where $y_{an}$ is the position of the antinode and $\Delta f_{measured}(y_{an})$ is the measured frequency shift at the antinode (i.e., buoyant mass). Although a point mass would create no mass-dependent frequency shift at the node ($y_n$, $u(y_n)=0$), a particle with a non-zero size along the length of the cantilever will create a non-zero frequency shift when it is centered at the node. This contribution can be calculated from Eq. (22), and thus a correction can be made provided the size, shape and mass of the particle is known. The list of mass distributions, $\lambda(x)$, for some of the geometries that were encountered during this work is shown in FIG. 33. For simplicity, it was assumed that the mass is homogeneously distributed around the geometry. As expected, compared to the single spherical particle, a doublet of particles will result in a larger frequency shift due to mass elongation. Although spheres have positional invariance making $\lambda$ invariant to particle rotation, the $\lambda$ for a doublet depends on its orientation relative to the cantilever (FIG. 33).

Figure 24A:
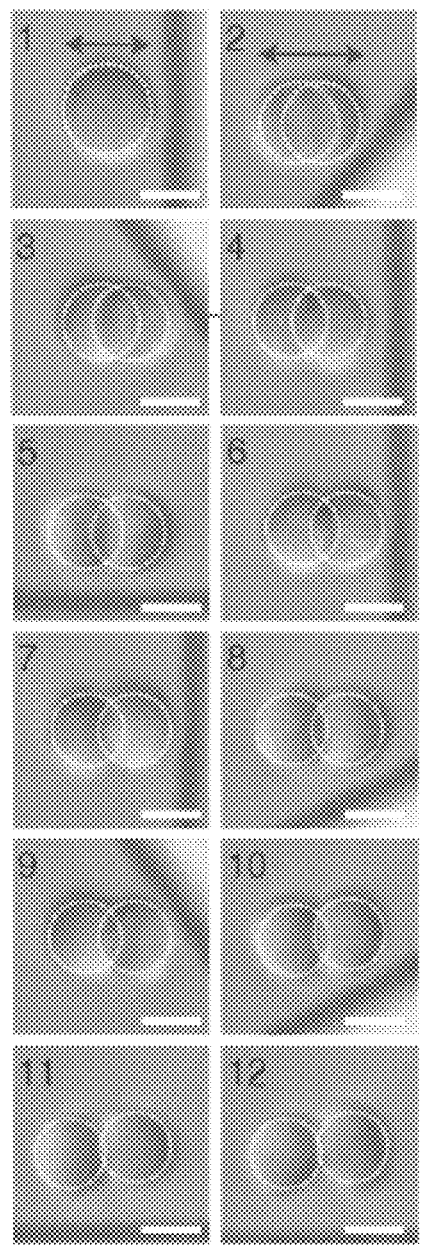
FIG. 24A shows DIC images of the mitotic L1210 cell acquired on-chip, simultaneously with SNAGS and buoyant mass measurement in late mitosis, according to one set of embodiments.
Figure 24B:
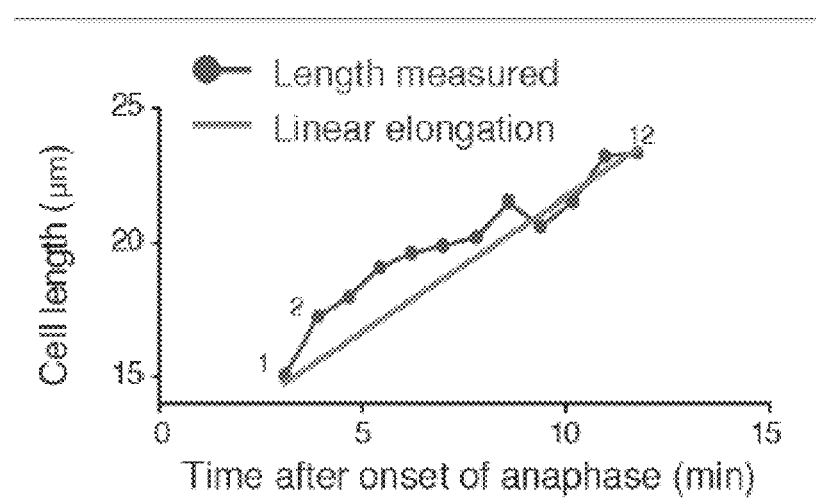
FIG. 24B is cell length plotted as a function of time after onset of anaphase, according to certain embodiments.
Figure 24C:
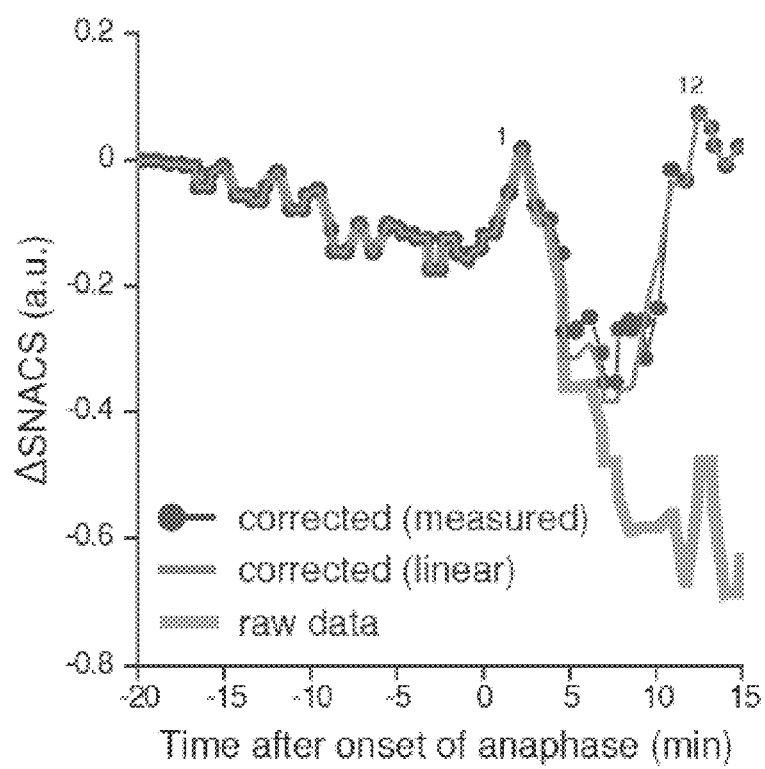
FIG. 24C is SNAGS before correction (gray), after correction for the mass elongation using length directly measured from DIC images (dots) and assuming linear elongation (line), plotted as a function of time after onset of anaphase, according to some embodiments.
Figure 31:
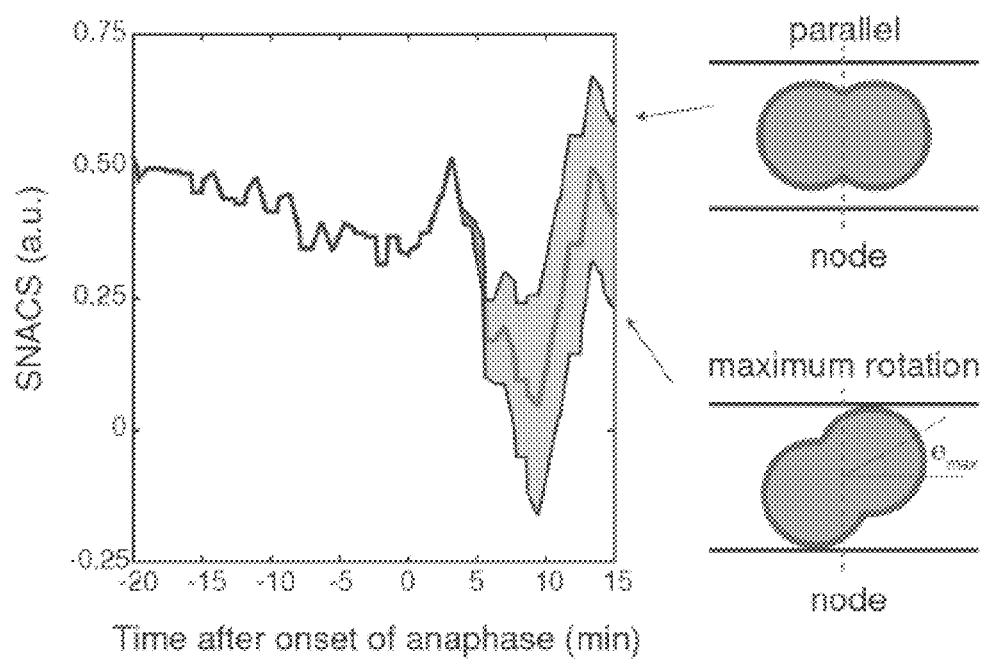
FIG. 31 shows SNACS corrected assuming two different extreme orientations relative to the channel when cell is at the node (left) and a schematic showing the two extreme orientations of a cell during late mitosis (right), according to one set of embodiments.

During the transition from a singlet to a doublet during anaphase, it was assumed that the total volume remains constant and that all geometries are the result of an overlap of two equally sized spheres (FIG. 24A-24C). Numerically solving for an individual sphere radius, $r_t$, with total elongation length, L, and volume, V, accomplished this, matching the following conditions:

$$L = 4r_t - d$$

$$V = 2\int_{-r_t}^{r_t - y/2} \pi(r_t - x)^2 dx$$

where d is the length of intersection between two identical spheres (FIG. 33). With $r_t$ obtained above, the following frequency shift can be added to the measured node deviation to correct for the mass elongation effect.

$$\Delta f_{correction}(y_n) = \Delta f_{measured}(y_{an}) \left[ \frac{\int_{-L/2}^{L/2} \lambda_t(x) u^2(y_n + x)dx}{\int_{-L/2}^{L/2} \lambda_t(x) u^2(y_{an} + x)dx} - \frac{\int_{-r_s}^{r_s} \lambda_s(x) u^2(y_n + x)dx}{\int_{-r_s}^{r_s} \lambda_s(x) u^2(y_{an} + x)dx} \right] \quad (24)$$

where $y_n$ is position of the node and $\lambda_t$ and $\lambda_s$ refer to the linear mass distribution of the overlapping spheres of individual radii of $r_t$ and singlet of radius $r_s$, respectively (Table S3). However, since $\lambda_t$ depends on the exact orientation relative to the channel, there will be an error estimating the frequency shift, $\Delta f_{correction}$. For the data shown, it has been assumed that the cells are oriented by an intermediate angle (i.e., $\theta_{max}/2$) during late mitosis (FIG. 31).

Figure 15A:
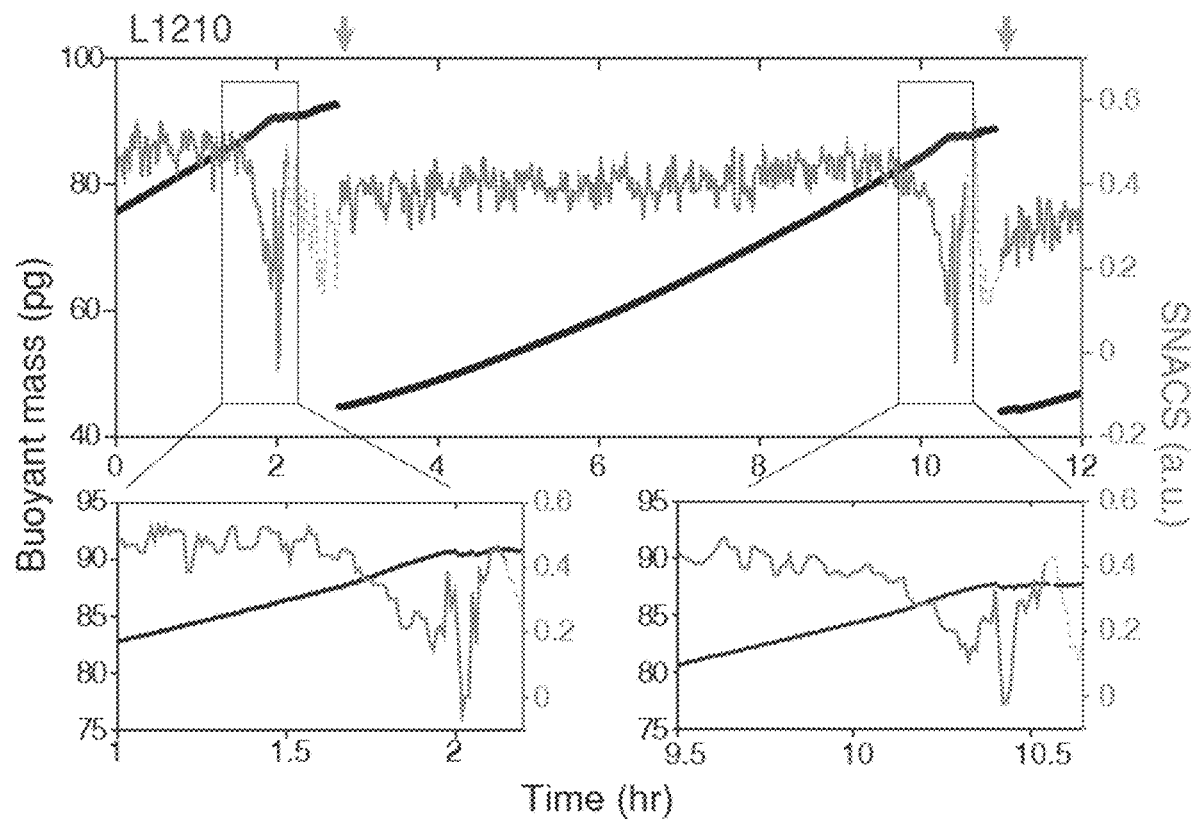
FIG. 15A is a plot of buoyant mass and SNACS of a L1210 cell measured over two cell divisions with <1 min temporal resolution by flowing the cell back-and-forth through the SMR, according to one set of embodiments.
Figure 15B:
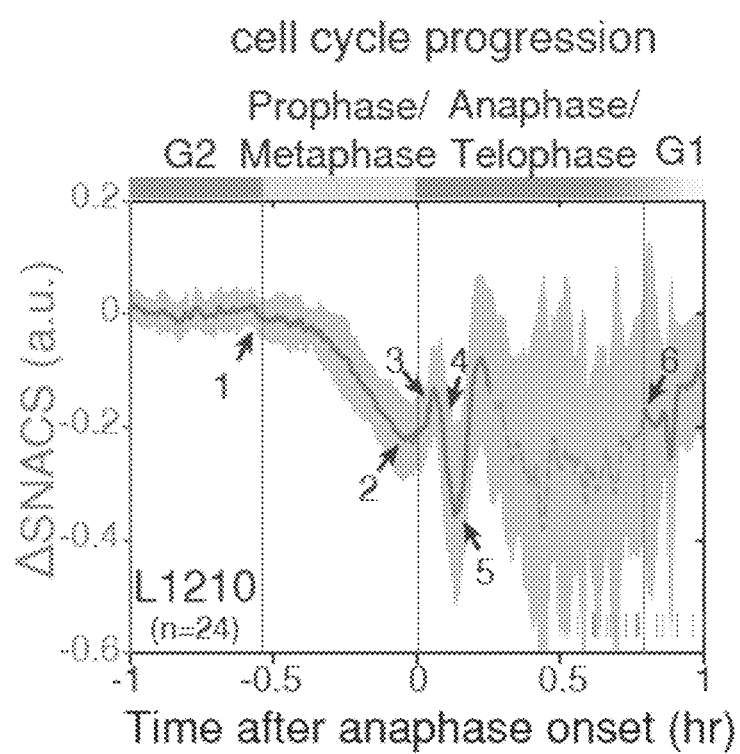
FIG. 15B is a plot of mean SNAGS versus time, and standard deviation of L1210 cells during mitosis, according to one set of embodiments.

Orientation of a particle relative to the channel can affect mass distribution along the channel and result in a SNACS that is independent of the stiffness (FIG. 33). For example, the SNACS from a cylindrical particle flowing parallel through the channel at the node will be different from the case where the same particle has a perpendicular orientation (FIGS. 33, 1st and 2nd row, respectively). Thus, for non-spherical particles, the SNACS measurement contains an intrinsic noise that results from an uncertain orientation during detection at the node. For suspension cells, the shape is generally spherical up until late mitosis and so the orientation noise is negligible. This is evident by the low noise in the stiffness measurement during interphase (FIG. 15A and FIG. 15B).

For cells that deviate from a spherical shape, a spurious SNACS signal could arise if the cell gradually changes its orientation as it flows back-and-forth through the channel. There are two approaches for determining if a signal is spurious. The first applies to situations where the time range of a possible stiffness change is known (e.g. during mitosis). In this case, the SNACS signal can be measured from multiple cells. The resulting signals can be aligned and an analysis for statistical significance can be performed (for example, FIG. 15C, where mitotic cells were aligned at the metaphase-anaphase transition). If a cell's orientation should gradually drift during a measurement, it will not be correlated across different cells.

The second approach applies to situations where changes in stiffness occur stochastically. In this case, the error resulting from orientation noise was quantified. A threshold can then be established for determining if the SNACS measurement is revealing statistically significant changes in cell stiffness. The maximum orientation error in node deviation ($\Delta ND_{orientation}$) can be calculated provided the cell shape is known (e.g. by DIC imaging), $$\Delta ND_{orientation} = \Delta f_{mass,or1}(y_n) - \Delta f_{mass,or2}(y_n) \quad (25)$$

where $\Delta f_{mass}(y_n)$ is given in Eq. (22). If the change in SNACS is sufficiently larger than the error obtained from Eq. (25), the resulting signal will be associated with changes in cell stiffness.

For a cylindrical particle of radius r and length L, the maximal node deviation change due to orientation error given by Eq. (25) is:

$$\Delta ND_{orientation} \Delta f_{mass,c\parallel}(y_n) - \quad (26)$$

$$\Delta f_{mass,c\perp}(y_n) = \Delta f_{measured}(y_{an}) \left[ \frac{\int_{-L/2}^{L/2} \lambda_{c\parallel}(x) u^2(y_n + x)dx}{\int_{-L/2}^{L/2} \lambda_{c\parallel}(x) u^2(y_{an} + x)dx} - \frac{\int_{-r}^{r} \lambda_{c\perp}(x) u^2(y_n + x)dx}{\int_{-r}^{r} \lambda_{c\perp}(x) u^2(y_{an} + x)dx} \right]$$

where, $\lambda_{c\parallel}$, $\lambda_{c\perp}$ is mass distribution function of a cylindrical sample lying parallel and perpendicular to the channel, respectively. From Eq. (26), a cylindrical hydrogel with a 10 μm diameter, 8 μm height and $\Delta f_{measured}(y_{an})=17$ Hz, the resulting orientation noise is ~0.004 Hz, which is equivalent to SNACS noise of ~0.006 (a.u.).

The orientation noise of a cell in late mitosis is estimated. Specifically, using Eq. (25), the maximum error from orientation uncertainty as the cell elongates can be calculated. Similar calculations done for the cylindrical hydrogel shown will be performed. However, since the length of the elongated cell is greater than the channel width, the maximal rotation is now constrained. For example, overlapping spheres of total elongation length L, and individual radius $r_t$, flowing through the channel of width w can only rotate by an angle $\theta$ from y-axis (i.e. direction of a particle/fluid flow through the cantilever) (FIG. 3A and FIG. 13A) which is given by:

$$2r_t + (L - 4r_t)\sin(\theta_{max}) = w \quad (27)$$

Using w=20 µm for our cantilever and the maximal angle provided from Eq. (27), FIG. 31 bounds the maximum error due to orientation uncertainty as the cell elongates. Initially the error increases as the cell elongates. At a critical elongation length, the error reaches a maximum because the rotation within the channel begins to be constrained ($\theta_{max}$<90°).

Figure 32:
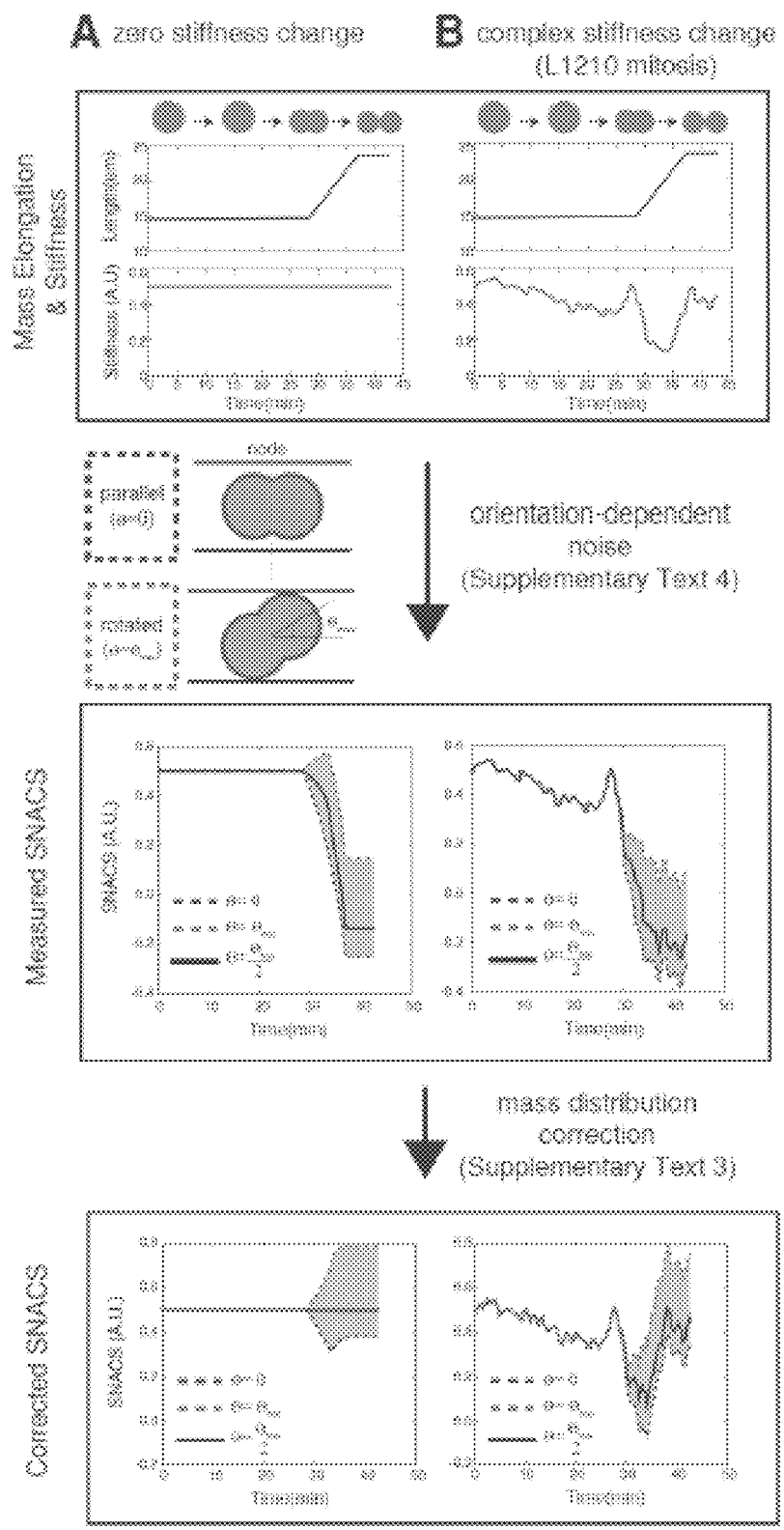
FIG. 32 shows the effect of orientation uncertainty on measured SNACS and corrected SNACS for two hypothetical cells both elongating as L1210 cells in mitosis, but with different stiffness behavior, and orientation-dependent noise to the SNACS signal, according to certain embodiments.

It was previously described how to correct the SNACS signal for changes in mass distribution obtained by simultaneously measuring cell shape. Here, the expected SNACS signal from a hypothetical cell that elongates during mitosis is described. In one case, the stiffness is allowed to remain constant during elongation (FIG. 32, left $1^{st}$ panel), and for the other case, to change in a fashion similar to what was observed in L1210 cells (FIG. 32, right $1^{st}$ panel). As shown in previous note (Eq. (22)), elongation causes the measured SNACS signal to be decreased due to mass distribution changes, but also variable depending on the orientation relative to the channel. The SNACS decrease and increased noise are independent from the cell's stiffness (FIG. 32, $2^{nd}$ panel; gray area). In other words, SNACS measured at any given time point can fall along the gray region in FIG. 32 second panel. If the mass distribution correction scheme is applied to the expected SNACS curves, the stiffness trajectory is recovered where the error is determined by the upper and lower bound calculated from the orientation (FIG. 32, $3^{rd}$ panel; gray area). It is clear that the orientation-dependent noise is small enough to distinguish cellular stiffness changes observed in mitotic L1210 cells (FIG. 32, right) from the hypothetical constant stiffness case (FIG. 32, left).

Here, the mathematics that govern the reduction of cortical thickness when the total volume expands are presented. For this calculation, it was assumed that the volume expansion is isometric and that the cortical actin content and density does not change as a result of the expansion. Therefore, when a shell of thickness, $t_s$, and total radius, $r_c$ (FIG. 7A and FIG. 16D) undergoes isometric volume expansion to bigger radius, $r'_c$, the shell thickness would be reduced to $t'_s$:

$$4/3\pi r_c^3 - 4/3\pi(r_c - t_s)^3 = 4/3\pi r'^3_c - 4/3\pi(r'_c - t'_s)^3 \quad (28)$$

Table 3 lists some of the values that were calculated using Eq. (28).

TABLE 3

List of calculated cortical thickness change upon isometric volume expansion.

| swelling amount (% Vol) | absolute cortex thickness change (%) | cortex thickness to diameter after swelling (%) | Note |
|---|---|---|---|
| 10 | 6.33 | 0.907 | 1% before swelling |
| 14.1 | 8.65 | 0.874 | FIG. 4D |
| 15 | 9.14 | 0.867 | |
| 20 | 11.75 | 0.831 | |

The FEM simulation revealed that increasing volume by 14.1% and, consequently, decreasing the cortex thickness to radius ratio by ~10% indicated an additional 10% decrease in cortical stiffness to match with the stiffness observed in mitosis (FIG. 16C). This could be because cortical expansion during swelling causes actin cortex to be detached from the surface or because F-actins get partially damaged or ruptured by an increase in intracellular pressure.

There is evidence that suggests the cell stiffness measurement is dominated by the cell cortex. First, in the FEM simulations, SNACS does not change when the internal viscosity and intracellular pressure are altered (FIG. 21A-21C). Second, upon nuclear envelope breakdown where internal structure rapidly remodels, rapid changes in SNACS is not observed. Lastly, previous observations have shown that cortical elasticity dominates stiffness measurements when only small deformations are applied.

It is important to note that our SNACS measurement is generally influenced by the cell's mass distribution along the cantilever. During anaphase and telophase, the cell's mass distribution changes substantially, which causes the SNACS measurement to generally depend on the cell's orientation within the channel (FIG. 31, FIG. 32, and FIG. 33). Therefore, obtaining stiffness from the acoustic scattering readout uses mass distribution information through bright-field images unless, for example, cell shape is known a priori. In round interphase cells, this correction is not necessarily needed. Another important feature of this measurement is that it quantifies the overall stiffness of a cell. Finally, the measurement uses cells in suspension.

It has been demonstrated that cortical tension increases in metaphase due to increases in hydrostatic pressure and outwards force generated by the cell during the mitotic cell swelling. However, cortical tension and cortex stiffness measurements respond to osmotic specific domain. As shown in FIG. 3A, the geometry of an SMR was reproduced in the software implementing physical dimensions. In the detection regime of the cantilever (e.g., internal microchannel, covered with thin silicon layers), a spherical particle was embedded. The y position of the spherical particle was parametrized during the study.

Figure 4B:
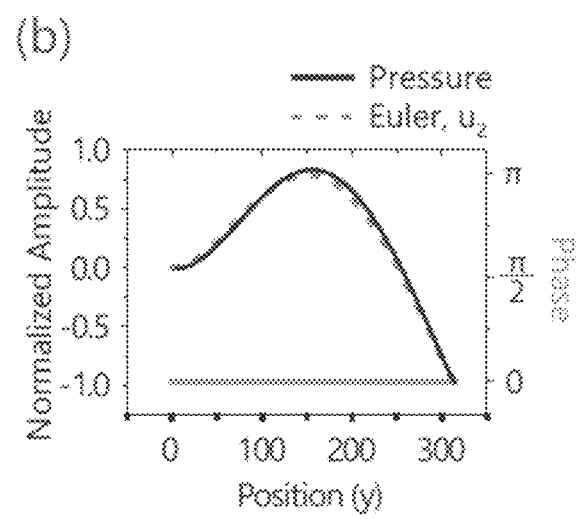
FIG. 4B is COMSOL simulation of normalized pressure and vibration amplitude versus position of a particle for a suspended microchannel, according to one set of embodiments.

Briefly, a silicon layer surrounding the fluid was set to follow harmonic motion in eq. (2), and solved for fluid displacement and pressure (FIG. 4A). Surprisingly, a dominant acoustic standing wave was found to be generated in the fluid channel. The pressure distribution along the cantilever was very similar to the drive amplitude of the silicon layer, and was in phase with the vibration (FIG. 4B). The presence of pressure standing wave suggests that besides the bending of silicon layers, additional energy is stored in the form of acoustic potential energy, $w_p$, and thus may contribute to C in eq (3). In fact, it was found that z-directional fluid velocity precisely follows the previous theory. However, additional direction of motion that was neglected in the ideal case was present, not dominant as the z-directional movement, yet reasonably significant (10% of z-directional velocity). The distribution was different from the driving amplitude. All velocities were out of phase with the cantilever motion, implying that acoustic kinetic energies contribute to D in eq. (3). FIG. 4C shows z-directional acoustic velocities along the cantilever. The overall shape is the same as the 2nd bending mode, as assumed in the theory (red dash). It is completely out-of phase with cantilever bending (straight line in FIG. 4C). FIG. 4D shows y-directional acoustic velocities along the cantilever. It's magnitude is ⅒ that of z-directional velocity. It is also out-of-phase with the cantilever bending (straight line in FIG. 4D).

Figure 5A:
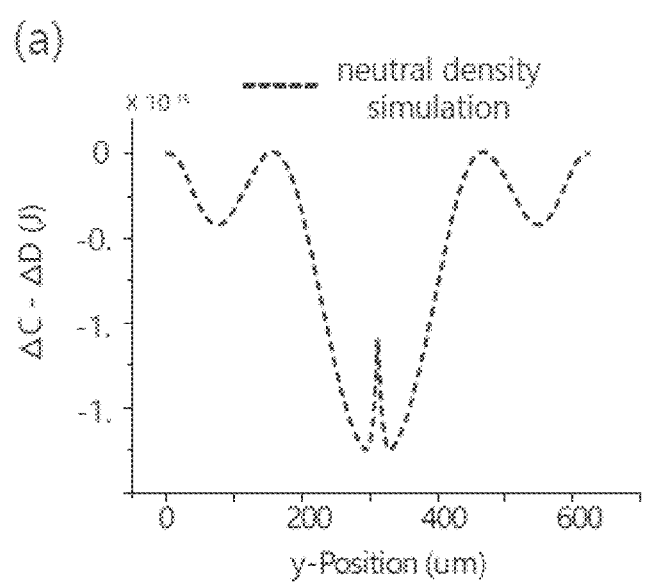
FIG. 5A is a plot of ($\Delta C$-$\Delta D$) derived from COMSOL simulation as a function of particle position, according to one set of embodiments.
Figure 5B:
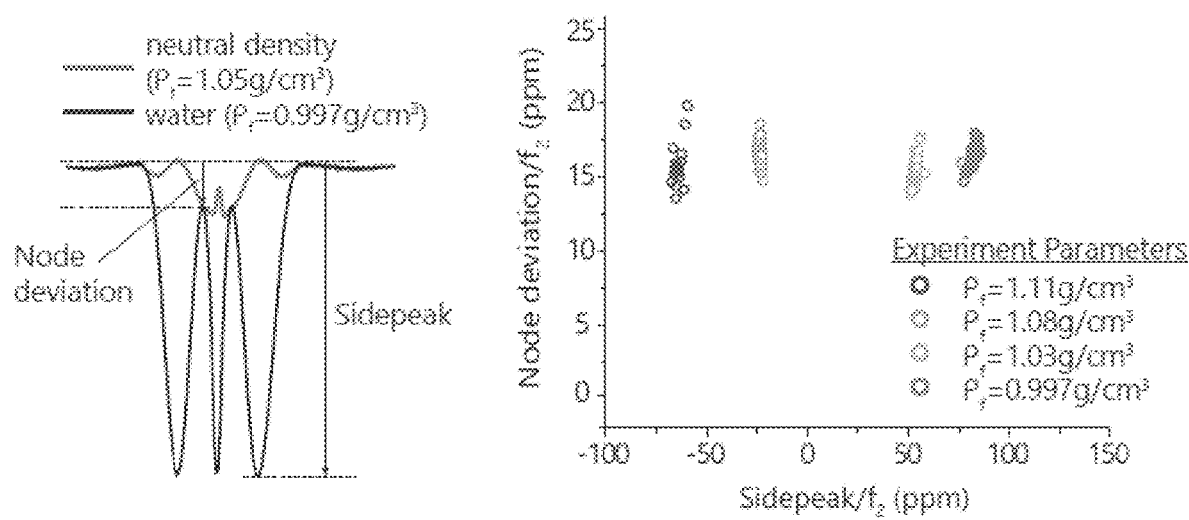
FIG. 5B is a plot of node deviation versus sidepeak for a particle flowing through fluids of varying density (pf), according to one set of embodiments.
Figure 5C:
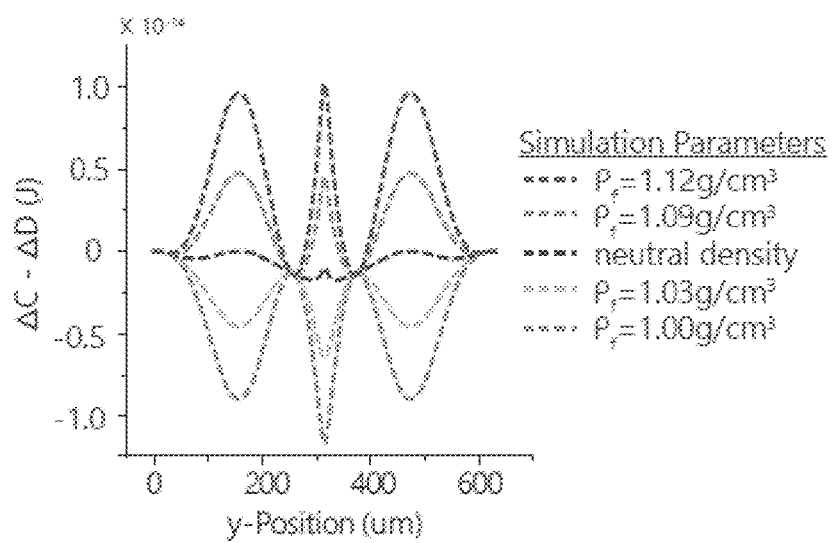
FIG. 5C is a plot of ($\Delta C$-$\Delta D$) derived from COMSOL simulation as a function of particle position, according to one set of embodiments.
Figure 5D:
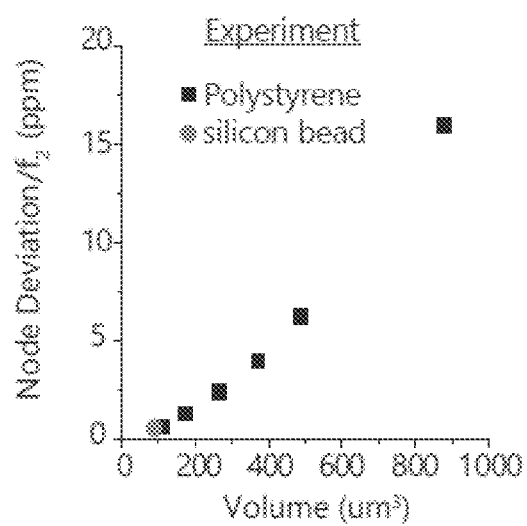
FIG. 5D is a plot of node deviation versus volume of a particle, according to one set of embodiments.
Figure 5E:
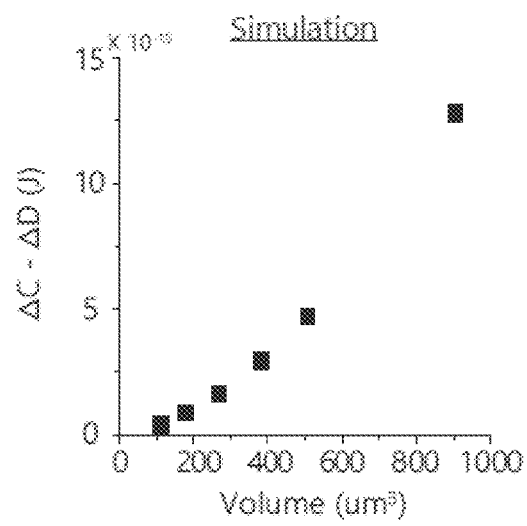
FIG. 5E is a plot of ($\Delta C$-$\Delta D$) derived from COMSOL simulation as a function of particle volume, according to one set of embodiments.

Next, the case of polystyrene particle embedded in the channel was simulated in FEM. Compared to the case of no particle, a significant deviation of acoustic energy terms from the theory as a function of the particle position was observed. Incorporating particle kinetic energy and combining all energy terms ($\Delta C - \Delta D$) as a function of particle position, the frequency shift of neutral density that was experimentally observed was generated (FIGS. 5A-5C). Node deviation, both observed experimentally and in simulation, was not generally affected by the fluid density. Yet, it was observed that particle size affected the Node deviation, and indeed, observed in the simulation as well (FIGS. 5D and 5E). Amplitude of vibration, did not affect the signal, as expected.

Figure 6A:
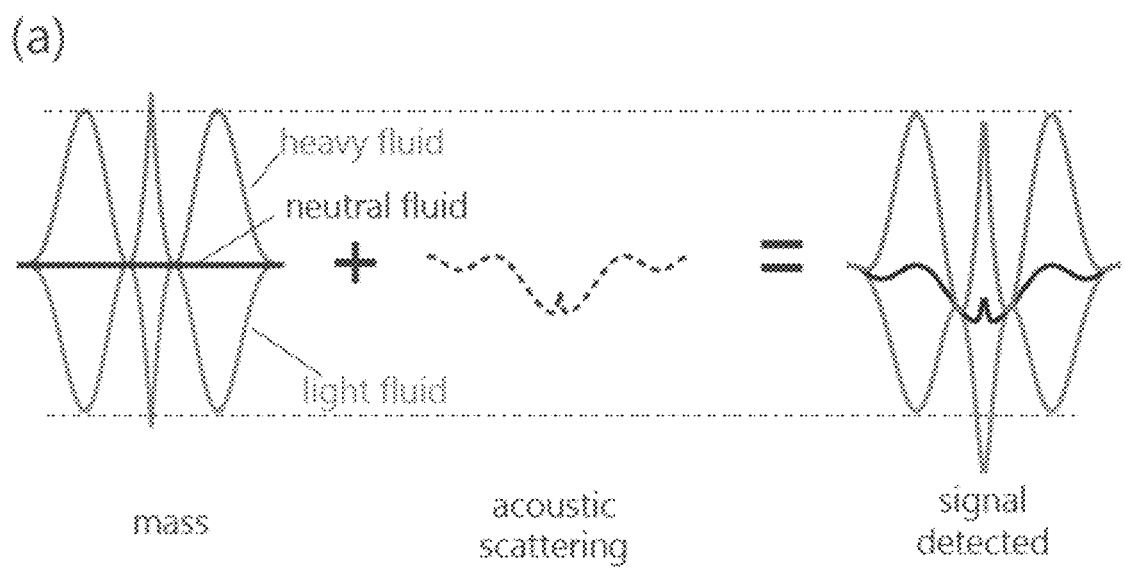
FIG. 6A is a schematic illustration of the effect of acoustic scattering on a frequency signal, according to one set of embodiments.

The acoustic scattering is generally independent from the pure mass change (FIG. 6A). Observation in the frequency shift may be the sum of effect from acoustic scattering and pure mass change in system. Acoustic scattering may not be affected the frequency shift at antinode, where one often derives mass. Moreover, acoustic scattering may be nearly maximal at the node, where pure mass effect is zero ($u_n(y)=0$, see eq. (1)). Therefore, one may be able to measure the mass of the particle using the frequency at antinode while subsequently acquiring acoustic signal/interaction at node.

Figure 6B:
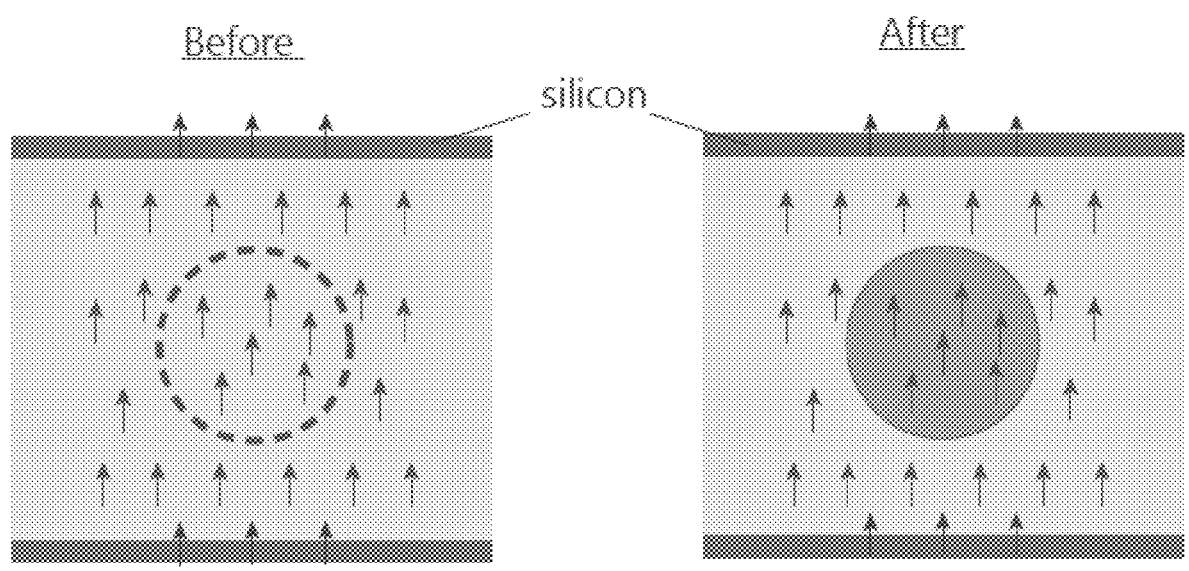
FIG. 6B is a schematic illustration showing fluid kinetics without considering acoustic scattering generated by a particle, according to one set of embodiments.
Figure 6C:
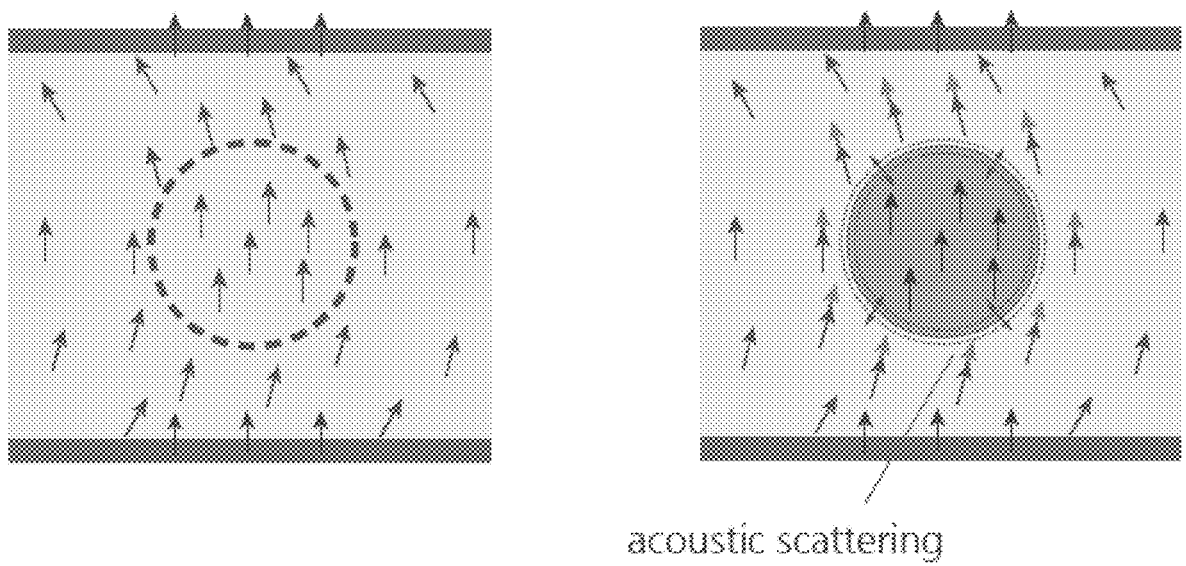
FIG. 6C is a schematic illustration showing fluid kinetics with consideration of acoustic scattering generated by a particle, according to one set of embodiments.

In addition, near-field acoustic scattering may be responsible for such deviation. Previous theory has generally neglected interaction of fluid and particle embedded, considering a particle to "replace" the fluid of the same volume, following the same kinetics of the fluid before replacement (FIG. 6B). This may be why only pure mass change was considered to play a role in determining the frequency. The new understanding taking fluid-particle interaction into consideration, however, suggests that the interaction produces non-trivial acoustic scattering which affects the nearby fluid kinetics (FIG. 6C). In fact, acoustic velocities and pressure near the particle was observed to be significantly different from when the particle is not present.

Example 3—Acoustic Scattering of Biological Entities Such as Living Cells

Figure 7A:
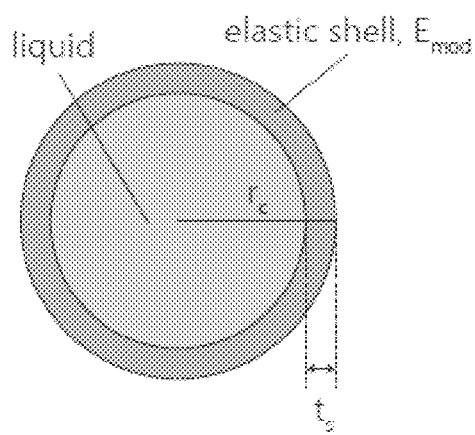
FIG. 7A is a schematic illustration of the, Cortical Shell-Liquid Core model, according to one set of embodiments.
Figure 7B:
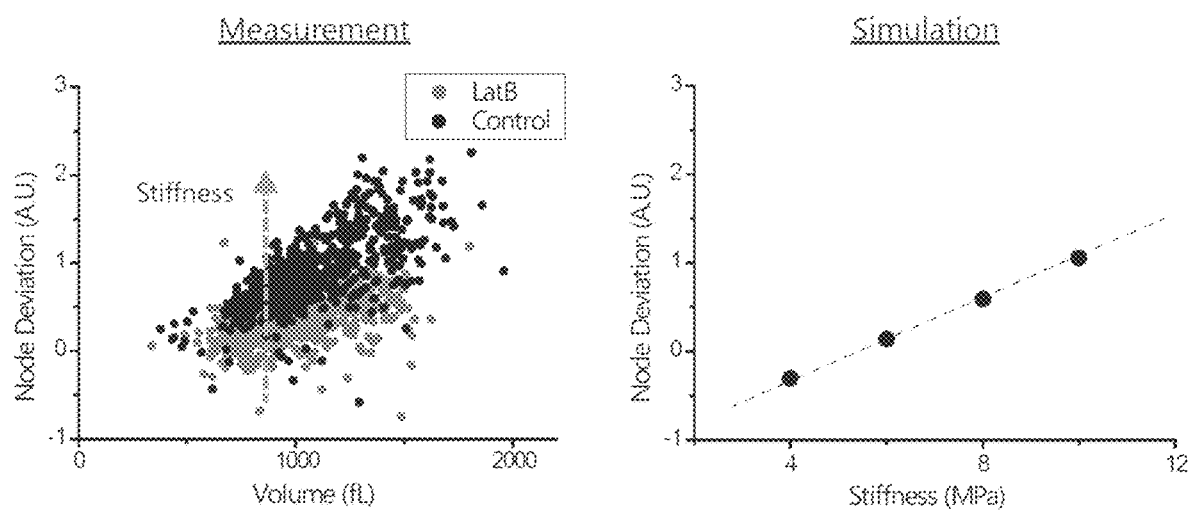
FIG. 7B is a plot of node deviation versus particle volume (left) and COMSOL simulation data of node deviation versus varying cortical stiffness (right) for a plurality of live L1210 cells in the presence of LatB or absence of LatB (control), according to one set of embodiments.
Figure 7C:
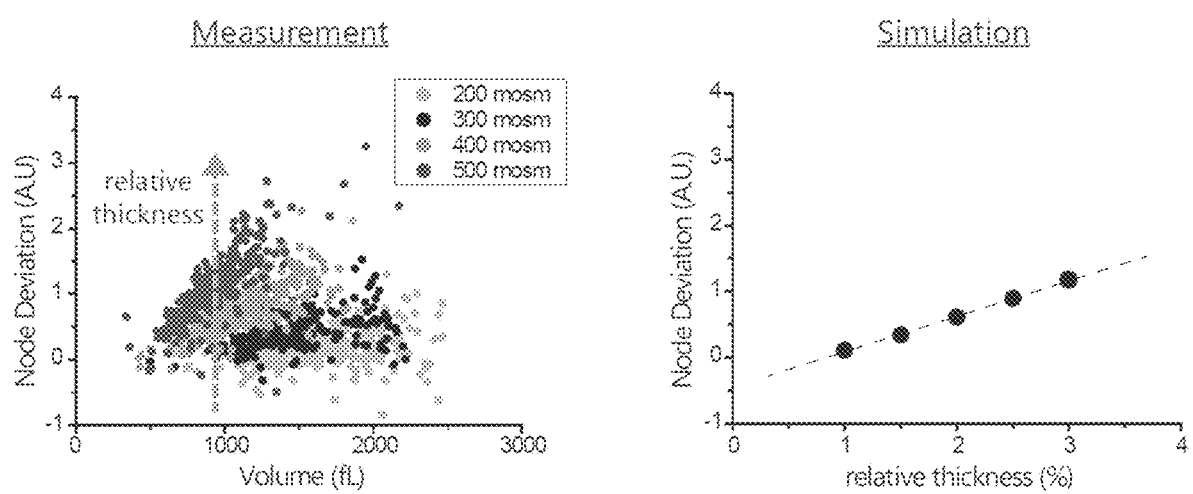
FIG. 7C is a plot of node deviation versus particle volume (left) and COMSOL simulation data of node deviation versus varying cortical relative thickness (right) for a plurality of live L1210 cells in surrounding fluids of varying osmolarity, according to one set of embodiments.
Figure 8A:
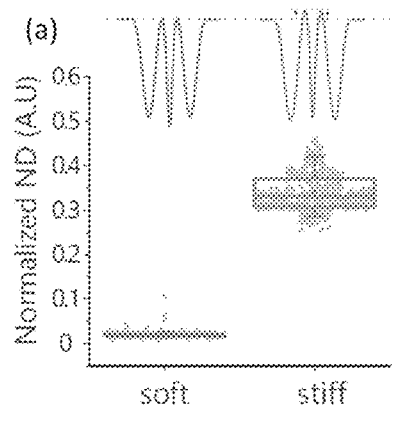
FIG. 8A is a plot of normalized node deviation versus soft or stiff synthetic particles, according to one set of embodiments.
Figure 8B:
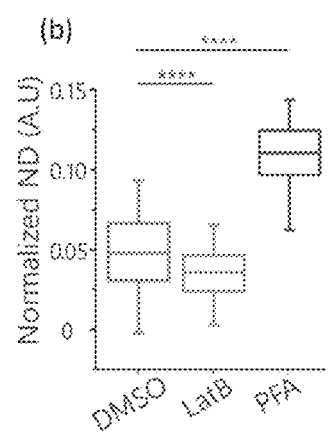
FIG. 8B is a plot of normalized node deviation for mechanically altered cells, according to one set of embodiments.
Figure 8C:
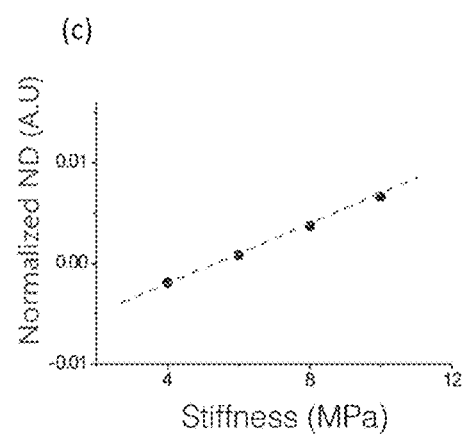
FIG. 8C is a plot of normalized node deviation versus stiffness (MPa) for simulated particles, according to one set of embodiments.

Live mouse lymphoblast (L1210) cells produced positive node deviation, opposite to the case of polystyrene. It was investigated whether a simple model of a cell correctly explained the frequency deviation at the node. Among various models tested, Cortical Shell-Liquid Core model was very successful in generating similar node deviation (FIG. 7A). Briefly, this models a cell as a liquid confined by a thin elastic layer. Using the most widely adopted parameters (shell thickness, $t_s/r_c=1\%$ and Poisson's ratio $v=0.5$), a Young's elastic modulus that matched well with experimental observations was obtained. The Young's modulus ($E_{mod}=4-8$ MPa) is ~40-80 times greater than previous reported value in red blood cells using AFM, which may be due to power-law relation of Young's modulus on loading frequency: $E \propto f^{0.2-0.75}$. To further validate the cell model, drugs that disrupt the actin cortex were used and a decrease in the deviation was observed—a similar trend was observed when stiffness of the cortical shell or relative thickness was decreased (FIGS. 7B-7C). Moreover, increasing osmolarity of surround fluid of a cell increased the signal at node. It has been reported that sudden osmotic shock reduces intracellular water content which may increase the relative actomyosin cortex, and may be simply modeled as thicker elastic layer (increase in $t_s/r_c$ in FIG. 7A). Besides, osmotic shock, cross-linking within the cell surface without permeabilizing the membrane, also increased the node deviation, which may be explained by an increase in cortex stiffness. FIG. 8A shows the normalized node deviation of synthetic particles with different stiffness. FIG. 8B shows the normalized node deviation of mechanically altered cells. L1210 cells were treated with Latruculin B (LatB) for actin depolymerization or fixed with Paraformalhyde (PFA) for cell surface cross-linking FIG. 8C shows the simulation of normalized node deviation response from particles of varying stiffness, for comparison.

Figure 9A:
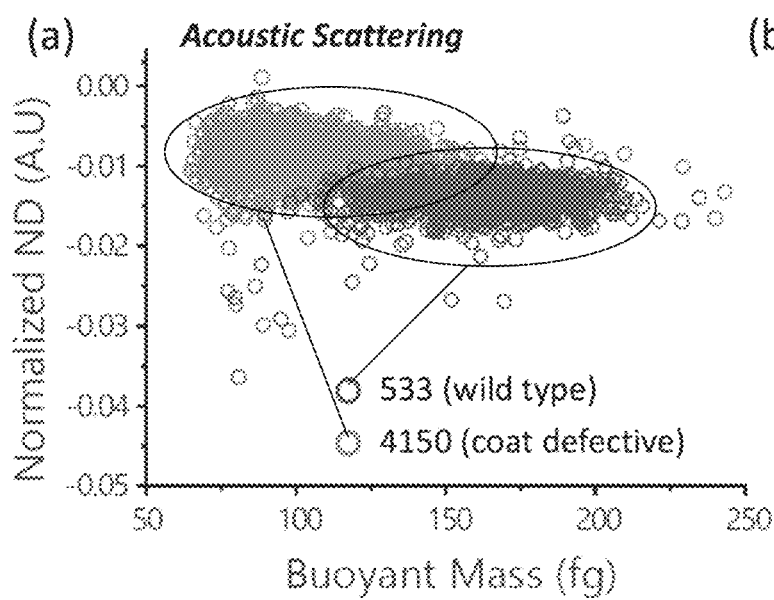
FIG. 9A is a plot of normalized node deviation versus buoyant mass for wildtype and coat defective dormant *B. subtilis* spores in water, according to one set of embodiments.
Figure 9B:
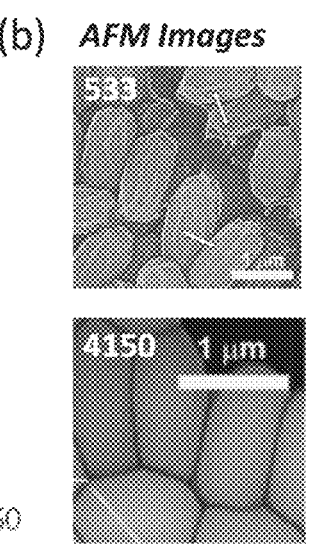
FIG. 9B are atomic farce microscopy (AFM) images of the spore types plotted in FIG. 9A, according to one set of embodiments.

FIGS. 9A-9B show normalized node deviation versus buoyant mass for wildtype (533) and coat-defective (4150) dormant *B. subtilis* spores in water. These strains are expected to have differing deformability which is reflected by the normalized node deviation. In particular, the magnitude of normalized node deviation for the coat-defective spores was observed to be roughly half of that for wild-type.

Figure 14A:
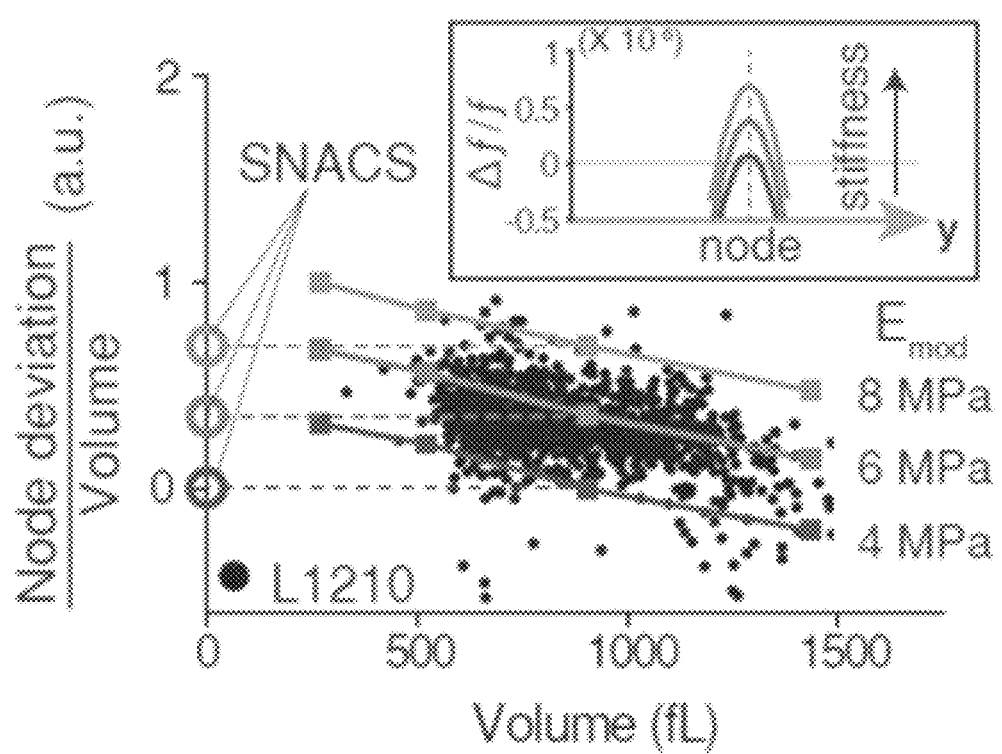
FIG. 14A is a plot of node deviation versus volume from experiments with L1210 cells and simulations using the model for three values of cortical stiffness, according to one set of embodiments.

The inset in FIG. 14A shows simulated frequency response of different cortical stiffness (V=900 fL). To correct for cell size dependence of the node deviation measurement, a size-independent cortical stiffness parameter was derived from the iso-elasticity lines obtained from the FEM simulations, called the size-normalized acoustic scattering (SNACS), as shown in FIG. 14A, FIG. 19, and FIG. 20A-FIG. 20C. The iso-elasticity lines fit well with the measurements from hundreds of live cells. Three other mechanical models were also tested, such as impedance mismatch, viscous drop, and elastic bulk (FIG. 21A-FIG. 21C).

Figure 14B:
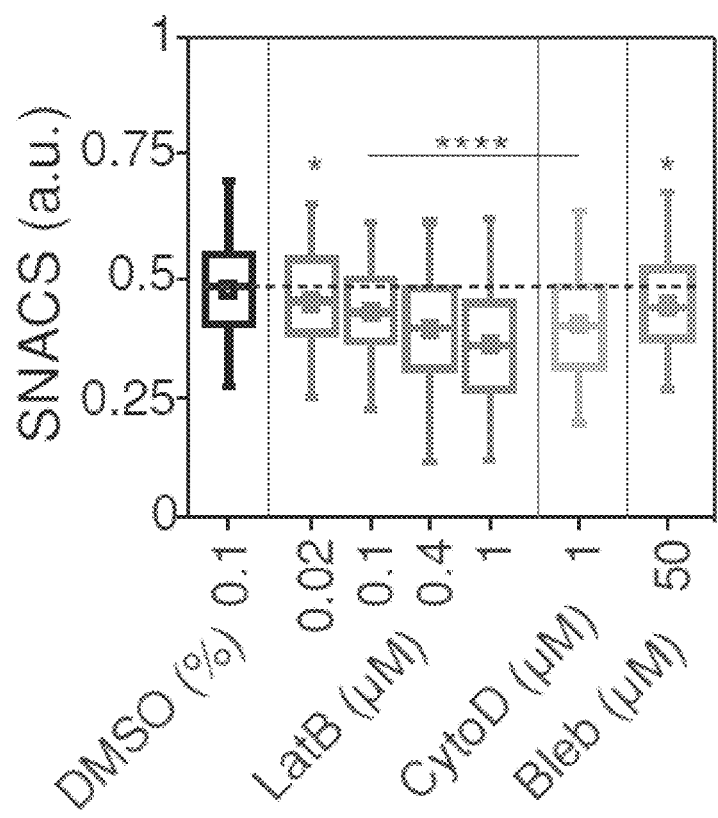
FIG. 14B is a plot of SNACS obtained from L1210 cells treated with inhibitors of actomyosin cortex, according to one set of embodiments.
Figure 14C:
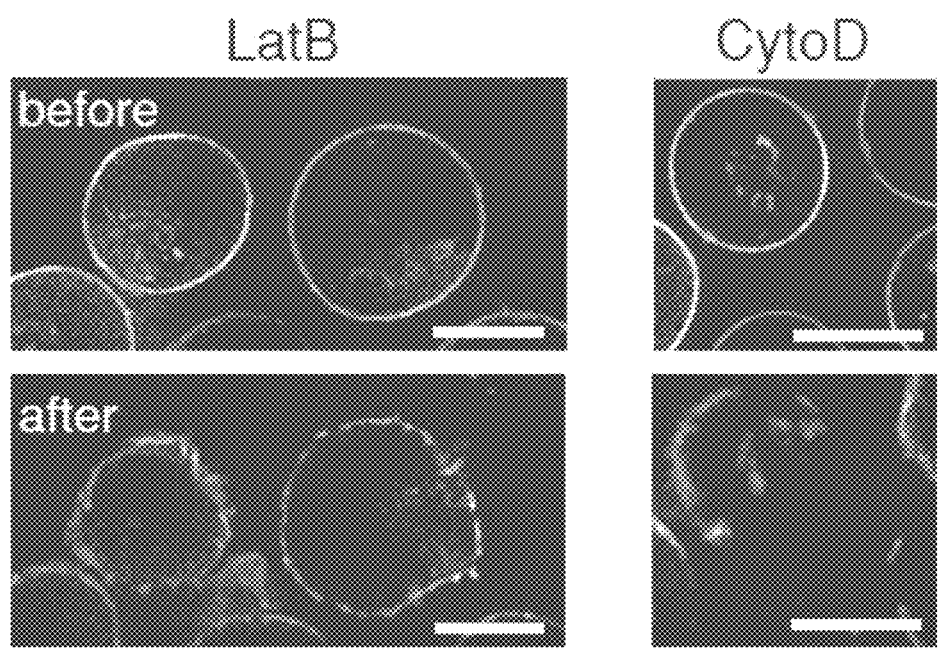
FIG. 14C is representative single z-layer images of F-actin (LifeAct) from live L1210 cells before and after 1 μM LatB and 1 μM CytoD treatment, according to one set of embodiments.
Figure 14D:
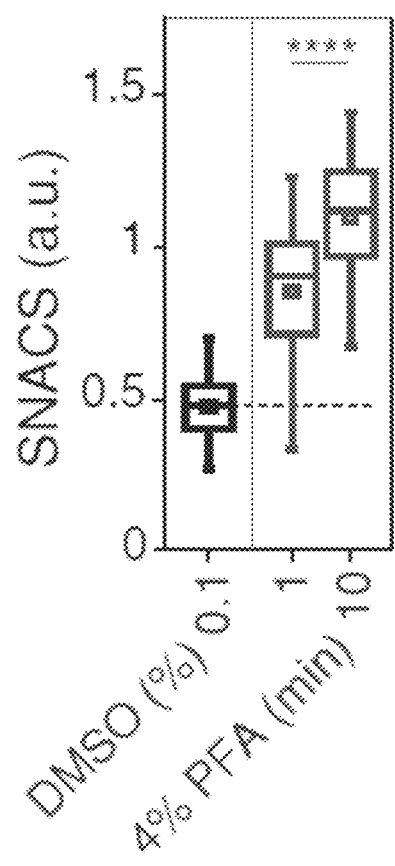
FIG. 14D is a plot of SNACS of L1210 cells after crosslinking with 4% Paraformaldehyde, according to one set of embodiments.
Figure 14E:
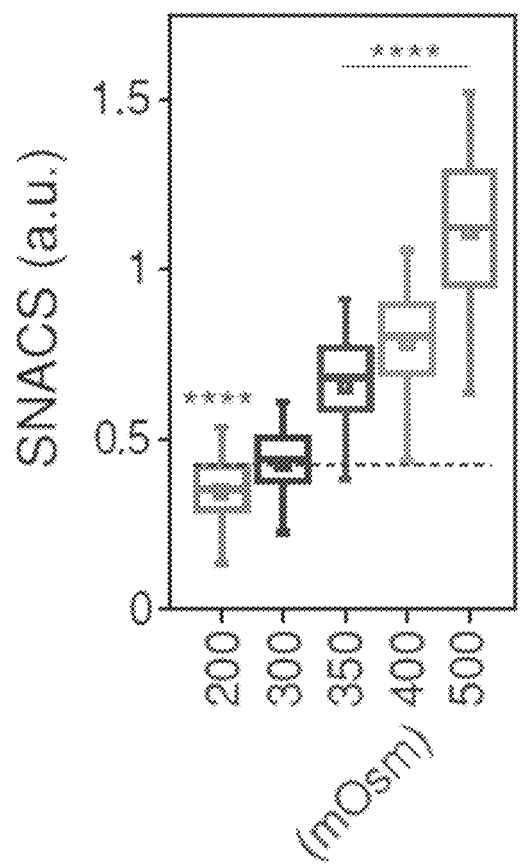
FIG. 14E is a plot of the effect of osmotic stress on SNACS, according to one set of embodiments.
Figure 23A:
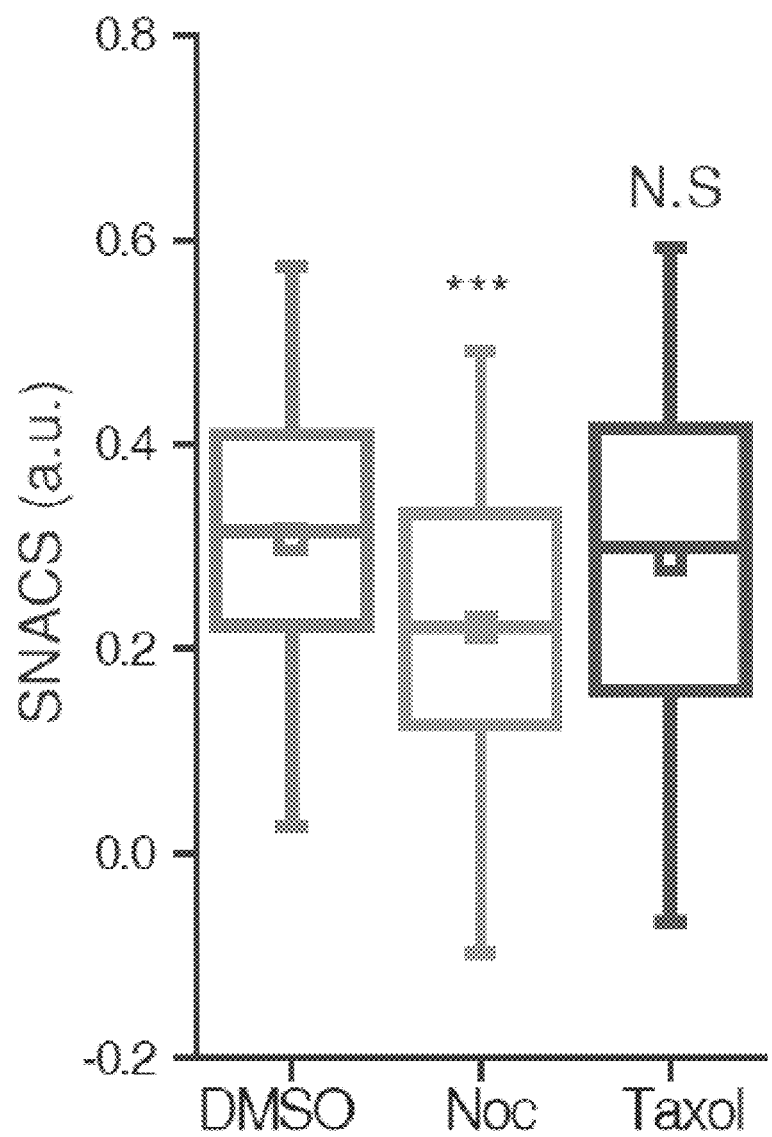
FIG. 23A is, according to certain embodiment, SNAGS measured from L1210 cells treated with microtubule affecting drugs: Nocodazole (Noc, 1 μg/ml, n=760) and Taxol (25 μM, n=511), with DMSO 0.1% control (n=718)

To validate whether SNACS correlates with stiffness of live cells, the SNACS upon stiffness perturbations were examined. All actomyosin inhibitors tested decreased the SNACS (see FIG. 14B, which shows SNACS obtained from L1210 cells treated with inhibitors of actomyosin cortex: Latrunculin B (LatB, n=381, 385, 346, and 383, respectively), Cytochalsin D (CytoD, n=332), and Blebbistatin (Bleb, n=349), with DMSO control (n=337)). A L1210 cell line was generated that stably expresses the LifeAct-RFP F-actin probe. These cells were imaged and it was observed that the chemical inhibitors of actin polymerization caused either a punctured cortex (Latrunculin B, LatB) or polarized cortex (Cytochalsin D, CytoD). FIG. 14C shows representative single z-layer images of F-actin (LifeAct) from live L1210 cells before and after 1 µM LatB and 1 µM CytoD treatment (scale bar is 10 µm). Both cortex phenotypes yielded a reduction in SNACS (p<0.0001), significantly more than system noise (FIG. 22A-FIG. 22C). A reduced SNACS after microtubule perturbing Nocodazole treatment was also observed, but this treatment also affected the actin cortex morphology (FIG. 23A and FIG. 23B). The opposite change in SNACS was observed when the cellular structures were cross-linked using a 1-10 minute exposure to 4% paraformaldehyde (see FIG. 14D, which shows SNACS of L1210 cells after crosslinking with 4% paraformaldehyde (PFA, 1 and 10 minute exposure, n=247 and 367, respectively, control n=1047)). Moreover, when cells were osmotically perturbed, SNACS varied correspondingly with the applied osmotic pressure. (see FIG. 14E, which shows the effect of osmotic stress on SNACS). Cells were treated with hypo- (200 mOsm, n=611), iso-(300 mOsm, n=539) or hyperosmotic (350, 400 and 500 mOsm, n=544, 571 and 574, respectively) media. These data show that the SNACS measurement corresponds to cell stiffness.

Example 4—Normalized Node Deviation

Although acoustic scattering provides accurate measurement of mechanical properties, it may also vary with particle size. In other words, particles with identical mechanical properties (e.g., same material) but only differs in their size would scatter distinctively. It has been shown both experimentally and numerically that acoustic scattering quadratically varies with particle/cell volume. Therefore, normalization of acoustic scattering by particle volume in order to compensate for the size effect and obtain pure mechanical information (e.g, Young's modulus) may be useful, in some cases.

Acoustic scattering without normalization would be valid itself when comparing populations of similar size range. The size effect would be equal for populations, and therefore acoustic scattering can be used as a direct proxy of mechanical properties. For example, drugs that perturb mechanical properties but not immensely on cell volume will create distinct acoustic scattering pattern. In this case, it can be directly compared to the untreated population without further size normalization. However, note that small differences can be sometimes masked by wide range of size within the population. If samples of interest have narrow size range, for example, acoustic scattering could be used without normalization.

In order to size normalize the measurement, single cell volume of the samples may be measured using two different fluids (e.g., having different density). Briefly, a buoyant mass in a fluid is determined by change in resonant frequency when particle is located at the antinode. Note that both acoustic scattering and buoyant mass of the particle are measured simultaneously by tracking resonant frequency shift when particles flow through the channel. Thus, acoustic scattering measurement at node on one side can be later normalized by volume obtained from two subsequent buoyancy measurements.

However, there are certain cases where particle volumes can be measured without fluid-switching method. For example, if a population of interest (e.g, L1210 cell line) is expected to have tight density distribution and number of particle is not limited for proper sampling, volume can be converted from a single buoyant mass measurement. This may increase the throughput of properly size normalized measurement to an order of ~1000 cells/hour.

There are two parameters for this normalization process: median volume ($\overline{V}$), and median buoyant mass ($\overline{f}_b$). Median population volume measurement can be readily done exploiting commercial Coulter Counter measurement or with imaging. Since median buoyant mass can be obtained by simply flowing particles through the SMR, particle volume can be obtained at the end of experiment using a simple equation, $V = f_b \times \overline{V}/\overline{f}_b$.

Quadratic scaling of node deviation (ND) with volume generally relates to ND/volume scalomg linearly with volume. Thus, particles of identical mechanical properties may be on a line in the volume vs ND/volume plot (isoelasticity lines). It was demonstrated experimentally as well as by numerical simulation that stiffness may affect the y-intercept of a line but not the slope. Isoelastiscity lines were vertically shifted downwards with decreasing stiffness, thereby placing more deformable samples on lines of lower y-intercepts (see FIGS. 10A-10C).

This provides a simple way of comparing populations of different mechanical properties. Each population can be linearly regressed with a common slope and corresponding y-intercept of each line conveys which population is softer than the other. Moreover, this can be expanded to a single-cell level using the similar method: Fit each point with a common slope and determine the y-intercept for relative mechanical comparison. Here, the common slope can be derived from the population measurement completed prior to the single-cell measurement. If population measurement cannot be performed due to rareness of samples, slope derived from mechanically similar samples or in similar materials would be sufficient. In addition, calibrating numerical simulation enables us to obtain absolute mechanical properties (e.g., Young's modulus, surface tension and etc.). Using well-characterized polystyrene beads, simulated data (energy, J) can be converted to experimental units (frequency, Hz), enabling simulated results to be plotted together with measurements in volume vs ND/volume space. Simulation of isoelastiscity lines may not only provide median stiffness of measured populations, but may also quantitatively map stiffness distribution for the population.

Figure 10A:
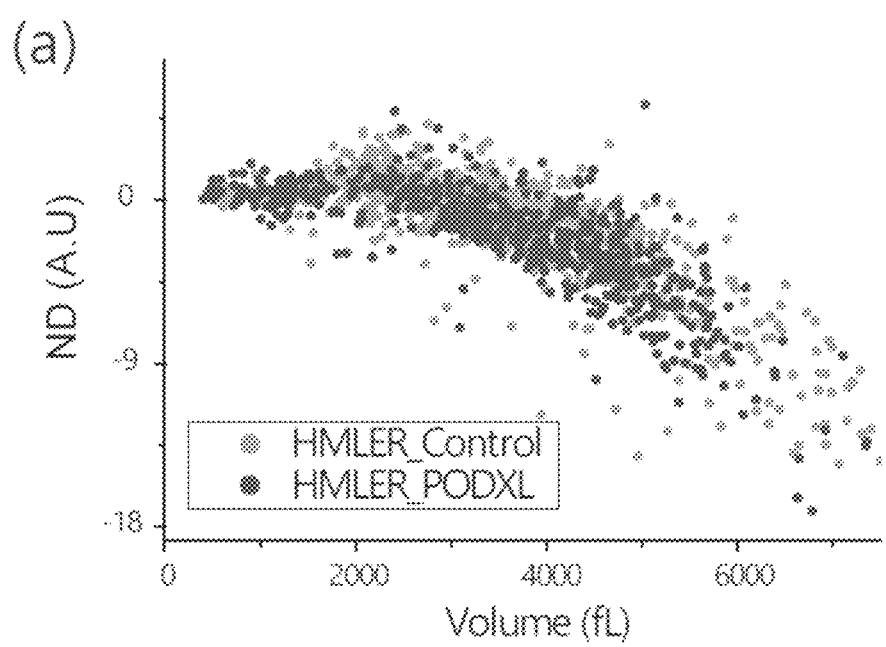
FIG. 10A is a plot of node deviation versus volume for a plurality of particles, according to one set of embodiments.
Figure 10B:
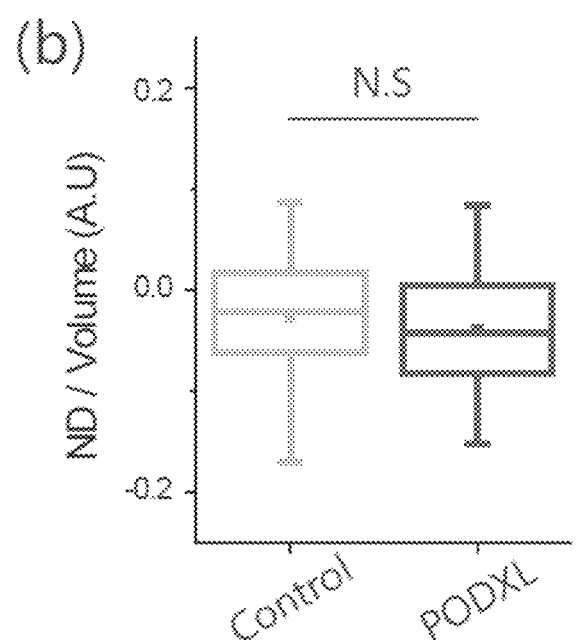
FIG. 10B is a plot of node deviation per volume for a plurality of particles, according to one set of embodiments.
Figure 10C:
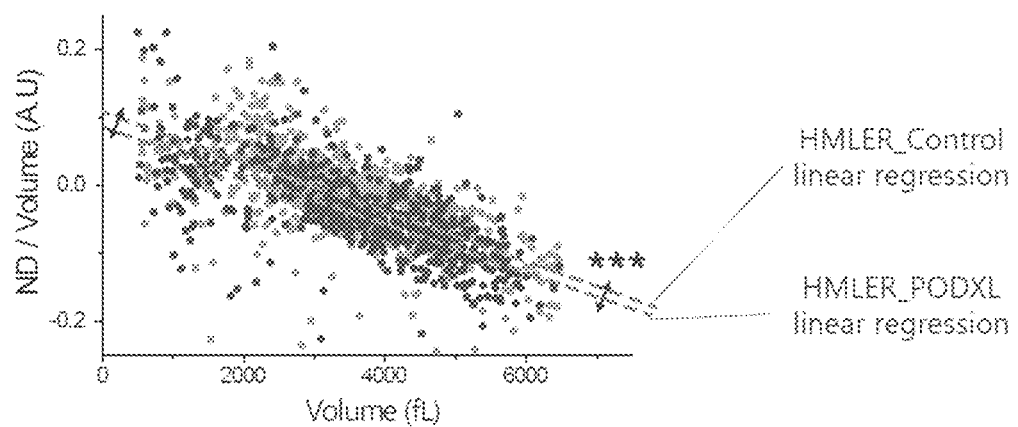
FIG. 10C is a plot of node deviation per volume versus volume for a plurality of particles, according to one set of embodiments.

FIGS. 10A-10C is an example of a case where acoustic scattering can be normalized as previously described. In FIG. 10A, unnormalized NDs of two epithelial cell lines are shown. Two samples cannot be distinguished from each other because of wide range of ND. Note the quadratic scaling of ND with cell volume. What is shown next in FIG. 10B is ND/volume (i.e. normalized node deviation) box plot of those two populations (box: interquartile, whiskers: 5-95%, inner box: mean, N.S: not significant). Although their median value differs, the range of dataset is too wide for statistical significance. Unnormalized ND box plot yields similar result.

Next, each population is regressed with linear line in volume vs ND/volume space (FIG. 10C). Linear regressions of the two populations demonstrate statistical difference (ANCOVA). Furthermore, the fitted lines can be compared to simulated results to obtain absolute mechanical stiffness (data not shown here).

Example 5—Detection of Single-Cell Therapeutic Sensitivity

Figure 11A:
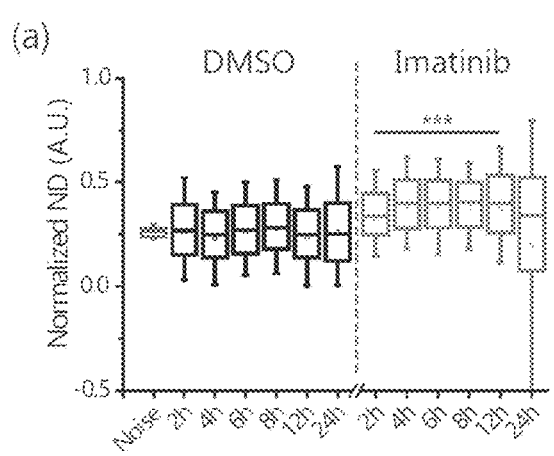
FIG. 11A is a plot of normalized node deviation versus time for Baf3 cells treated with DMSO or Imatinib, according to one set of embodiments.
Figure 11B:
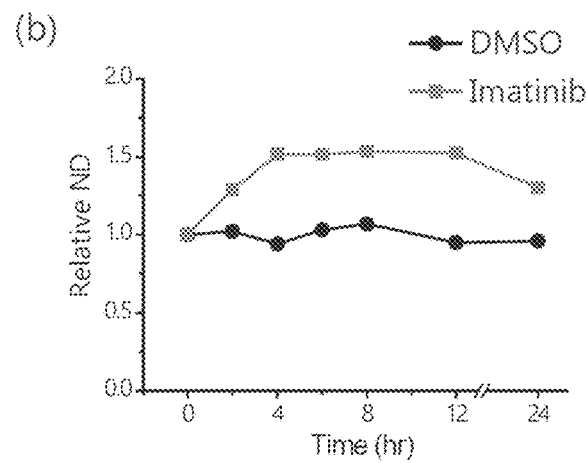
FIG. 11B is a plot of relative node deviation versus time for Baf3 cells treated with DMSO or Imatinib, according to one set of embodiments.

Acoustic scattering may be used as an early detection marker of single-cell therapeutic sensitivity (FIGS. 11A-11B). For example, Baf3 cells displayed distinct ND only a few hours of treatment with Imatinib, an anti-cancer drug that is known to slow growth or results in cell death. Viability and proliferation assays are generally not sensitive until 24 hours of drug exposure (data not shown).

Example 6—Mechanical Properties of Cells During Cell Cycle Progression

Figure 12A:
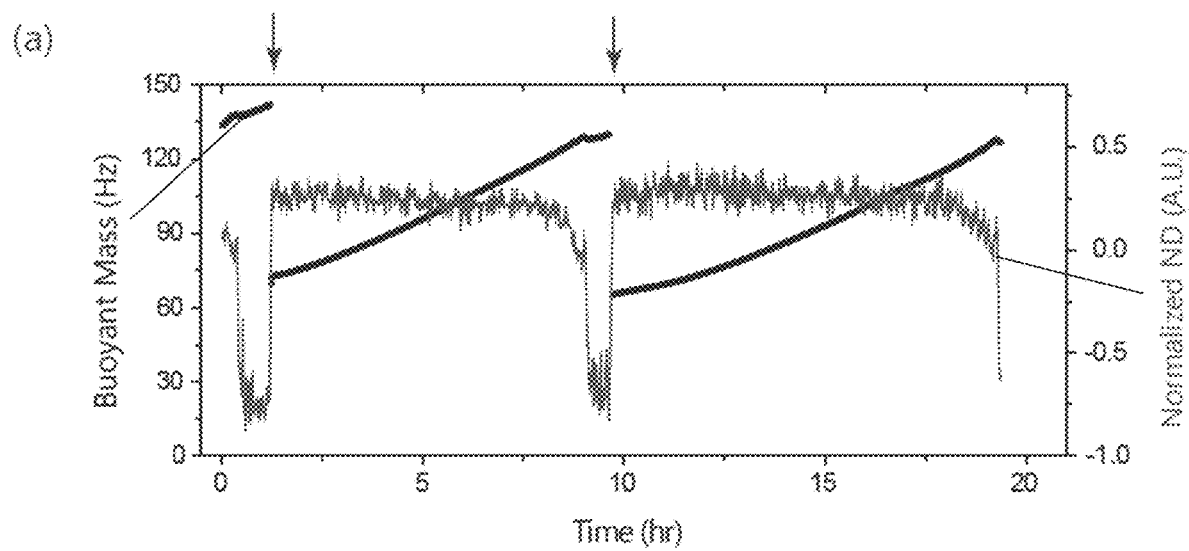
FIG. 12A is a plot of buoyant mass and node deviation versus time for L1210 cells, according to one set of embodiments.

Non-destructive nature of acoustic scattering measurement may be used for probing mechanical changes of single cells over many cell cycles. FIG. 12A shows L1210 single-cell trajectory over 20 hours (interdivision time is ~8-12 hours). Buoyant mass measurement shows cell growth and divisions (black arrows, top). Node Deviation, measured simultaneously with each mass measurement, probed mechanical changes during cell cycle progression. Acoustic scattering measurement revealed dynamic and fast mechanical changes in the late cell cycle.

Figure 12B:
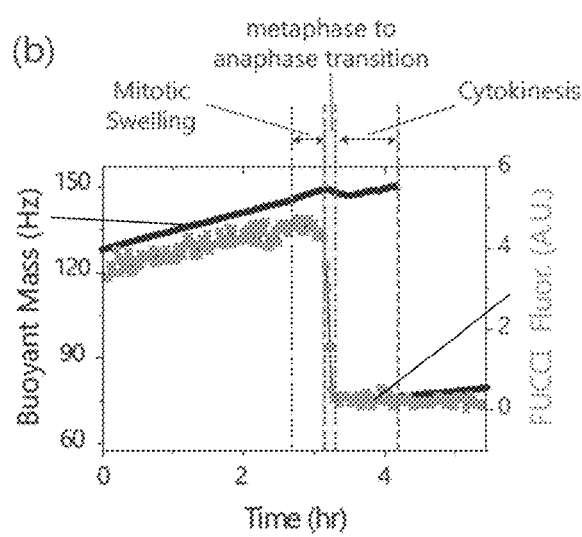
FIG. 12B is a plot of buoyant mass versus time for L1210 cells undergoing cell cycle progression, according to one set of embodiments.
Figure 12C:
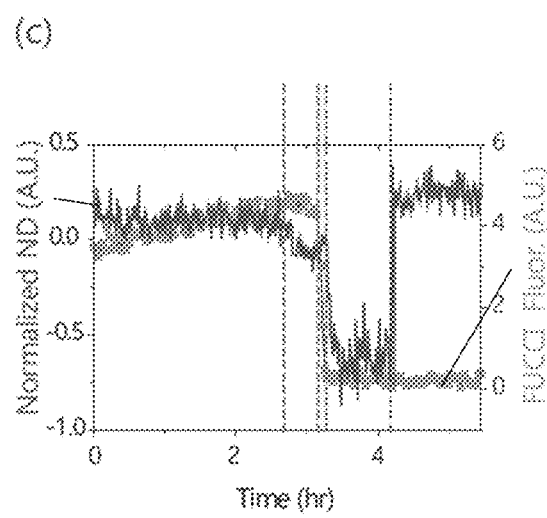
FIG. 12C is a plot of normalized node deviation versus time for L1210 cells undergoing cell cycle progression, according to one set of embodiments.

Additional techniques and tools, such as Fluorescence microscope, can be implemented to SMR for precise monitoring of cell-cycle progression (FIG. 12B). Mitotic swelling, a reversible fast volume regulation during prometaphase, marks G2-M transition. Furthermore, fluorescence of L1210 cells stably expressing fluorescently tagged proteins (geminin-mAG, green fluorescence) marks the metaphase checkpoint and the onset of anaphase. These may enable ND measurements to be precisely linked to specific cell cycle (FIG. 12C). Gradual decrease in ND is due to swelling which accompanies increase in intracellular water content as in case of hypotonic osmotic shock. Dynamic remodeling of mechanical components (e.g, cleavage furrow, contractile ring, cortical actin flow) during cytokinesis may be related to rapid decrease in ND. As such, and as compared to traditional methods such as buoyant mass, (normalized) node deviation may be able to show changes in cell cycle progression including, for example, the beginning and end of cytokinesis.

Example 7—Non-Invasive Monitoring of Single-Cell Mechanics by Acoustic Scattering This example describes a method for continuously and non-invasively monitoring the stiffness of single cells over time scales relevant to cellular changes, such as the cell cycle. In particular, the vibration of a suspended microchannel resonator (SMR), as shown in FIG. 13A, was utilized as an acoustic energy source, and it was investigated if the scattered acoustic fields from the cell could provide a signal to monitor its stiffness. The inset of FIG. 13A shows a conceptual illustration of frequency shift due to acoustic scattering, wherein a particle interacts with acoustic fields generated by the SMR vibration at resonant frequency f. The particle-fluid interaction causes acoustic scattering, which shifts the resonant frequency ($\Delta f$). The wavelength ($\lambda$) of the acoustic fields is depicted qualitatively ($\lambda \sim 1$ mm, which is ~100 times the channel height). The SMR is a cantilever-based microfluidic mass sensor that can be used, for example, to measure cell buoyant mass. Vibrating the SMR at its second mode (resonant frequency f) causes the vibration amplitude to vary along the length of the cantilever, with one local maximum (antinode) near the center and a zero-minimum (node) near the tip (see FIG. 13B, top, which shows vibration amplitude (normalized) at the 2nd mode). When a cell is at the antinode, the net change in mass (i.e. the buoyant mass of the cell) corresponds to a change in the kinetic energy of the system, and thus causes a shift in the resonant frequency of the SMR ($\Delta f/f|_{antinode}$). When the cell is at the node, the net change in mass is not expected to shift the resonant frequency ($\Delta f/f|_{node}=0$) because the vibration amplitude is zero and there is no change in kinetic energy. Surprisingly, a consistent resonant frequency shift at the node ($\Delta f/f|_{node}, \neq 0$) is observed when a single cell or polystyrene bead is flowed in the SMR (see FIG. 13B, bottom, which shows resonant frequency shift ($\Delta f/f$) from experiments with a single cell and a polystyrene bead). This resonant frequency shift (or "node deviation" ($\Delta f/f|_{node}$)) was different for cells and beads of similar buoyant mass. It was therefore hypothesized that i) node deviation corresponds to an energy change due to acoustic scattering from the cell's surface, ii) node deviation depends on cell stiffness.

Figure 13E:
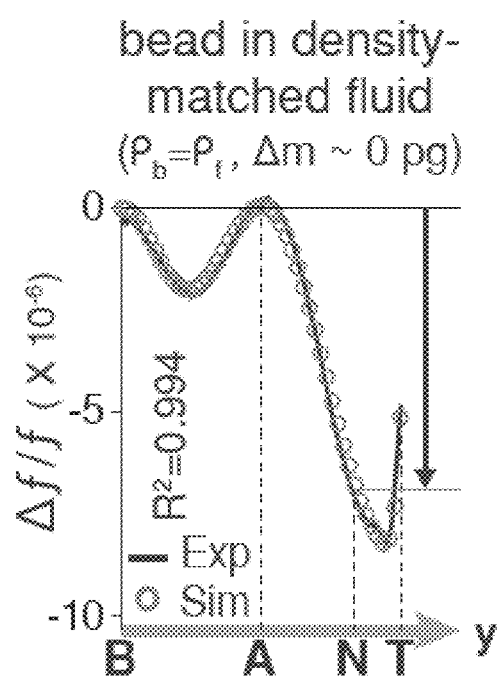
FIG. 13E is a plot of $\Delta f/f$ from simulations and experiments with polystyrene beads flowing through SMR filled with density-matched fluid ($\rho_{bead} = \beta_{fluid}$), according to one set of embodiments.

First, to determine if node deviation corresponds to acoustic scattering, Finite Element Method (FEM) simulations for fluid-structure acoustic interactions were utilized. This revealed that the acoustic pressures and velocities vary along the SMR similarly to the vibration amplitude. FIG. 13C, shows, for example, acoustic pressure and acoustic velocities within SMR from Finite Element Method simulations. See also FIG. 3A. Positioning a particle at the node changes the acoustic velocities (see the inset of FIG. 13C, which shows magnitudes of y-acoustic velocities with and without a polystyrene bead at the node). The resonant frequency shift was calculated by integrating the acoustic energy terms obtained from simulation. Excellent agreement ($R^2=0.984$) with the measurements was obtained (see FIG. 13D, which shows $\Delta f/f$ from simulations and experiments with polystyrene beads flowing through SMR filled with $H_2O$). It was confirmed that the particle-fluid density difference has negligible effect on node deviation (FIG. 5B, FIG. 5C, and FIG. 6A). To experimentally validate that the acoustic effects can be measured independently of the buoyant mass, a bead in a density-matched fluid ($\rho_{fluid}=\rho_{bead}$) was measured. This resulted in zero resonant frequency shift at the antinode ($\Delta f/f|_{antinode}=0$), but a noticeable resonant frequency shift at the node in both experiment and simulation, which showed excellent agreement with each other ($R^2=0.994$), as shown in FIG. 13E. Additional measurements revealed that node deviation is independent of the fluid velocity or the vibration amplitude of the SMR (FIGS. 17 and 18). Polystyrene particles were also compared with different volumes and it was observed that node deviation changes with particle volume (see FIG. 13F, which shows node deviation versus particle volume from experiments and simulations with polystyrene beads). The volume dependence can be corrected for by utilizing the buoyant mass measurement. Furthermore, analyzing uniform hydrogels with different aspect ratios revealed that node deviation is not sensitive to particle shape for particles with aspect ratios up to 1-2.5 (see FIG. 13G, which shows node deviation versus aspect ratio from experiments with synthetic hydrogels of different shapes but the same volume (n=384, 423 and 474 for aspect ratio 1, 1.5 and 2.5, respectively)). By measuring the resonant frequency shift at the node and antinode as a cell flows through the SMR, it is possible to simultaneously and independently quantify the acoustic scattering and buoyant mass of the cell.

Figure 15C:
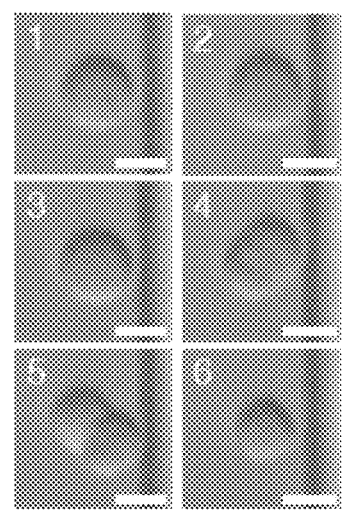
FIG. 15C is a representative morphology of a L1210 cell captured by DIC imaging on the SMR chip, according to one set of embodiments.
Figure 15D:
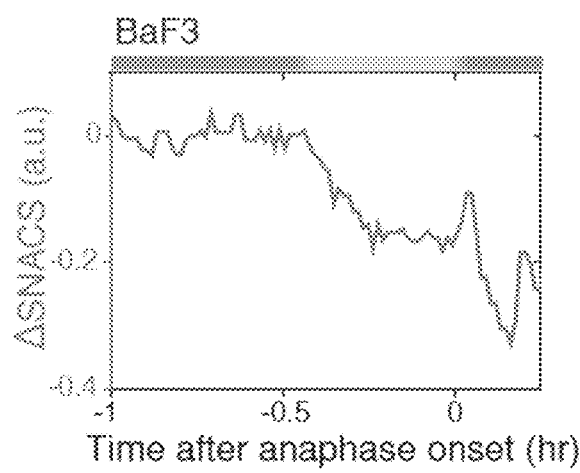
FIG. 15D is a plot of SNAGS in mamalian cells BaF3 versus time after anaphase onset, according to one set of embodiments.
Figure 15E:
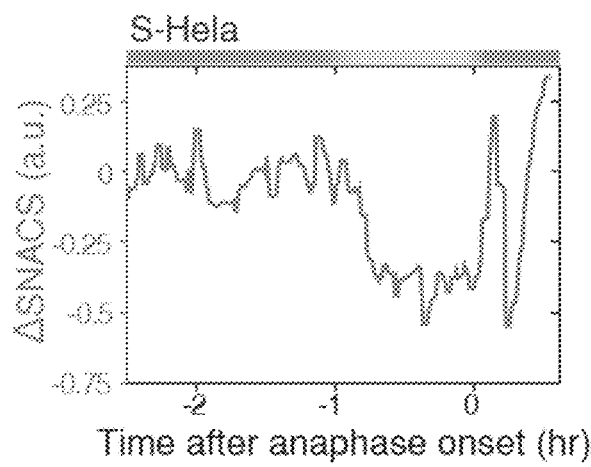
FIG. 15E is a plot of SNAGS in mamalian cells S-Hela versus time after anaphase onset, according to one set of embodiments.
Figure 25A:
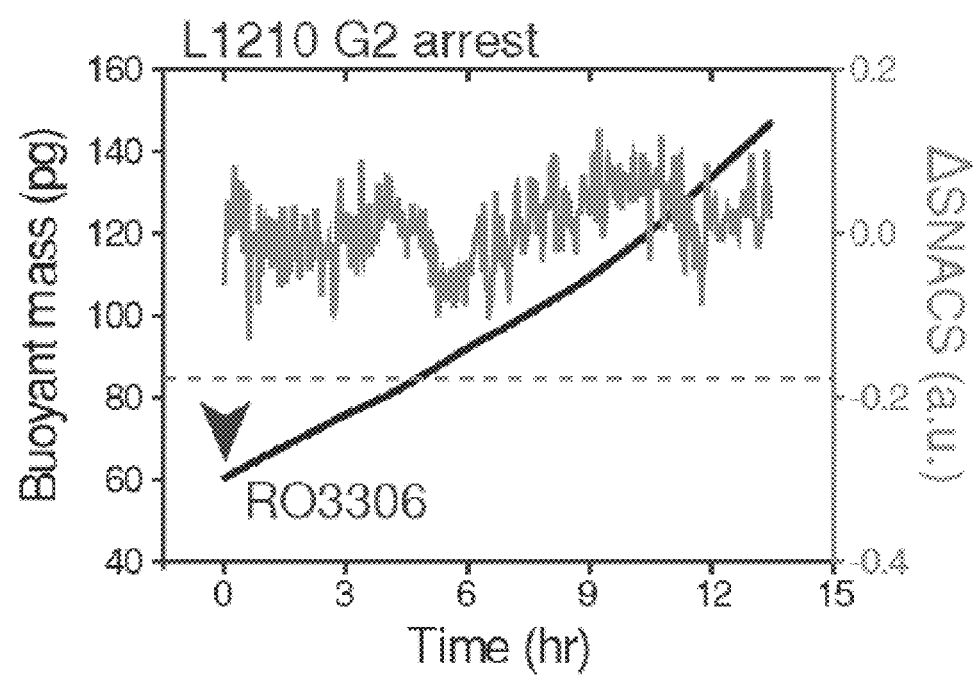
FIG. 25A shows, according to one set of embodiments, buoyant mass and SNACS of L1210 treated with 2 μM RO-3306, a CDK1 inhibitor.
Figure 25B:
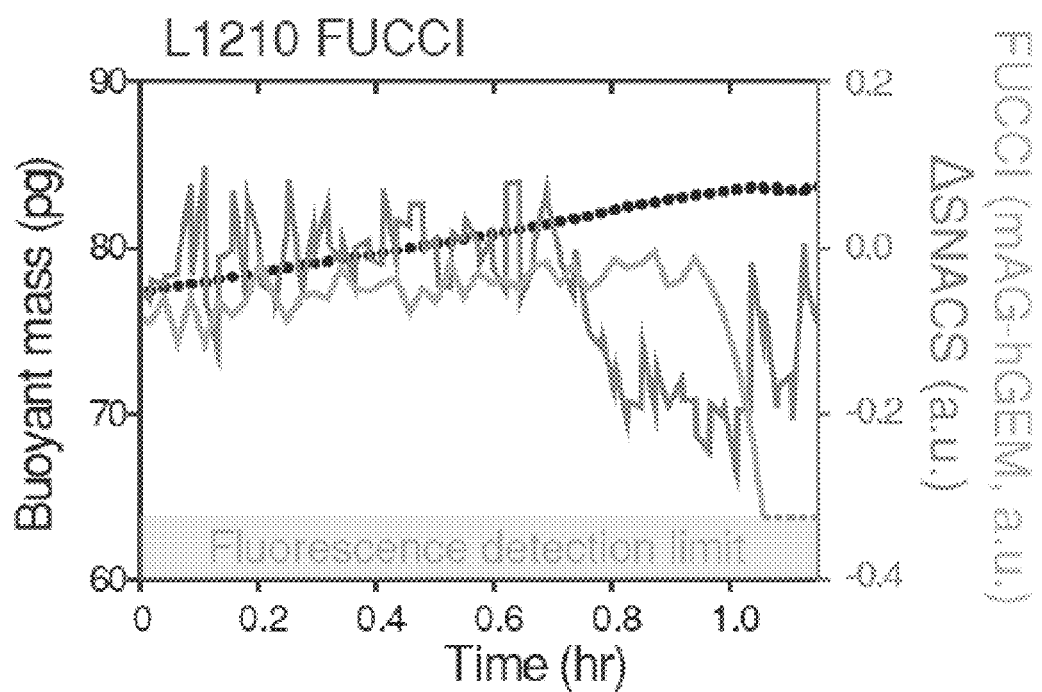
FIG. 25B shows, according to one set of embodiments, buoyant mass, SNAGS, and FUCCI (mAG-hGem) of a representative L1210 cell in mitosis.

Next, it was determined if both stiffness and buoyant mass of the same cell could be repeatedly measured in order to monitor cell stiffness during the cell cycle. To do so, a previously reported fluidic control strategy was implemented that enables continuous, non-invasive SMR measurements of the same cell. Employing on-chip microscopy capable of acquiring Differential Interference Contrast (DIC) images, stiffness, buoyant mass and morphology of the same cell over multiple generations was simultaneously measured. FIG. 15A shows the buoyant mass and SNACS of a L1210 cell measured over two cell divisions with <1 min temporal resolution by flowing the cell back-and-forth through the SMR, wherein the arrows mark cell division, and the inset shows SNACS near mitosis. SNACS is shown in dashed lines when measurement error becomes statistically significant. The morphology of the cell was imaged to pinpoint the onset of anaphase as well as to correct for mass elongation effects on the SNACS measurement during anaphase and telophase (FIG. 24A-24C). Dynamic but consistent changes in cell stiffness during mitosis were observed. FIG. 15B shows mean SNACS and standard deviation of L1210 cells during mitosis (n=24), where time zero marks the onset of anaphase, the vertical lines and bars indicate the phase of the cell cycle, the lines on the bottom mark the end of cell division for each cell, and the dashed line is the same as in FIG. 15A. FIG. 15C shows representative morphology of a L1210 cell captured by DIC imaging on the SMR chip, wherein the numbering corresponds to the arrows in FIG. 15B (scale bar is 10 μm). Stiffness decreased gradually during early mitosis, but not in G2, and abruptly increased at the onset of anaphase followed by a rapid decrease and recovery (FIGS. 25A and 25B). The error in the SNACS measurement increased after cells became full doublets (~15 min after the onset of anaphase), making subsequent stiffness changes until division not statistically significant (p>0.05). Although the duration and magnitude of the dynamics varied, we observed a similar trend in cell stiffness in other mammalian cell types: BaF3 (FIG. 15D) and S-Hela (FIG. 15E).

Given that stiffness scales inversely with swelling, it was hypothesized that mitotic swelling occurring in prophase and metaphase might be responsible for the gradual decrease in stiffness. To test this hypothesis, the timing of the mitotic swelling was correlated with the stiffness change by simultaneously measuring stiffness and cell volume. Briefly, cells in two fluids of different densities were consecutively weighted during each cycle in order to derive single-cell volume, density and mass using a previous technique. By combining this technique with the SNACS measurement, it was observed that the cell stiffness decreases concomitantly with mitotic swelling. FIG. 16A shows L1210 cell volume and SNACS in mitosis, where time zero marks the onset of anaphase. This was further validated by arresting cells in metaphase, where mitotic swelling is at a maximum, using kinesin inhibitor S-trityl-1-cysteine (STLC). Upon mitotic entry, STLC treated cells displayed similar change in stiffness to that seen during mitotic swelling of untreated cells. However, with STLC treatment, stiffness remained low for several hours. FIG. 16B shows buoyant mass and SNACS of a representative L1210 cell arrested in metaphase by treating with 5 μM S-trityl-cysteine (STLC). These results suggest that cell stiffness decreases concomitantly with mitotic swelling during prophase and metaphase and further confirm that the subsequent increase in stiffness happens after metaphase.

Figure 26:
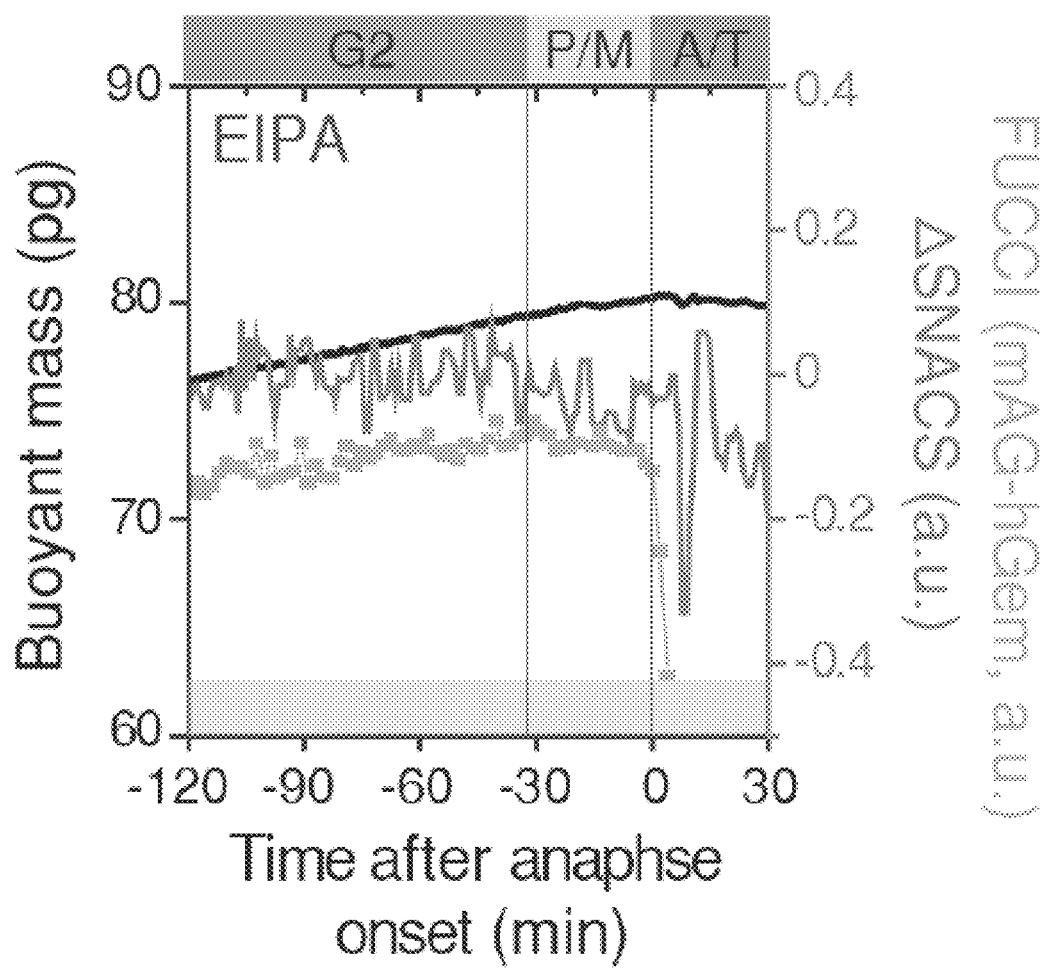
FIG. 26 is buoyant mass, SNACS, and FUCCI (mAG-hGEM) of a representative L1210 cell treated with 10 μM ethylisopropylamiloride (EIPA, an inhibitor of Na+/H+antiporters), according to some embodiments.
Figure 27:
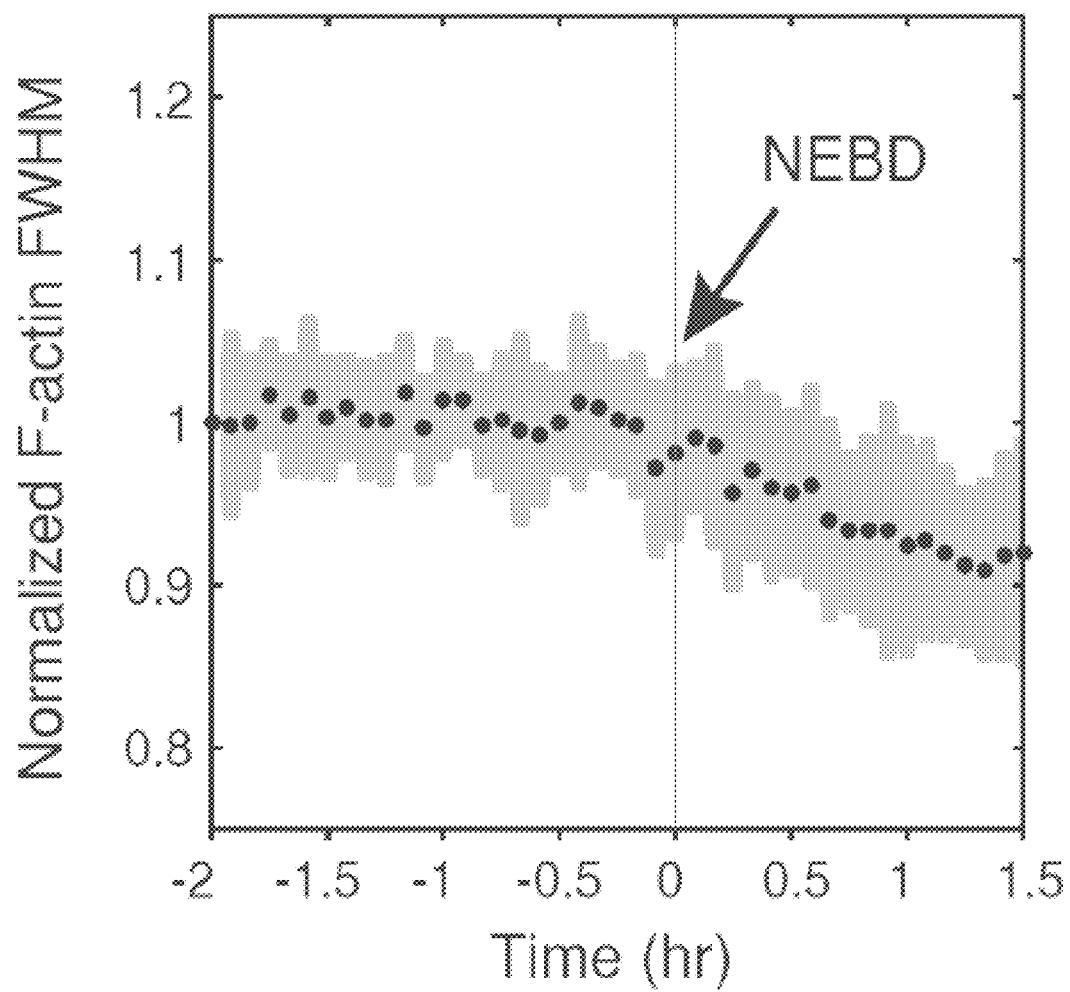
FIG. 27 is mean full width at half maximum (FWHM, proxy of cortical thickness, black dots) and standard deviation (gray) of cortical LifeAct signal from L1210 FUCCI cells expressing LifeAct-RFP F-actin probe in early mitosis (n=29), according to some embodiments.

It was hypothesized that mitotic swelling causes the reduction in stiffness during prophase and metaphase. Inhibiting Na+/H+ antiporter with ethylisopropylamioride (EIPA) reduces the magnitude of mitotic swelling without inhibiting mitosis. Upon EIPA treatment, cell stiffness in early mitosis was no longer reduced to the same extent ($\Delta$SNACS=−0.08±0.02, see FIG. 16C and FIG. 26) as in the control cells and cells arrested in metaphase ($\Delta$SNACS=−0.22±0.01 and 0.24±0.03), suggesting that mitotic swelling is largely responsible for the reduction in stiffness. FIG. 16C shows mean SNACS change of control and 10 μM ethylisopropylamiloride (EIPA) treated L1210 cells in early mitosis, where time zero marks the onset of anaphase, and the right side shows the quantification of SNACS change with 5 μM STLC and 10 μM EIPA treatments, where the data depicts mean±standard deviation of the SNACS change in prophase and metaphase (n=24, 8, and 5, respectively). To determine if swelling without a mitotic event can decrease stiffness, swelling was induced with a hypotonic shock (−α50 mOsm) in non-mitotic (interphase) cells. Immediately after the osmotic shock, cells swelled by ~15% in volume, as normally observed in mitotic swelling, and cell stiffness was reduced by a similar magnitude ($\Delta$SNACS=−0.18±0.01) to that seen during mitotic swelling. FIG. 16D shows an illustration of hypothetical cortical thinning scenario by shell expansion during swelling on the top, and the bottom shows SNACS of L1210 cells versus time before (red, n=728) and after (−$\Delta$50 mOsm, n=733) exposure to hypotonic stress. The dashed lines represent the mean SNACS of each condition, and the arrow marks the time of osmotic shock. It was hypothesized that the swelling reduces both cortical thickness and cortical stiffness by hydrostatic pressure expanding actin to cover a larger surface area. Swelling of ~15% would lead to ~10% cortex thickness decrease assuming the cortical actin content is conserved during swelling. To determine that the cortex thickness indeed decreases during mitotic swelling, live cell fluorescent microscopy was utilized. It was observed that the cortex thickness gradually decreases by an amount similar to the calculation of ~10% after nuclear envelope breakdown, but before the onset of anaphase (FIG. 27 and FIG. 28A-28H). Altogether, these data suggest that mitotic swelling is directly responsible for cortical thinning and consequent decrease in stiffness.

Figure 16E:
FIG. 16E is a representative single z-layer images of F-actin and FUCCI from a live L1210 cell, according to one set of embodiments.
Figure 16F:
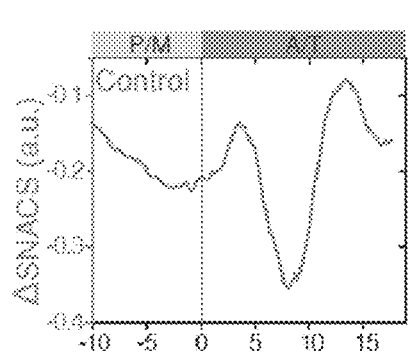
FIG. 16F is a zoom-in view of mean SNACS in late mitotic L1210 cells, according to one set of embodiments.
Figure 16H:
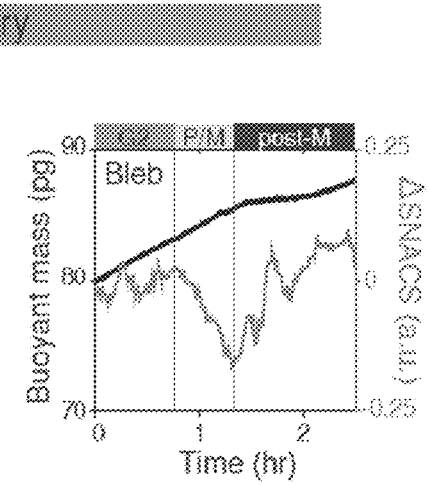
FIG. 16H is a plot of the buoyant mass and SNACS of a representative L1210 cell treated with 25 μM Blebbistatin (Bleb), according to one set of embodiments.
Figure 16G:
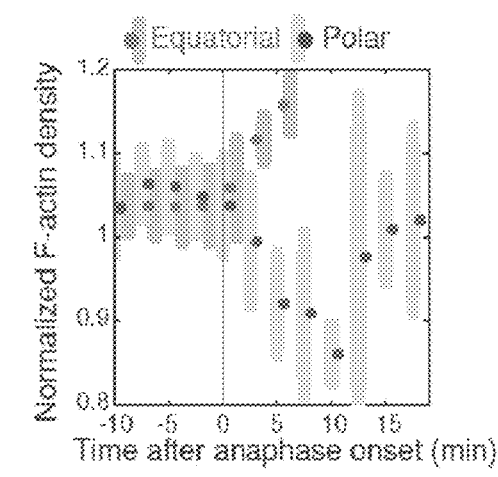
FIG. 16G is L1210 cortical LifeAct signal density in equatorial and polar regions, according to one set of embodiments.
Figure 16I:
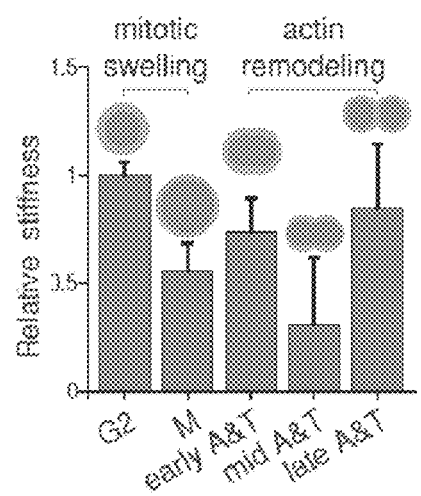
FIG. 16I is a summary of stiffness dynamics in mitosis, according to one set of embodiments.
Figure 29:
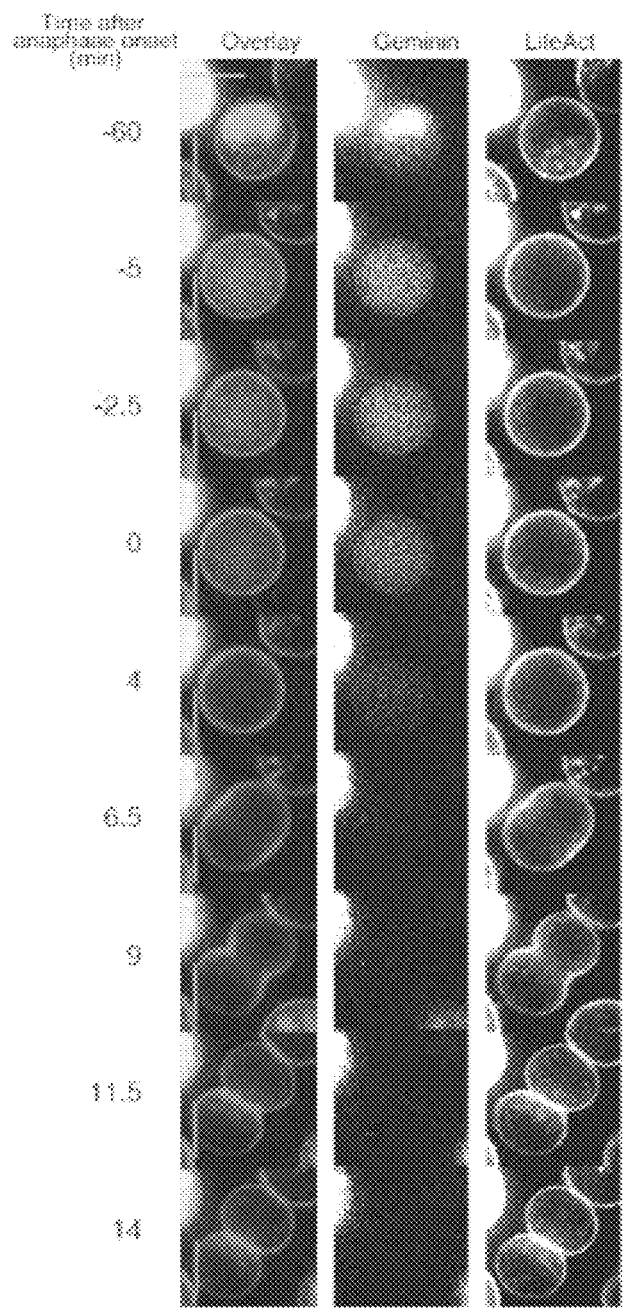
FIG. 29 shows fluorescence images of F-actin and FUCCI in late mitosis, where the left column is an overlay of LifeAct and FUCCI as a function of time after anaphase onset, the middle column is Geminin fluorescence from the green channel only and the right column is LifeAct fluorescence from the red channel only, according to certain embodiments

The rapid stiffness dynamics observed during anaphase and telophase were investigated. It was observed that the stiffness increase in early anaphase was not present in EIPA treated samples (FIG. 26), suggesting that this increase in stiffness represents recovery from the mitotic swelling. To better link the stiffness dynamics to actin remodeling, actin cortex distribution changes were imaged during anaphase and telophase (FIG. 29). FIG. 16E shows representative single z-layer images of F-actin (LifeAct) and FUCCI (mAG-hGem) from a live L1210 cell, where time zero marks the onset of anphase. Furrow initiation in the equatorial region (arrowheads) and cortical relaxation at the poles (arrows) are highlighted. In early anaphase (~5 minutes after the onset of anaphase) where stiffness initially increases, cells started to elongate and the cleavage furrow was initiated. At approximately 10 minutes into anaphase, where stiffness decreased, cells redistributed their cortical actin out of the polar regions. This polar relaxation caused a 10-15% depletion in F-actin at the poles and lasted approximately 5 minutes. Both stiffness and polar relaxation were recovered approximately 15 minutes after the onset of anaphase. FIG. 16F shows a zoom-in view of mean SNACS in late mitotic L1210 cells (n=24), and FIG. 16G shows L1210 cortical LifeAct signal density in equatorial and polar regions. The data represents mean values (dots) and standard deviation (bars) (n=7), and time zero marks the onset of anaphase. When cytokinesis and actin remodeling were inhibited with the myosin II motor inhibitor Blebbistatin, cells still displayed a gradual stiffness decrease in early mitosis caused by mitotic swelling, but the stiffness dynamics observed in anaphase and telophase of untreated cells disappeared. FIG. 16H shows the buoyant mass and SNACS of a representative L1210 cell treated with 25 μM Blebbistatin (Bleb). Together, these observations reveal how cortical thinning induced by mitotic swelling in early mitosis and actin remodeling, especially polar relaxation, in late mitosis result in dynamic cell stiffness behavior (see FIG. 16I, which shows a summary of stiffness dynamics in mitosis, where the data depicts mean±standard deviation of the SNACS normalized to G2, and actin and morphology of a cell in each time points of mitosis are illustrated).

Through experiments involving cytoskeletal perturbations and ELM simulations, scattered acoustic fields from a cell—determined by the SNACS measurement—is a proxy for cell stiffness and dominated by the cell cortex. The ability to measure single-cell stiffness continuously, with high temporal resolution over extended periods, is critical for observing small changes which are both transient and asynchronous between cells. This has been demonstrated by measuring mitotic-specific stiffness changes that are smaller than the population variance and occur within minute timescales. Importantly, the measurements quantify the overall stiffness of a cell, complementing spatially resolved measurements such as time-lapse microscopy and AFM.

Example 8—Methods

The following example describes experimental methods, including system setup, system operation, frequency peak analysis, hydrogel particle synthesis, cell culture, chemical perturbations and transfections, size normalizing node deviations to obtain SNACS values, cell cycle transition points, microscopy, image analysis, and statistics and data presentation.

SMR devices were fabricated at CEA-LETI, Grenoble, France. The geometry and dimensions of SMR devices used in the experiments described in this work are shown in FIG. 3A. The fluid channel in the detection regime is covered with thin silicon layers. The inset shows the buried channel and dimensions are listed in Table 1. The SMRs were vibrated with a piezo-ceramic plate bonded underneath the chip, providing actuation to resonate the cantilever beam in the second mode. To track the changes in the resonant frequency of the cantilever as a function of time, the cantilever was kept in a feedback loop oscillating at its resonant frequency. The motion of the cantilever was measured using piezoresistors that are implanted at the base of the silicon cantilever. A digital control platform was utilized to oscillate the SMR in direct feedback mode, where the motion signal acquired from the piezoresistor is delayed, amplified, and utilized as the drive signal used to actuate the cantilever. The measurement bandwidth of this control system was set at ~1,500 Hz, which is wide enough to capture frequency modulation signals created by cell transit events and narrow enough to minimize noise.

TABLE 1

List of FEM simulation parameters.

| Parameter | Values (units) | Description |
|---|---|---|
| w | 20 (μm) | burried channel width |
| h | 15 (μm) | burried channel height |
| L | 315, 350 (μm) | cantilever (channel) length |
| t | 2 (μm) | top, bottom silicon layer thickness |
| d | 5 (μm) | fluid channel separation |
| A | 1-100 (μm) | vibration amplitude |
| $r_p$ | 3-6 (μm) | particle radius |
| $r_c$ | 3-7 (μm) | total radius of a cell model |
| $t_s$ | 0.5-5 (%) | thickness of the shell, relative to the radius |
| $E_p$ | 0.1-100 (MPa) | bulk Young's modulus of the particle |
| $E_s$ | 2-10 (MPa) | Young's modulus of the shell in liquid-core elastic-shell model |
| $p_f$ | 0.997-1.08 (g/cm$^3$) | fluid density |
| $p_c$ | 1.05 (g/cm$^3$) | cell density (both inner core and outer shell) |
| $p_p$ | 1.05 (g/cm$^3$) | bead density |
| $v_c$ | 0.5 | cell poisson's ratio (outer shell) |
| $v_p$ | 0.34 | bead poisson's ratio |

For on-chip optical measurements, a modular microscope (Nikon) was mounted on top of the SMR device. A 20× objective lens (Nikon-CFI, LU Plan ELWD N.A 0.4 WD 13 mm) or 50× objective lens (Nikon-CFI, LU Plan ELWD N.A. 0.55, W.D 10.1 mm) was used to collect light into a CMOS camera (FLIR, BFS-U3-13Y3M-C) or PMT (Hamamatsu, H10722-20), respectively, in order to obtain DIC images or measure fluorescent intensity. The field of view and area of light exposure was typically reduced to 100 μm×100 μm (DIC imaging) or 40×60 μm (Fluorescent measurements) to minimize the background noise as well as phototoxicity. To further improve the signal-noise ratio, a rectangular slit (Thorlab) was adjusted to fit the channel width and placed at the image plane. An illumination light source (Lumencor, Spectra X Light Engine) was shuttered by the measurement software (Labview 2010) to excite each fluorescent measurement for less than 550 ms.

The system was operated by placing a chip on top of a hollow copper plate that is connected to a water bath by tubing to maintain constant temperature on the chip. For all single-cell, long-term monitoring experiments, the temperature of the copper plate was kept at 37° C. The sample was loaded to the SMR from vials pressurized with air containing 5% $CO_2$ to maintain the pH of the culture. A 0.007" inner diameter fluorinated ethylene propylene (FEP) tubing (IDEX Health & Science) was utilized to push the sample into the chip. The fluid flow was controlled using two electronic pressure regulators (Proportion Air QPV1) and three solenoid valves (SMC-S070), which were controlled by National Instruments control cards and a custom measurement software (Labview 2012). Typically, differential pressure of ~0.5 psi was applied across the SMR, yielding a flow rate of ~2 nL/s (calculated based on the frequency modulation signal due a cell transit; typically 200-300 ms) to maintain constant shear and data rate. Under these conditions, the L1210 cell growth rate was similar to that in culture. Beads, hydrogels and drug-response end-point assays were measured at room temperature. All end-point assays were conducted within 30 minutes after samples were loaded. New samples were flushed every several minutes into the input bypass to minimize potential size bias due to particle/cell settling in the tubing and sample vials.

To measure buoyant mass (antinode) and node deviation (node) from the acquired resonant frequency waveforms, the frequency data was filtered with a third order Savitzky-Golay low-pass filter and the local minima (antinode) that is below a user-defined threshold. Next, local maxima (node) around the peaks were determined. To correct for the possible slope during the particle/cell transition through the cantilever, a baseline was calculated and subtracted from the measured peaks by fitting a first order polynomial at frequency data points prior and posterior of the cell signal. For single-cell volume measurements (FIG. 16A), baselines were fitted with a second order polynomial to account for the baseline fluctuation due to fluid exchange. Both local maxima and minima in the cell signal were subtracted from the linear baseline to obtain the buoyant mass (local minima, antinode) and node deviation (local maxima, node). For single-cell end-point assays (population measurements), frequency peaks were rejected when local minima (two antinodes) differed from each other more than 10% of the average value and/or local maxima (two nodes) differed from each other more than 15% of the average value of local minima, which occur when multiple cells or cell with debris enter the SMR simultaneously. Peaks were rejected if their shape was atypical (e.g., particle/cell stuck in the cantilever). For single-cell long-term monitoring, all frequency peaks were accepted and presented except for extremely rare events, such as when a doublet separated into two daughter cells during the transit through the cantilever or entered apoptosis due to persistent drug pressure. Frequency peaks were calibrated (Hz per pg) using monodisperse 10 μm diameter polystyrene beads with a known density of 1.05 g/cm$^3$ (Thermofisher, Duke Standards).

Hydrogel microparticles were fabricated via stop-flow lithography. Microfluidic synthesis devices were fabricated according to the following procedure: Briefly, PDMS (10:1 monomer to curing agent, Sylgard 184, Dow Corning) was cured on silicon wafers patterned with SU-8 features, and devices were bonded to PDMS-coated glass slides. Prepolymer solutions were prepared by mixing 20% (v/v) poly (ethylene glycol) diacrylate (PEGDA; Mn=700, Sigma-Aldrich), 5% 2-hydroxy-2-methyl-propiophenone (photoinitiator, Sigma-Aldrich), 25% DI water, and 50% polyethylene glycol (PEG; Mn=200, Sigma-Aldrich). Using the SFL setup, prepolymer solution was loaded into the synthesis device by pressure-controlled flow. After stopping the flow, particles were polymerized by ultraviolet light (Thorlabs, 365 nm LED, 2200 mW cm$^{-2}$) in mask-defined shapes (transparency masks designed in AutoCAD, printed by Fineline Imaging). The three steps (flow, stop, exposure) were repeated to achieve semi-continuous particle synthesis. Polymerized particles were collected from the channel outlet and purified with PBST (phosphate buffered saline with 0.05% Tween-20) by centrifugation. Three masks were used, in which the three masks had different aspect ratios, but the same total area: an 11 μm circle, an ellipse with aspect ratio of 1.5 (major axis:minor axis), and an ellipse with aspect ratio of 2.5. Particles were synthesized in microfluidic channels with heights of 10 µm, resulting in a particle heights of 7-8 µm. Mean volume of hydrogels were 655, 658 and 602 µm3 for aspect ratios 1, 1.5 and 2.5, respectively. Particle dimensions (height and major/minor axes) were measured from brightfield microscopy images using ImageJ software, taking an average from at least ten particles.

L1210 and BaF3 cells were cultured in RPMI containing L-glutamine, Phenol Red, 11 mM D-glucose, and the RPMI was supplemented with 10% heat inactivated fetal bovine serum (FBS), 10 mM HEPES, 100 units/mL of penicillin, 100 µg/mL of streptomycin, and 0.25 µg/mL of Amphotericin B. S-HeLa cells were cultured in DMEM containing L-glutamine, Phenol Red, 25 mM D-glucose, and the DMEM was supplemented as RPMI. All cell culture reagents were obtained from Thermo Fisher Scientific, except FBS which was obtained from Sigma-Aldrich. The L1210 cells were obtained from ATCC (CCL-219). BaF3 cells expressing BCR-ABL were obtained from RIKEN BioResource center. S-HeLa cells were a gracious gift from Dr. Kevin Elias. All experiments were started from cell cultures that had not reached more than 40% confluence.

For chemical perturbations, cells were pretreated with chemicals for 20-30 minutes under normal cell culture conditions and loaded into the SMR along with the chemical containing media. Chemical concentrations used were 0.1% DMSO (controls, Sigma-Aldrich), 0.02-1 µM Latrunculin B (Sigma-Aldrich), 1 µM Cytochalsin D (Sigma-Aldrich), 25 µM (inhibiting Cytokinesis, long-term traces) or 50 µM (Actomyosin cortex disruption, end-point assay) Blebbistatin (Sigma-Aldrich), 10 µM EIPA (Sigma-Aldrich), 5 µM STLC (Sigma-Aldrich) and 2 µM RO3306 (R&D Systems). For surface crosslinking experiments, cells were treated with 4% PFA (Electron Microscopy Sciences) in PBS for 1 or 10 minutes. Cells were then washed with PBS and resuspended in normal culture media. For all wash and re-suspension steps, cells were centrifuged at 500 g for 2 minutes. For the osmotic challenge, desired osmolarity of the external solutions were achieved by mixing cell culture media with deionized water or D-mannitol (Sigma-Aldrich) for hypotonic or hypertonic conditions, respectively. Cell culture media was set to be isotonic (300 mOsm). Cells in the culture media were mixed 1:1 with the prepared external solution (e.g., mixed 1:1 with 500 mOsm solution to achieve final osmolarity of 400 mOsm) to obtain desired osmolarity. The cells were kept in the prepared media solution at room temperature for 20 minutes before loading them into the SMR containing media of the desired osmolarity. For hypotonic experiment shown in FIG. 16D, cells were loaded immediately after the osmotic shock.

L1210 FUCCI cells, which express the fluorescence cell cycle marker construct mAG-hGem, were transfected with LifeAct, a F-actin labelling red fluorescent protein construct, using rLVUbi-LifeAct-TagRFP lentiviral vector obtained from ibidi GmbH. Several rounds of transfections were carried out using spinoculation. In short, 1.5×105 L1210 FUCCI cells were mixed with 10 µg/ml Polybrene (EMD Millipore) and 1×106 TU of lentivirus, and the mixture was centrifuged at 800 g for 60 minutes at 25° C. After centrifugation, the cells were moved to normal cell culture media, grown overnight, and the spinoculation procedure was repeated. Cells were moved to normal culture media after three rounds of transfections, and 24 hours later, selection was started by adding 10 µg/ml Puromycin (Sigma-Aldrich). After a week of selection, the transfected population was enriched for cells expressing high levels of LifeAct by FACS sorting using BD FACS Aria.

Figure 19:
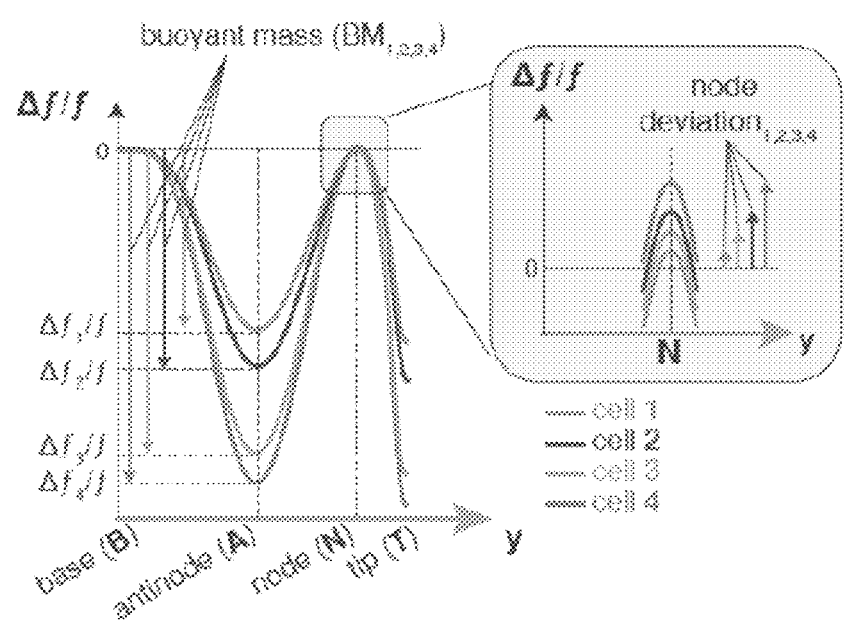
FIG. 19 is the resonant frequency shifts (Δf/f) for each cell 1-4, used to measure the buoyant mass (BM) at the antinode and the node deviation at the node, according to one set of embodiments.

Since node deviation decreases with particle volume (FIG. 13F and FIG. 14A), size-normalization is generally required to compare stiffness of different size particles or cells. To obtain the size-normalized acoustic scattering (SNACS), the volume was first obtained. In short, the buoyant mass obtained from individual peaks were converted to volume using a median density of the population, as shown in FIG. 19. Median density of the population relative to the fluid ($\overline{\Delta\rho}=\overline{\rho_c}-\overline{\rho_f}$) was obtained by fitting the buoyant mass distribution with a log-normal distribution to estimate the mean buoyant mass ($\overline{BM}$, >300 cells). Mean volume ($\overline{V}$) was obtained by fitting the log-normal distribution to the volume distribution obtained from the Coulter Counter measurements (Beckman Coulter, >5000 counts). Single-cell volume was then obtained using the following equation:

$$V = BM/\overline{\Delta\rho}, \text{ where } \overline{\Delta\rho} = \frac{\overline{BM}}{\overline{V}}$$

Figure 20A:
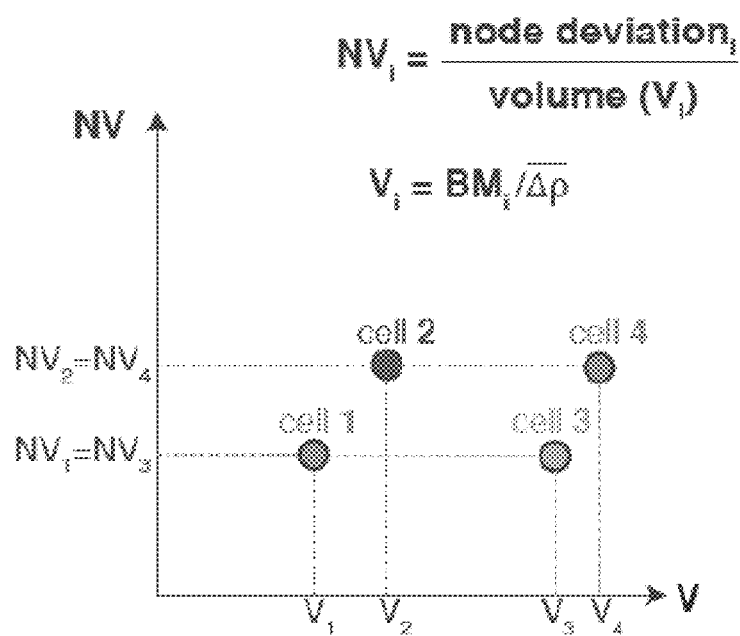
FIG. 20A is a scatter plot of volume-normalized node deviation (NV) vs volume (V), according to one set of embodiments.
Figure 20B:
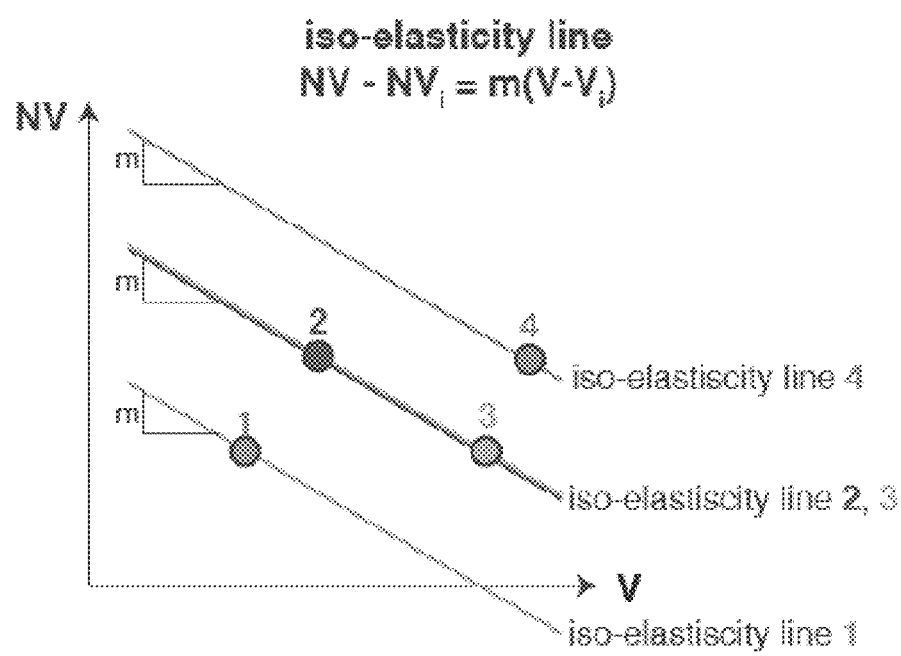
FIG. 20B is the volume of each cell obtained from the corresponding buoyant mass, according to one set of embodiments.
Figure 20C:
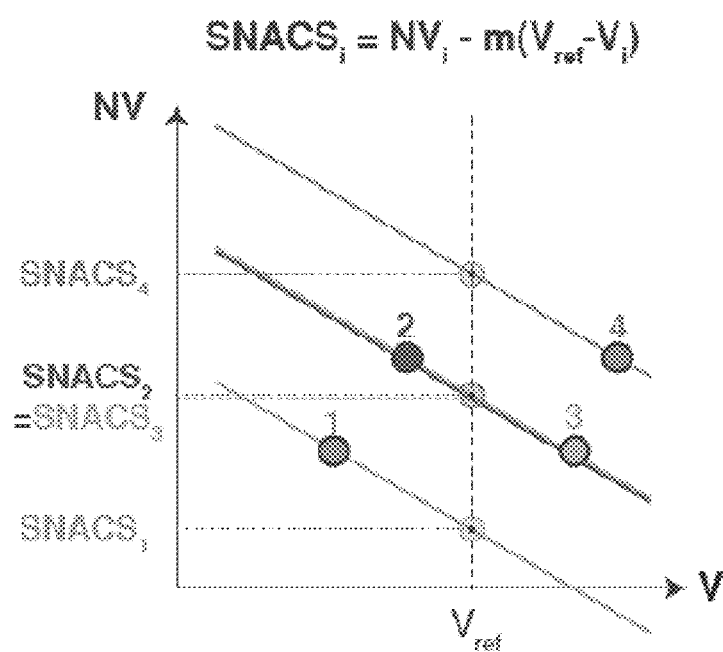
FIG. 20C is the slope (m) obtained by performing a linear regression on the population data in the NV vs V scatter plot shown in FIG. 14A, according to one set of embodiments.

The mean density ($\overline{\Delta\rho}$) of the population was calculated for each condition. Then, the node deviation for each cell (FIG. 19) was divided by its volume (V) to obtain node deviation/volume (NV). Representing each cell as a data point in the scatter plot (NV vs V, FIG. 20A), an iso-elasticity line of slope m is passed through each point (FIG. 20B). All data points along a given iso-elasticity line have the same stiffness based on the FEM simulation (FIG. 14A). Finally, the SNACS for each cell was obtained by taking the linear interpolation of NV at $V_{ref}$ along the iso-elasticity line (FIG. 20C):

$$SNACS=NV-m(V_{ref}-V)$$

The slope (m) was obtained by performing a linear regression on the population data (typically >300 cells) in the NV versus V scatter plot (FIG. 14A). The reference volume ($V_{ref}$) was set to the median volume of the population, which for L1210 cells was 900 fL.

To pinpoint cell cycle transition points, such as the G2/M transition, a finding that mitotic swelling starts in early prophase and prometaphase was utilized. As the SNACS decrease was simultaneous with swelling (FIG. 16A), and SNACS decrease was not observed in G2 arrested cells (FIG. 25A and FIG. 25B), the G2/prophase transition was marked to take place right before the SNACS decrease starts. The FUCCI signal (mAG-hGem) decrease (when fluorescence first reaches 85% of the maximum value) was used to mark the metaphase to anaphase transition. Based on fluorescence imaging, the average time lag between the time when FUCCI signal (mAG-hGem) begins to drop (below 85% maximum) and the first time point for when a cell deviates from spherical was approximately 3.8 minutes. Then, to assign the cell cycle transition points in figures, the 3.8 minutes time lag was subtracted from the first time point when cell shape deviates from sphere to mark the start of anaphase. SNACS traces of the metaphase arrested cells (treated with STLC), where SNACS remained low for several hours, supported our timing of the metaphase-anaphase transition (FIG. 16A).

L1210 cells expressing the FUCCI (mAG-hGem) and LifeAct-RFP F-actin probe (rLVUbi-LifeAct-TagRFP) constructs were imaged on poly-lysine coated glass bottom CellView cell culture dishes (Greiner Bio-One). Media, $CO_2$, and temperature conditions during the imaging were the same as within the SMR. Imaging was carried out using a DeltaVision widefield deconvolution microscope with standard FITC and TRICT filters, 100× oil immersion objective and immersion oil with refractive index of 1.522. No binning was used and the image resolution was 9.245 pixels/μm in xy-planes. When examining the effects of actin perturbing chemicals on the F-actin structure, a 3 μm thick section from the middle of the cells was imaged in 0.2 μm thick z-layers. After the first round of imaging, the cells were treated with the indicated chemical for 30 minutes, and the same cells were imaged again. When examining the F-actin distribution in early mitosis, a 1 μm thick section from the middle of the cells was imaged in 0.2 μm thick z-layers every 5 minutes. Only the middle z-layer was used for final analysis and presentation. When examining the F-actin distribution during cytokinesis, three 0.2 μm thick z-layers were imaged with 1 μm height intervals to capture both the mother and the daughter cells at the central height of the cell, and this imaging was repeated every 2.5 minutes. The total duration of all imaging experiments was limited to 5 hours, as prolonged light exposure induced photo-toxicity and started to interfere with mitotic progression.

Figure 28A:
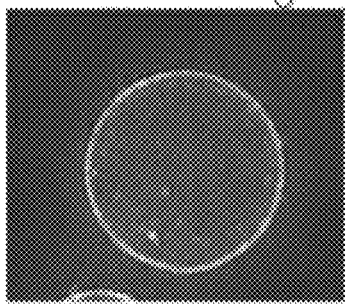
FIG. 28A is a deconvolved image of the LifeAct signal from a L1210 FUCCI cells expressing LifeAct-RFP F-actin probe, according to one set of embodiments.
Figure 28B:
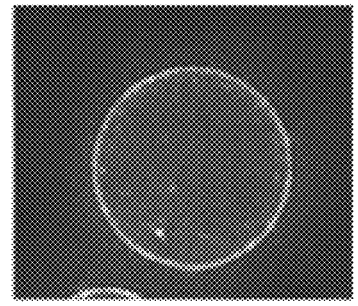
FIG. 28B is the image of FIG. 28A after applying median filter.

All images were deconvolved using standard settings in the softWoRX software. To normalize the effect of photobleaching, the total LifeAct signal in the entire images (2048×2048 pixels) that contained multiple cells was calculated. Then, a second order polynomial was fit to the total LifeAct signal in the image as a function of frame index. During the subsequent image analyses, the LifeAct intensity was corrected with the corresponding decay coefficient calculated from the polynomial fit for each frame. To analyze individual cells, the representative cells that went through the nuclear envelope breakdown and/or cytokinesis during the experiment were determined. These cells were cut out of the larger images and analyzed individually (FIG. 28A).

Figure 28C:
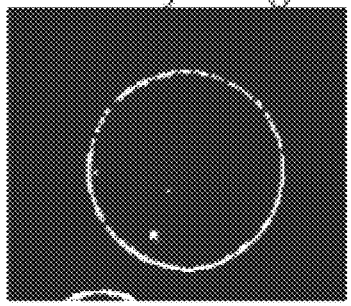
FIG. 28C is the binary converted image of FIG. 28A.
Figure 28D:
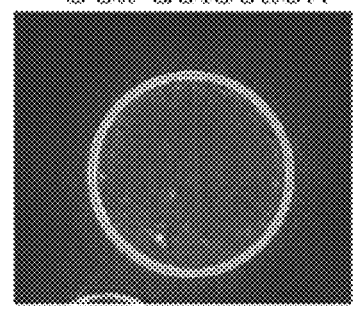
FIG. 28D is the automatic detection of cell boundaries of FIG. 28C.
Figure 28E:
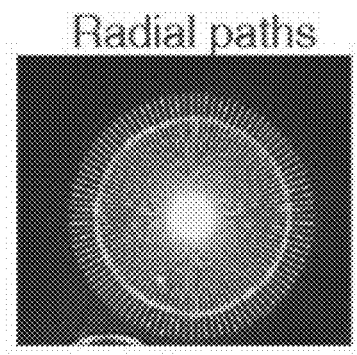
FIG. 28E is 100 radial paths on which the LifeAct signal was quantified of FIG. 28D.
Figure 28F:
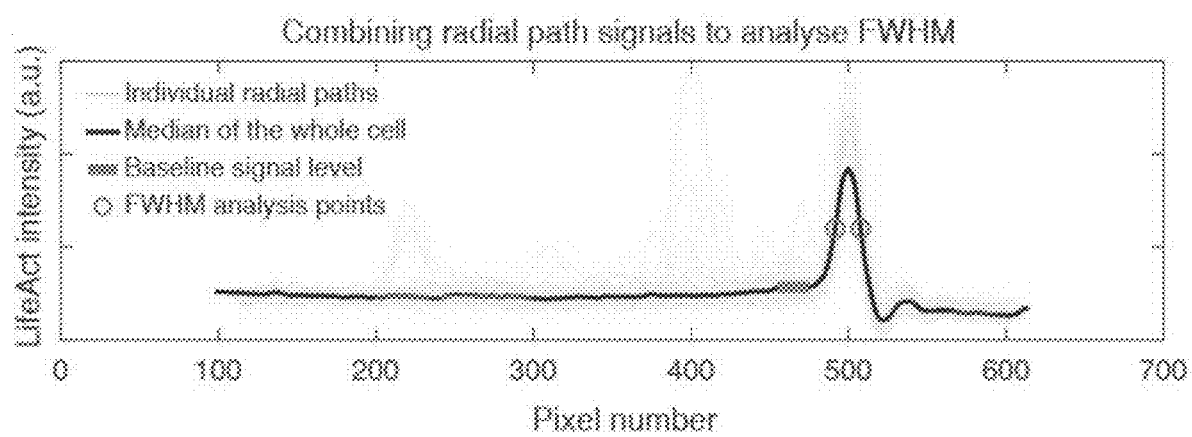
FIG. 28F is am overlaid view of all the radial path signal as a function of distance from the cell center; according to one set of embodiments.
Figure 28G:
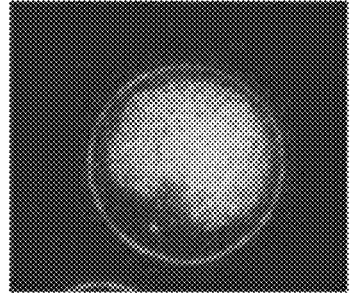
FIG. 28G is the nuclear envelope breakdown (NEB) detected by the abrupt spread of the green Geminin fluorescence of the FUCCI from a restricted nuclear localization, according to some embodiments.
Figure 28H:
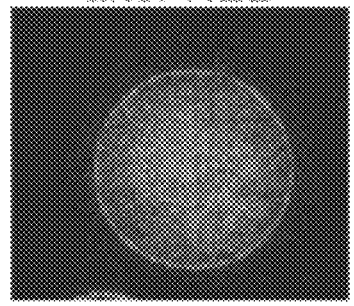
FIG. 28H is the nuclear envelope breakdown (NEB) detected by the abrupt spread of the green Geminin fluorescence of the FUCCI to the whole cytoplasm, in certain embodiments.

For analyzing each cell, MATLAB's circular Hough transform algorithm was utilized to detect circles on images (imfindcircles). This algorithm was applied to binary images that were processed by a 2-dimensional median filter with 3-by-3 neighborhood (FIG. 28B) and a threshold filter (FIG. 28C). After determining an initial position for the cell center and radius (FIG. 28D), the actin signal at the raw, unfiltered image across 100 radial paths around the detected circle ranging from the estimated cell center to 125% of the estimated cell radius was obtained (FIG. 28E). Then, the prominent peak location of the actin signal that was closest to the estimated radius as the cortex position for that particular radial path was recorded. The median of LifeAct signals recorded from each radial path was taken after aligning them at their calculated cortex locations (FIG. S29F). Using this median LifeAct profile of the cell cross-section, the full width at half maximum (FWHM) of the LifeAct signal at the cortex was calculated (FIG. S29F, circles) in reference to the LifeAct signal that is recorded at the cytoplasm. The baseline signal at the cytoplasm of L1210 cells was defined as approximately 85 to 90% of the radial measurement path (FIG. S29F). This FWHM value of LifeAct at the cortex functioned as a proxy for the cortex thickness.

To analyze F-actin distribution dynamics through mitosis, the analysis for each time point that was collected throughout the experiment was repeated. At each time point, the distribution of the FUCCI signal (mAG-hGem) in the cell was analyzed (FIG. S29G). The data from different cells was aligned to the time of nuclear envelope breakdown using the FUCCI signal (mAG-hGem) spread from nucleus to across the entire cell area as marker for the nuclear envelope breakdown (FIG. S29H). Finally, for comparing different cells, the FWHM signals of each cell was normalized with respect to the median FWHM signal that was recorded from the frames of that cell prior to the nuclear envelope breakdown.

Figure 30:
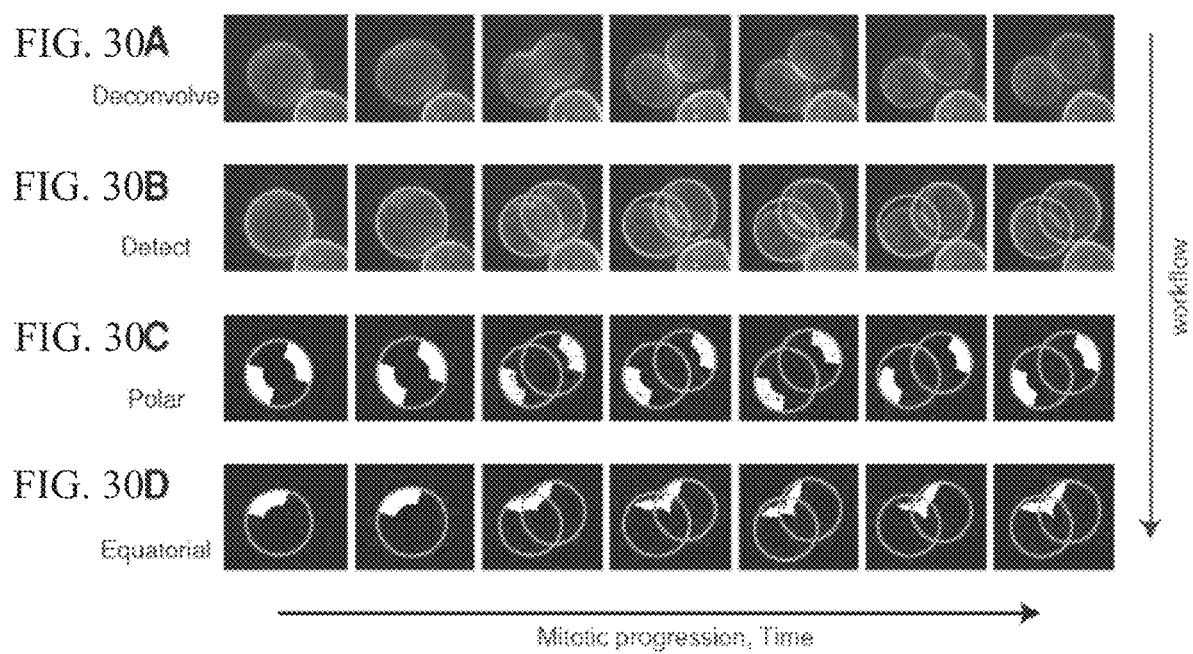
FIG. 30A shows deconvolved images of a L1210 FUCCI cell expressing LifeAct-RFP F-actin probe, according to certain embodiments.
FIG. 30B shows detection of one or two cells in the image of FIG. 30A (circles)
FIG. 30C shows assigning of the polar regions of FIG. 30B (white areas)
FIG. 30D shows assigning of the equatorial regions of FIG. 30B (white areas)

To study how the distribution of F-actin changes through mitosis, four regions of the cell were considered. Each region covers a 90-degree area extending from 65% of the estimated radius of the cell to its full radius. The same cell detection algorithm that was described previously was utilized, with the additional capability of detecting two adjacent cells (FIG. 30A and FIG. 30B). To determine the division axis and the regions of interest, the analysis was started from the frames after cytokinesis with two cells clearly visible, and worked back in time until the onset of anaphase. At each time point, if two cells were detected, even if the cell was in mid-anaphase, the division axis and the equatorial and polar regions of interest were determined. The polar region was set as the 90-degree segments that are at two opposite sides of the detected cells (FIG. 30C). The equatorial region was set as the regions that are in the middle of the two cells and have an angular span that is perpendicular to the polar regions (FIG. 30D). To compensate for the observed non-circular shapes, an edge detection algorithm was utilized to determine the true extent of the cells overlapping with the region of interest. If a single cell was detected, the four equal area regions were defined using the same angular span that was determined in the previous frames (during cytokinesis) of the same cell. Finally, the relative F-actin density in each region was calculated by normalizing the total LifeAct signal to the area in each region. In the cases, where an adjacent, brighter cell was interfering with the cell of interest, the signal in the affected region was disregarded. Finally, the timing of different cells using the first frame was aligned, where two separate cells are apparent (mid-anaphase).

To characterize the system noise, node deviation of the same 12 μm diameter polystyrene bead was repeatedly measured and size-normalized to SNACS, and their standard deviation was calculated (FIG. 22A). SNACS of L1210 cells (n=24) were aligned to the latest time point where the cells maintained round morphology (3.8 minutes after anaphase onset, FIG. 15C and FIG. 15D). Each data points for 0.01 hour was then interpolated, and the mean value and standard deviation of the interpolated data for each time point was calculated. All SNACS plots were filtered with median filter of length 3, except in late mitosis (data points after anaphase onset) where raw data was shown. From the onset of anaphase, p-values were calculated between the maximum and minimum within moving 5 minute time blocks to characterize how much of the temporal change has statistical power. It was observed that temporal SNACS changes were not statistically significant ($p>0.05$) from 15.2 minutes after the onset of anaphase to cell division. All p-values were calculated using Welch's t-test.

After defining the size-normalized acoustic scattering parameter SNACS at the end of FIG. 14, all node deviation changes were illustrated, which reflect the stiffness of a cell, using SNACS or ΔSNACS. ΔSNACS represents the change in SNACS relative to the median value of first 10-15 minutes of data presented (except in FIG. 16D, where mean value of the whole cells before hypotonic shock is used), and is only used for better visualization of data).

To quantify the agreement between the data from the experiments and the simulations, the coefficient of determination R-squared or $R^2$ was calculated. It was assumed that the observed data are the experiments and the fitted are the simulations. Thus, for number N of data points where $y_{i,experiment}$ and $y_{i,simulation}$ are the observed and the fitted values (i=1, 2, . . . N), it can be calculated:

$$R^2 = 1 - \frac{\sum (y_{i,experiment} - y_{i,simulation})^2}{\sum (y_{i,experiment} - \bar{y})^2},$$

where $\bar{y} = \frac{1}{N} \sum y_{i,experiment}$

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, curvilinear, non-linear, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed:

1. A method for determining a property of a particle, comprising:
   oscillating a suspended microchannel at a frequency within 10% of a resonant frequency of the suspended microchannel;
   flowing the particle in the suspended microchannel; and
   determining an acoustic scattering signal of the suspended microchannel while the particle flows through the suspended microchannel, wherein determining the acoustic scattering signal comprises determining a node deviation, wherein the node deviation comprises a difference in the resonant frequency of the suspended microchannel when the particle is at a node location of the suspended microchannel and the resonant frequency of the suspended microchannel when the particle is not in the suspended microchannel.

2. A method as in claim 1, wherein the frequency is a frequency of a mechanical resonant mode comprising a node, which is a location on the suspended microchannel with zero out-of-plane vibration.

3. A method as in claim 1, wherein determining the acoustic scattering signal comprises determining the resonant frequency of the suspended microchannel, when the particle is at the node location.

4. A method as in claim 1, wherein determining the acoustic scattering signal comprises determining the node deviation divided by a volume of the particle.

5. A method as in claim 4, wherein the volume of the particle is determined by weighing the particle with the suspended microchannel in two fluids with different densities.

6. A method as in claim 4, wherein the volume of the particle is determined by a median volume of a plurality of particles of the same type.

7. A method as in claim 1, wherein the acoustic scattering signal corresponds to the property of the particle.

8. A method as in claim 1, wherein the property of the principle comprises a mechanical deformability of the particle.

9. A method as in claim 1, comprising stimulating the particle and determining a change in the acoustic scattering signal after stimulating the particle versus before stimulating the particle.

10. A method as in claim 9, wherein the change in the acoustic scattering signal corresponds to a change in the property of the particle.

11. A method as in claim 1, wherein the particle is a living cell.

12. A method as in claim 1, wherein the particle is a virion, bacteria, protein complex, exosome, cell, or fungi.

13. A method as in claim 12, wherein the property of the particle comprises a thickness of a cortex of the cell.

14. A method as in claim 12, wherein the property of the particle comprises a cell cycle stage of the cell.

15. A method as in claim 9, wherein the particle is a living cell and stimulanting the particle comprises pertrubing a media, where the living cell lives.

16. A method as in claim 1, wherein determining the property of the particle does not comprise flowing a reference particle in the suspended microchannel.

17. A method for determining a property of a plurality of particles, comprising:
   oscillating a suspended microchannel at a frequency within 10% of a resonant frequency of the suspended microchannel;
   flowing the plurality of particles through the suspended microchannel; and
   determining an acoustic scattering signal of the suspended microchannel for the plurality of particles flowing through the suspended microchannel, wherein determining the acoustic scattering signal comprises determining a node deviation, wherein the node deviation comprises a difference in the resonant frequency of the suspended microchannel when a particle of the plurality of particles is at a node location of the suspended microchannel and the resonant frequency of the suspended microchannel when the particle is not in the suspended microchannel.

18. A system for determining a property of a particle, comprising:
   a suspended microchannel;
   a detector configured to measure a determinable acoustic scattering signal when the particle is flowed in the suspended microchannel; and
   a controller configured to oscillate the suspended microchannel at a frequency of a mechanical resonant mode of the suspended microchannel,
   wherein the mechanical resonant mode comprises a node such that the acoustic scattering signal changes when the particle is present at the node, and
   wherein the determinable acoustic scattering signal comprises a node deviation, wherein the node deviation comprises a difference in a resonant frequency of the suspended microchannel when the particle is at a node location of the suspended microchannel and the resonant frequency of the suspended microchannel when the particle is not in the suspended microchannel.

19. A system as in claim 18, wherein the determinable acoustic scattering signal comprises the resonant frequency of the suspended microchannel, when the particle is at the node of the suspended microchannel.

20. The method as in claim 1, wherein the property of the particle comprises a mechanical property.

21. The method as in claim 20, wherein the mechanical property is a stiffness of the particle, a Young's elastic modulus of the particle, a cross-linking density of the particle, and/or a transport rate of one or more small molecules into and/or out of the particle.

22. A method for determining a property of a particle, comprising:
- oscillating a suspended microchannel at a frequency within 10% of a resonant frequency of the suspended microchannel;
- flowing the particle in the suspended microchannel;
- determining an acoustic scattering signal of the suspended microchannel while the particle flows through the suspended microchannel; and
- determining the property of the particle based upon the acoustic scattering signal of the suspended microchannel, wherein the property of the particle comprises a mechanical property.

23. The method as in claim 1, wherein the mechanical property is a stiffness of the particle, a Young's elastic modulus of the particle, a cross-linking density of the particle, and/or a transport rate of one or more small molecules into and/or out of the particle.

\* \* \* \* \*

UNITED STATES PATENT AND TRADEMARK OFFICE
CERTIFICATE OF CORRECTION

| | |
|---|---|
| PATENT NO. | : 11,754,486 B2 |
| APPLICATION NO. | : 16/624000 |
| DATED | : September 12, 2023 |
| INVENTOR(S) | : Joon Ho Kang et al. |

It is certified that error appears in the above-identified patent and that said Letters Patent is hereby corrected as shown below:

In the Claims

At Column 41, Claim 8, Lines 65 - 66:
"wherein the property of the principle"
Should be:
--wherein the property of the particle--

At Column 42, Claim 15, Lines 17 - 18:
"stimulanting the particle comprises pertrubing a media"
Should be:
--stimulating the particle comprises perturbing a media--

Signed and Sealed this
Seventh Day of May, 2024

Katherine Kelly Vidal
*Director of the United States Patent and Trademark Office*